United States Patent
Penafuerte Diaz

(10) Patent No.: US 11,672,844 B2
(45) Date of Patent: Jun. 13, 2023

(54) METHOD OF TREATING OR AMELIORATING A PATHOGENIC INFECTION BY ADMINISTERING AN INTERLEUKIN-2/TGF-β RECEPTOR FUSION POLYPEPTIDE

(71) Applicant: Cura Therapeutics, Inc., Montreal (CA)

(72) Inventor: Claudia Ania Penafuerte Diaz, Montreal (CA)

(73) Assignee: Cura Therapeutics, Inc., Montreal (CA)

( * ) Notice: Subject to any disclaimer, the term of this patent is extended or adjusted under 35 U.S.C. 154(b) by 0 days.

(21) Appl. No.: 17/673,691

(22) Filed: Feb. 16, 2022

(65) Prior Publication Data

US 2022/0257712 A1    Aug. 18, 2022

Related U.S. Application Data

(60) Provisional application No. 63/150,450, filed on Feb. 17, 2021.

(51) Int. Cl.
| | | |
|---|---|---|
| A61K 38/17 | (2006.01) | |
| C07K 14/71 | (2006.01) | |
| C07K 14/55 | (2006.01) | |
| C07K 14/54 | (2006.01) | |
| A61P 35/00 | (2006.01) | |

(52) U.S. Cl.
CPC ............ *A61K 38/179* (2013.01); *A61P 35/00* (2018.01); *C07K 14/5443* (2013.01); *C07K 14/55* (2013.01); *C07K 14/71* (2013.01); *C07K 2319/30* (2013.01)

(58) Field of Classification Search
CPC ... A61K 38/179; A61P 35/00; C07K 14/5443; C07K 14/55; C07K 14/71; C07K 2319/30
See application file for complete search history.

(56) References Cited

U.S. PATENT DOCUMENTS

| 8,283,449 B2 | 10/2012 | Galipeau et al. |
|---|---|---|
| 8,574,548 B2 | 11/2013 | O'Connor-McCourt et al. |
| 2011/0150828 A1 | 6/2011 | Galipeau et al. |
| 2022/0127332 A1 | 4/2022 | Penafuerte Diaz |

FOREIGN PATENT DOCUMENTS

| WO | WO-2009152610 A1 | 12/2009 |
|---|---|---|
| WO | WO-2016200881 A1 | 12/2016 |
| WO | WO-2020047473 A1 | 3/2020 |
| WO | WO-2021041886 A1 | 3/2021 |
| WO | WO-2021096275 A1 | 5/2021 |
| WO | WO-2022086988 A1 | 4/2022 |
| WO | WO-2022178033 A1 | 8/2022 |

OTHER PUBLICATIONS

Cesana et al.: Low-dose interleukin-2 administered pre-operatively to patients with gastric cancer activates peripheral and peritumoral lymphocytes but does not affect prognosis. Annals of surgical oncology. 14(4):1295-1304 (2007) https://doi.org/10.1245/s10434-006-9239-x).
Dammeijer et al.: Rationally combining immunotherapies to improve efficacy of immune checkpoint blockade in solid tumors. Cytokine Growth Factor Rev. 36:5-15 (2017).
Dong et al.: The type III TGF-beta receptor suppresses breast cancer progression. The Journal of clinical investigation. 117(1):206-217 (2007) https://doi.org/10.1172/JCI29293.
Frieman et al.: SARS-CoV pathogenesis is regulated by a STAT1 dependent but a type I, II and III interferon receptor independent mechanism. PLoS Pathog. 6(4):e1000849 (2010).
Heldin et al.: Signaling receptors forTGFBeta famly members. Cold Spring Harbor Perspectives in Biology. doi:10.1101/csjhperspect.a022053. p. 1-33 (2016).
Jamilloux et al.: Should we stimulate or suppress immune responses in COVID-19? Cytokine and anti-cytokine interventions. Autoimmun Rev. 19(7):102567 (2020).
Kint et al.: Infectious Bronchitis Coronavirus Inhibits STAT1 Signaling and Requires Accessory Proteins for Resistance to Type I Interferon Activity. J Virol. 89(23):12047-57 (2015).
Kopecky-Bromberg et al.: Severe acute respiratory syndrome coronavirus open reading frame (ORF) 3b, ORF 6, and nucleocapsid proteins function as interferon antagonists. J Virol. 81(2):548-57 (2007).
Malek et al.: Tolerance, not immunity, crucially depends on IL-2. Nat Rev Immunol. 2004;4(9):665-74.
Marabondo et al.: High-dose interleukin-2 (IL-2) for the treatment of melanoma: safety considerations and future directions. Expert Opin Drug Saf. 16(12):1347-57 (2017).
Massagué, J.: TGFBeta signaling in context. Nat Rev Mol Cell Biol 13:616-630 (2012).
Mendy et al.: Factors Associated with Hospitalization and Disease Severity in a Racially and Ethnically Diverse Population of COVID-19 Patients. medRxiv. (2020).
Muraoka et al.: Blockade of TGF-beta inhibits mammary tumor cell viability, migration, and metastases. The Journal of clinical investigation. 109(12):1551-1559 (2002) https://doi.org/10.1172/JCI15234).
PCT/US2021/055646 International Search Report and Written Opinion dated Jan. 11, 2022.
PCT/US2022/016662 International Search Report and Written Opinion dated May 13, 2022.
Penafuerte al.: Novel TGF-Beta Antagonist Inhibits Tumor Growth and Angiogenesis by Inducing IL-2 Receptor-Driven STAT1 Activation. Journal of Immunology. 186(12):6933-6944 (2011).
Penafuerte et al.: B Effector Cells Activated by a Chimeric Protein Consisting of IL-2 and the Ectodomain of TGF-b Receptor II Induce Potent Antitumor Immunity. Cancer Research. 72(5):1210-1220 (2012).

(Continued)

*Primary Examiner* — Robert S Landsman

(74) *Attorney, Agent, or Firm* — Wilson Sonsini Goodrich & Rosati

(57) ABSTRACT

Provided are multi-functional and multi-valent fusion polypeptides comprising an interleukin polypeptide and two or more TGFβ ligand-binding polypeptides. The compositions and methods provided herein are useful in the application of treating and/or preventing pathogenic infections.

15 Claims, 20 Drawing Sheets

Specification includes a Sequence Listing.

(56) References Cited

OTHER PUBLICATIONS

Penafuerte et al.: FIST, a sword and shield fusokine for cancer immunotherapy. OncoImmunology. 1(2):224-226 (2012).

Rafei et al.: A GMCSF and IL-15 fusokine leads to paradoxical immunosuppression in vivo via asymmetrical JAK/STAT signaling through the IL-15 receptor complex. Blood. 109(5):2234-2242 (2007) https://doi.org/10.1182/blood-2006-07-037473.

Spolski et al.: Biology and regulation of IL-2: from molecular mechanisms to human therapy. Nat Rev Immunol. 18:648-659 (2018).

Stauber et al.: Crystal structure of the IL-2 signaling complex: paradigm for a heterotrimeric cytokine receptor. Proc Natl Acad Sci U S A. 103(8):2788-93 (2006).

Totura et al.: SARS coronavirus pathogenesis: host innate immune responses and viral antagonism of interferon. Curr Opin Virol. 2(3):264-275 (2012).

Tzai et al.: Antisense oligonucleotide specific for transforming growth factor-beta 1 inhibit both in vitro and in vivo growth of MBT-2 murine bladder cancer. Anticancer research. 18(3A):1585-1589 (1998).

U.S. Appl. No. 17/574,479 Office Action dated Jun. 10, 2022.

U.S. Appl. No. 17/574,479 Restriction Requirement dated Apr. 15, 2022.

U.S. Appl. No. 17/574,479 Restriction Requirement dated Mar. 7, 2022.

Wang et al.: An oncolytic adenovirus expressing soluble transforming growth factor-beta type II receptor for targeting breast cancer: in vitro evaluation. Molecular cancer therapeutics. 5(2):367-373 (2006) https://doi.org/10.1158/1535-7163.MCT-05-0125.

Wrangle et al.: IL-2 and Beyond in Cancer Immunotherapy. J Interferon Cytokine Res. 38(2):45-68 (2018).

Yakymovych et al.: Inhibition of transforming growth factor-beta signaling by low molecular weight compounds interfering with ATP- or substrate-binding sites of the TGF beta type I receptor kinase. Biochemistry. 41(36):11000-11007 (2002) https://doi.org/10.1021/bi025936u.

Zhang et al.: Interleukin 2 receptor signaling regulates the perforin gene through signal transducer and activator of transcription (Stat)5 activation of two enhancers. J Exp Med. 190(9):1297-308 (1999).

Zwaagstra et al.: Engineering and therapeutic application of single-chain bivalent TGF-beta family traps. Mol Cancer Ther. 11(7):1477-87 (2012).

Kim et al.: TGF-Beta sensitivity is determined by N-linked glycosylation of the type II TGF-Beta receptor. Biochem J. 445:403-411 (2012).

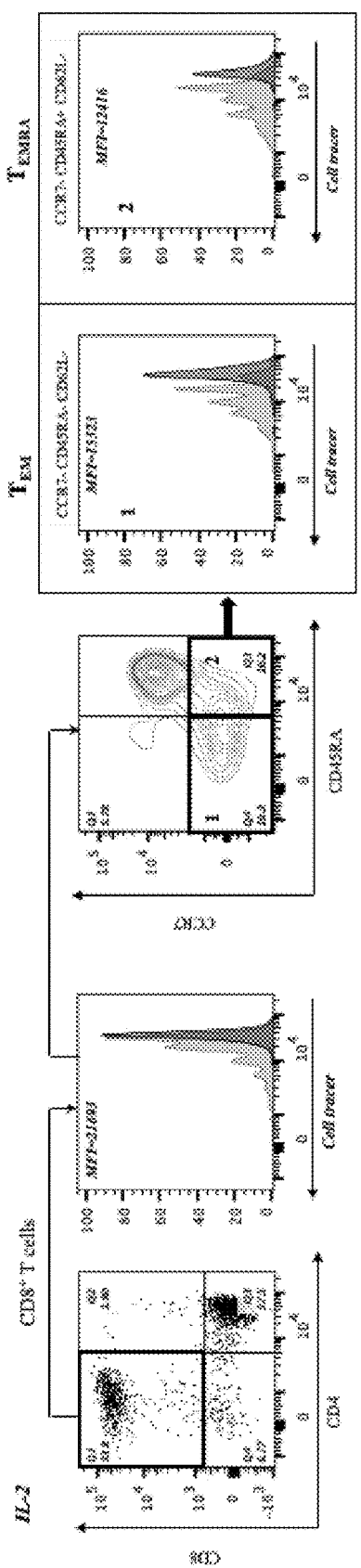
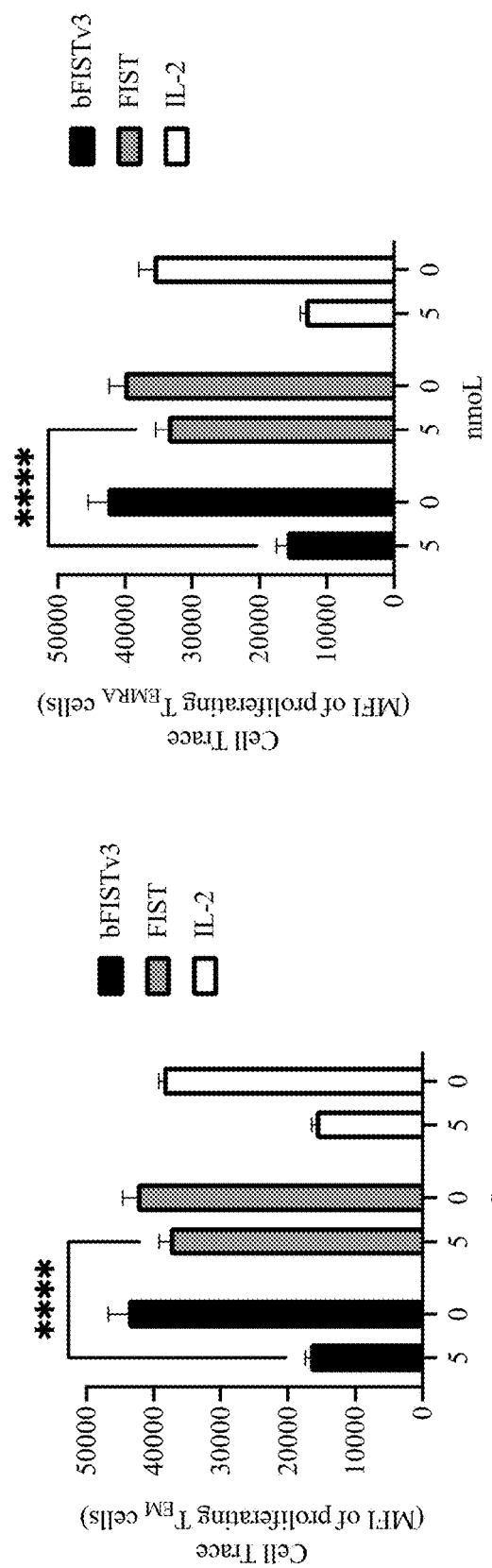
FIG. 6C
FIG. 6D
FIG. 6E

US 11,672,844 B2

METHOD OF TREATING OR AMELIORATING A PATHOGENIC INFECTION BY ADMINISTERING AN INTERLEUKIN-2/TGF-β RECEPTOR FUSION POLYPEPTIDE

CROSS-REFERENCE

This application claims the benefit of U.S. Provisional Application No. 63/150,450 filed on Feb. 17, 2021, which application is incorporated herein by reference.

SEQUENCE LISTING

The instant application contains a Sequence Listing which has been submitted electronically in ASCII format and is hereby incorporated by reference in its entirety. Said ASCII copy, created on Mar. 2, 2022, is named 57949-702_201_SL.txt and is 82,172 bytes in size.

BACKGROUND

Transforming growth factor-β (TGF-β) family or proteins are pleiotropic cytokines that modulate an immune response. TGF-β proteins were originally named for their ability to transform normal fibroblasts to cells capable of anchorage-independent growth. Produced primarily by hematopoietic and tumor cells, TGF-β proteins can regulate (e.g., stimulate or inhibit) the growth and differentiation of cells from a diversity of normal or neoplastic tissue origins. Notably, TGF-β proteins are known to be involved in many proliferative and non-proliferative cellular processes such as, e.g., cell proliferation and differentiation, embryonic development, extracellular matrix formation, bone development, wound healing, hematopoiesis, and immune and inflammatory responses. Increased levels of TGF-β expression and activity are involved in a large number of pathologic conditions, including, but not limited to, aberrant immunosuppression, wherein members of the TGF-β protein family are known to have a number of biological activities related to reducing the efficacy of an immune response.

Interleukins (e.g., IL-2 or IL-15) are potent cytokines that act on the immune system to generate primarily a cell-mediated immune response. For example, IL-2 is locally produced by immune cells at high concentrations near the site of an antigen to supply the necessary costimulatory signals for generating an immune system response to the antigen. IL-2 is therefore an immune-activating molecule and may hold the potential to promote immunotherapeutic responses in treating pathogenic infections (e.g., viral or bacterial infections). For example, in addition to stimulating T cells, IL-2 has also been shown to stimulate lymphocytes (e.g., T cells, B cells, NK cells, NKT cells). However, high doses of IL-2 based therapies have previously been associated with toxicity observed with IL-2 systemic administration. Such deleterious effects present hurdles for the successful utilization of IL-2 as an effective therapeutic.

SUMMARY

Provided herein are fusion proteins that function to activate an immune response and/or inhibit immunosuppressive signaling. This is generally achieved with fusion proteins that comprise an interleukin polypeptide fused (e.g., linked) to two or more polypeptides that inhibit TGFβ activity (e.g., two or more polypeptides that bind to a TGFβ protein). The compositions provided herein are also useful for the inhibition of immunosuppression and/or for activating immune cells. Accordingly, also disclosed herein are methods of inhibiting and/or treating a pathogenic infection (e.g., an intracellular pathogen infection) using the fusion proteins disclosed herein.

Provided are compositions for use in and methods of treating or ameliorating a pathogenic infection in a subject, the method comprising administering to the subject a therapeutically effective amount of a fusion polypeptide comprising: an interleukin (IL) polypeptide; a first TGFβ superfamily receptor polypeptide; and a second TGFβ superfamily receptor polypeptide, thereby treating or ameliorating the pathogenic infection in the subject. Further provided are compositions for use in and methods of treating a pathogenic infection in a subject, the method comprising administering to the subject a therapeutically effective amount of a fusion polypeptide comprising: an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, thereby treating the pathogenic infection in the subject.

Additionally provided are methods of treating or ameliorating fibrosis associated with or resulting from a pathogenic infection (e.g., an intracellular pathogen infection) in a subject, comprising administering a fusion polypeptide comprising: an interleukin (IL) polypeptide; a first TGFβ superfamily receptor polypeptide; and a second TGFβ superfamily receptor polypeptide. Also provided are methods of reducing or inhibiting fibrosis associated with or resulting from a pathogenic infection (e.g., an intracellular pathogen infection) in a subject, comprising administering a fusion polypeptide comprising: an interleukin (IL) polypeptide; a first TGFβ superfamily receptor polypeptide; and a second TGFβ superfamily receptor polypeptide.

In some embodiments, provided is a method of any of the preceding embodiments, wherein the IL polypeptide comprises an IL-2 polypeptide or an IL-15 polypeptide. In some embodiments, provided is a method of any of the preceding embodiments, wherein the IL polypeptide comprises an IL-2 polypeptide. In some embodiments, provided is a method of any of the preceding embodiments, wherein the IL-2 polypeptide comprises SEQ ID NO: 2. In some embodiments, provided is a method of any of the preceding embodiments, wherein the IL-2 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 2. In some embodiments, provided is a method of any of the preceding embodiments, wherein the IL-2 polypeptide consists of SEQ ID NO: 2.

In some embodiments, provided is a method of any of the preceding embodiments, wherein the IL polypeptide comprises an IL-15 polypeptide. In some embodiments, provided is a method of any of the preceding embodiments, wherein the IL-15 polypeptide comprises SEQ ID NO: 4.

In some embodiments, provided is a method of any of the preceding embodiments, wherein the IL-15 polypeptide comprises an amino acid sequence having greater than about 80%, greater than about 85%, greater than about 90%, greater than about 95% greater than about 96%, greater than about 97%, greater than about 98%, or greater than about 99% sequence identity to SEQ ID NO: 5. In some embodiments, provided is a method of any of the preceding embodiments, wherein the IL-15 polypeptide consists of SEQ ID NO: 5.

In some embodiments, provided is a method of any of the preceding embodiments, wherein the first TGFβ superfamily receptor polypeptide, the second TGFβ superfamily receptor polypeptide, or both, comprises an activin receptor polypeptide or fragment thereof, a bone morphogenetic protein (BMP) receptor polypeptide or fragment thereof, a glial cell-derived neurotrophic factor (GDNF) receptor polypeptide or fragment thereof, or a TGFβ receptor II polypeptide or fragment thereof.

In some embodiments, provided is a method of any of the preceding embodiments, wherein the first TGFβ superfamily receptor polypeptide, the second TGFβ superfamily receptor polypeptide, or both, comprises a TGFβ receptor II (TβRII) polypeptide or fragment thereof. In some embodiments, provided is a method of any of the preceding embodiments, wherein the first TGFβ superfamily receptor polypeptide, the second TGFβ superfamily receptor polypeptide, or both, comprises a soluble TGFβ receptor II (TβRII) polypeptide or fragment thereof. In some embodiments, provided is a method of any of the preceding embodiments, wherein the first TGFβ superfamily receptor polypeptide, the second TGFβ superfamily receptor polypeptide, or both, comprises a soluble TGFβ receptor II (TβRII) polypeptide comprising SEQ ID NO: 8, SEQ ID NO: 9, or a combination thereof. In some embodiments, provided is a method of any of the preceding embodiments, wherein the first TGFβ superfamily receptor polypeptide comprises an amino acid sequence of SEQ ID NO: 8 and the second TGFβ superfamily receptor polypeptide comprises a truncation of an amino acid sequence of SEQ ID NO: 9. In some embodiments, provided is a method of any of the preceding embodiments, wherein the soluble TGFβ receptor II polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 8 or 9

In some embodiments, provided is a method of any of the preceding embodiments, wherein the first TGFβ superfamily receptor polypeptide, the second TGFβ superfamily receptor polypeptide, or both, binds a TGF-β1 polypeptide, a TGF-β2 polypeptide, a TGF-β3 polypeptide, a activin βA polypeptide, a activin βB polypeptide, a activin βC polypeptide, a activin βE polypeptide, a bone morphogenic protein (BMP) 2 polypeptide, a BMP 3 polypeptide, a BMP4 polypeptide, a BMP 5 polypeptide, a BMP 6 polypeptide, a BMP 7 polypeptide, a BMP 8 polypeptide, a BMP 9 polypeptide, a BMP 10 polypeptide, a BMP 11 polypeptide, a BMP 12 polypeptide, a BMP 13 polypeptide, a BMP 14 polypeptide, a BMP 15 polypeptide, a growth differentiation factor (GDF) 1 polypeptide, a GDF 3 polypeptide, a GDF 8 polypeptide, a GDF 9 polypeptide, a GDF 15 polypeptide, a Nodal polypeptide, a Inhibin a polypeptide, an anti-Mullerian Hormone polypeptide, a Lefty 1 polypeptide, a Lefty 2 polypeptide, an arteman polypeptide, a Persephin polypeptide, or a Neurturin polypeptide. In some embodiments, provided is a method of any of the preceding embodiments, wherein the first TGFβ superfamily receptor polypeptide, the second TGFβ superfamily receptor polypeptide, or both, binds a TGFβ1 polypeptide, a TGFβ2 polypeptide, a TGFβ3 polypeptide, or any combination thereof. In some embodiments, provided is a method of any of the preceding embodiments, wherein the first TGFβ superfamily receptor polypeptide and the second TGFβ superfamily receptor polypeptide bind a TGFβ1 polypeptide.

In some embodiments, the truncated TGFβ superfamily receptor polypeptide comprises an N terminus truncation, a C terminus truncation, or combination thereof.

In some embodiments, the truncated TGFβ superfamily receptor polypeptide is a truncated soluble TGFβ receptor II (sTβRII) polypeptide. In some embodiments, provided is a method of any of the preceding embodiments, wherein the truncation comprises greater than 2, greater than 5, greater than 7, greater than 10, greater than 15, greater than 20, greater than 25, or greater than 30 amino acids. In some embodiments, provided is a method of any of the preceding embodiments, wherein the IL polypeptide comprises a truncated IL polypeptide.

In some embodiments, truncated IL polypeptide comprises an N terminus truncation, a C terminus truncation, or combination thereof. In some embodiments, provided is a method of any of the preceding embodiments, wherein the truncated IL polypeptide comprises a truncated IL-2 polypeptide or a truncated IL-15 polypeptide.

In some embodiments, provided is a method of any of the preceding embodiments, further comprising a linker polypeptide or a linker molecule attaching the first TGFβ superfamily receptor polypeptide and the second TGFβ superfamily receptor polypeptide. In some embodiments, provided is a method of any of the preceding embodiments, further comprising a linker polypeptide fusing the IL polypeptide and the first TGFβ superfamily receptor polypeptide. In some embodiments, provided is a method of any of the preceding embodiments, further comprising a pharmacokinetic (PK) modulator. In some embodiments, provided is a method of any of the preceding embodiments, wherein the pharmacokinetic modulator comprises an immunoglobulin constant (Fc) region polypeptide. In some embodiments, provided is a method of any of the preceding embodiments, wherein the immunoglobulin Fc region polypeptide is a human immunoglobulin Fc region polypeptide. In some embodiments, provided is a method of any of the preceding embodiments, wherein the immunoglobulin Fc region is an IgG Fc region. In some embodiments, provided is a method of any of the preceding embodiments, wherein the IgG Fc region is an IgG1, IgG2, IgG3, or IgG4 Fc region. In some embodiments, provided is a method of any of the preceding embodiments, wherein the PK modulator comprises an albumin polypeptide. In some embodiments, provided is a method of any of the preceding embodiments, wherein the albumin polypeptide is a human albumin polypeptide.

In some embodiments, provided is a method of any of the preceding embodiments, wherein the fusion polypeptide comprises an amino acid sequence having at least about 80%, at least about 85%, at least about 90%, at least about 95%, at least about 96%, at least about 97%, at least about 98%, or at least about 99% sequence identity to any one of SEQ ID NOs: 10-25. In some embodiments, provided is a method of any of the preceding embodiments, wherein the fusion polypeptide comprises an amino acid sequence of SEQ ID NO: 10. In some embodiments, provided is a method of any of the preceding embodiments, wherein the fusion polypeptide comprises an amino acid sequence of SEQ ID NO: 11. In some embodiments, provided is a method of any of the preceding embodiments, wherein the fusion polypeptide comprises an amino acid sequence of SEQ ID NO: 12. In some embodiments, provided is a method of any of the preceding embodiments, wherein the fusion polypeptide comprises an amino acid sequence of SEQ ID NO: 13. In some embodiments, provided is a method of any of the preceding embodiments, wherein the fusion polypeptide comprises an amino acid sequence of SEQ ID NO: 14.

In some embodiments, the fusion polypeptide comprises an amino acid sequence of SEQ ID NO: 15. In some embodiments, provided is a method of any of the preceding embodiments, the fusion polypeptide comprises an amino acid sequence of SEQ ID NO: 16.

In some embodiments, the fusion polypeptide comprises an amino acid sequence of SEQ ID NO: 17. In some embodiments, provided is a method of any of the preceding embodiments, wherein the fusion polypeptide comprises an amino acid sequence of SEQ ID NO: 18. In some embodiments, provided is a method of any of the preceding embodiments, wherein the fusion polypeptide comprises an amino acid sequence of SEQ ID NO: 19.

In some embodiments, the fusion polypeptide comprises an amino acid sequence of SEQ ID NO: 20.

In some embodiments, the fusion polypeptide comprises an amino acid sequence of SEQ ID NO: 21. In some embodiments, the fusion polypeptide comprises an amino acid sequence of SEQ ID NO: 22. In some embodiments, the fusion polypeptide comprises an amino acid sequence of SEQ ID NO: 23. In some embodiments, the fusion polypeptide comprises an amino acid sequence of SEQ ID NO: 24. In some embodiments, the fusion polypeptide comprises an amino acid sequence of SEQ ID NO: 25. In some embodiments, provided is a method of any of the preceding embodiments, wherein the fusion polypeptide consists of any one of SEQ ID NOs: 10-25.

In some embodiments, provided is a method of any of the preceding embodiments, wherein the fusion polypeptide activates target cells expressing an IL-2 receptor or an IL-15 receptor. In some embodiments, provided is a method of any of the preceding embodiments, wherein the target cell is an immune cell. In some embodiments, provided is a method of any of the preceding embodiments, wherein the immune cell is a T cell, a natural killer cell, an NKT cell, a B cell, or a gamma delta T cell.

In some embodiments, provided is a method of any of the preceding embodiments, wherein the pathogenic infection comprises an intracellular pathogen. In certain embodiments, the intracellular pathogens comprises viruses and/or bacteria. Examples of intracellular bacteria include *Brucella, Legionella pneumophila, Listeria monocytogenes, Mycobacterium leprae, Mycobacterium tuberculosis, Rickettsia rickettsia, Salmonella typhi, Salmonella typhimurium*, etc.

In some embodiments, provided is a method of any of the preceding embodiments, wherein the intracellular bacterial infection comprises is an infection by the genera *Shigella, Campylobacter, Salmonella, Clostridium, Escherichia*, Chlamydiae, Rickettssiaceae, *Coxiella*, Mycobacteriaceae, and combinations thereof. In some embodiments, provided is a method of any of the preceding embodiments, wherein the pathogenic infection is a viral infection. In some embodiments, provided is a method of any of the preceding embodiments, wherein the viral infection comprises a virus from the family denoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. In some embodiments, provided is a method of any of the preceding embodiments, wherein the viral infection comprises coronavirus. In some embodiments, provided is a method of any of the preceding embodiments, wherein the viral infection comprises SARS-COV-2. In some embodiments, provided is a method of any of the preceding embodiments, wherein the viral infection comprises influenza.

Also provided are compositions for use in and methods of neutralizing or inhibiting a pathogen in an individual having a pathogenic infection (e.g., an intracellular pathogen infection), the method comprising administering to the individual a therapeutically effective amount of a fusion polypeptide comprising: an interleukin (IL) polypeptide; a first TGFβ superfamily receptor polypeptide; and a second TGFβ superfamily receptor polypeptide; thereby neutralizing or inhibiting the pathogen in the individual. Further provided are compositions for use in and methods of neutralizing or inhibiting a pathogen in an individual having a pathogenic infection, the method comprising administering to the individual a therapeutically effective amount of a fusion polypeptide comprising: an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, thereby neutralizing or inhibiting the pathogen in the individual.

In some embodiments, provided is a method of any of the preceding embodiments, wherein the IL polypeptide comprises an IL-2 polypeptide or an IL-15 polypeptide. In some embodiments, provided is a method of any of the preceding embodiments, wherein the first TGFβ superfamily receptor polypeptide and the second TGFβ superfamily receptor polypeptide bind a TGFβ 1 polypeptide. In some embodiments, provided is a method of any of the preceding embodiments, wherein the fusion polypeptide comprises an amino acid sequence having at least about 80%, at least about 85%, at least about 90%, at least about 95%, at least about 96%, at least about 97%, at least about 98%, at least about 99%, or 100% sequence identity to any one of SEQ ID NOs: 10-25.

In some embodiments, provided is a method of any of the preceding embodiments, wherein inhibiting or reducing the pathogen comprises activating an immune cell in the individual. In some embodiments, provided is a method of any of the preceding embodiments, wherein the immune cell expresses a receptor for IL-2, IL-15, or both. In some embodiments, provided is a method of any of the preceding embodiments, wherein the immune cell comprises a T cell, a natural killer cell, an NKT cell, a B cell, or a gamma delta T cell. In some embodiments, provided is a method of any of the preceding embodiments, wherein the pathogen comprises an intracellular bacterial infection or a viral infection.

In some embodiments, provided is a method of any of the preceding embodiments, wherein the pathogen is a virus. In some embodiments, provided is a method of any of the preceding embodiments, wherein the virus comprises a virus from the family denoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. In some embodiments, provided is a method of any of the preceding embodiments, wherein the virus comprises coronavirus. In some embodiments, provided is a method of any of the preceding embodiments, wherein the virus comprises SARS-COV-2. In some embodiments, provided is a method of any of the preceding embodiments, wherein the virus comprises influenza.

Provided are compositions for use in and a methods of activating an anti-pathogen immune response cell, the method comprising contacting an immune cell with a fusion polypeptide comprising: an interleukin (IL) polypeptide; a first TGFβ superfamily receptor polypeptide; and a second TGFβ superfamily receptor polypeptide, thereby activating the anti-pathogen immune response cell. Further provided are compositions for use in and methods of activating an anti-pathogen immune response cell, the method comprising contacting an immune cell with a fusion polypeptide comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, thereby activating the anti-pathogen immune response cell.

In some embodiments, provided is a method of any of the preceding embodiments, wherein the IL polypeptide comprises an IL-2 polypeptide or an IL-15 polypeptide. In some embodiments, provided is a method of any of the preceding embodiments, wherein the first TGFβ superfamily receptor polypeptide and the second TGFβ superfamily receptor polypeptide bind a TGFβ 1 polypeptide. In some embodiments, provided is a method of any of the preceding embodiments, wherein the fusion polypeptide comprises an amino acid sequence having at least about 80%, at least about 85%, at least about 90%, at least about 95%, at least about 96%, at least about 97%, at least about 98%, at least about 99%, or 100% sequence identity to any one of SEQ ID NOs: 10-25. In some embodiments, provided is a method of any of the preceding embodiments, wherein the immune cell is in an individual. In some embodiments, provided is a method of any of the preceding embodiments, wherein the immune cell expresses IL-2, IL-15, or both. In some embodiments, provided is a method of any of the preceding embodiments, wherein the immune cell comprises a T cell, a natural killer cell, an NKT cell, a B cell, or a gamma delta T cell.

In some embodiments, provided is a method of any of the preceding embodiments, wherein the pathogen is an intracellular bacterium. In some embodiments, provided is a method of any of the preceding embodiments, wherein the pathogen is a virus. In some embodiments, provided is a method of any of the preceding embodiments, wherein the virus comprises a virus from the family denoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. In some embodiments, provided is a method of any of the preceding embodiments, wherein the virus comprises coronavirus. In some embodiments, provided is a method of any of the preceding embodiments, wherein the virus comprises SARS-COV-2. In some embodiments, provided is a method of any of the preceding embodiments, wherein the virus comprises influenza.

Also provided are uses of a fusion polypeptide comprising an interleukin (IL) polypeptide, a first TGFβ superfamily receptor polypeptide, and a second TGFβ superfamily receptor polypeptide, in a method of neutralizing or inhibiting a virus and/or progression in an individual having a viral infection. Provided are uses of a fusion polypeptide comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, in a method of neutralizing or inhibiting a virus and/or progression in an individual having a viral infection. Further provided are uses of a fusion polypeptide comprising an interleukin (IL) polypeptide, a first TGFβ superfamily receptor polypeptide, and a second TGFβ superfamily receptor polypeptide, in a method of neutralizing or inhibiting an intracellular bacterium and/or progression in an individual having an intracellular bacterial infection.

Further provided are uses of a fusion polypeptide comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, in a method of neutralizing or inhibiting a bacterium and/or progression in an individual having a bacterial infection. Provided are uses of a fusion polypeptide comprising an interleukin (IL) polypeptide, a first TGFβ superfamily receptor polypeptide, and a second TGFβ superfamily receptor polypeptide, in a method of neutralizing or inhibiting an intracellular bacterium and/or progression in an individual having an intracellular bacterial infection. Also provided are uses of a fusion polypeptide comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, in a method of activating an anti-pathogen immune response.

Also provided are methods of reducing or inhibiting fibrosis in an individual, the method comprising administering to the individual a therapeutically effective amount of a fusion polypeptide comprising: (a) an interleukin (IL) polypeptide; (b) a first TGFβ superfamily receptor polypeptide; and (c) a second TGFβ superfamily receptor polypeptide. Further provided are methods of reducing or inhibiting fibrosis resulting from an intracellular pathogen infection in an individual, the method comprising administering to the individual a therapeutically effective amount of a fusion polypeptide comprising: (a) an interleukin (IL) polypeptide; (b) a first TGFβ superfamily receptor polypeptide; and (c) a second TGFβ superfamily receptor polypeptide.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 6A, 6B, 6C, 6D, 6E, and 6F show proliferation of effector memory T cells and terminal differentiated effector memory cells, and the quantification of IFNγ production by stimulated T cells with the bivalent FIST, monovalent FIST, and controls.

DETAILED DESCRIPTION

Figure 1A:
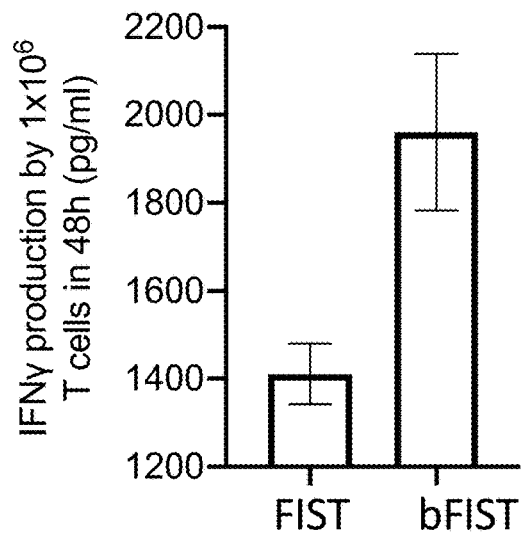
FIGS. 1A and 1B show data depicting the quantification of IFN-gamma production by human T cells previously stimulated by human monovalent FIST (a fusion protein comprising an interleukin-2 (IL-2) polypeptide, a single sTBRII receptor polypeptide) or bivalent FIST (also referred to as bFIST—a fusion polypeptide comprising an interleukin-2 (IL-2) polypeptide, a first sTBRII receptor polypeptide, and a second sTBRII receptor polypeptide), and CXCL10 production by human NK cells stimulated with human FIST (monovalent FIST) or, human bivalent FIST.

Provided herein are multi-functional fusion proteins that are capable of, e.g., activating an immune response, or inhibiting and/or reducing immunosuppressive signaling. In the context of an intracellular pathogenic infection, immune activation is thought to be the physiological function that promotes the recognition and neutralization of a pathogen or pathogen-infected cells. The specific recognition of antigens based on foreignness, molecular weight, complexity, level of expression, and degradability is thought to give rise to the capacities of the immune system to limit pathogen infectivity. In order to activate an immune response and inhibit immunosuppressive signaling, the fusion proteins disclosed herein generally comprise an interleukin polypeptide fused (e.g., linked) to two or more polypeptides that inhibit TGFβ activity (e.g., two or more polypeptides that bind a TGFβ protein). The balance between activating and inhibitory signals is an important factor in maintaining immune homeostasis. In certain instances, immune response to a pathogen encompasses immunostimulatory (e.g., immune activating) signals (e.g., proinflammatory cytokines) that are antagonized by pathogen-induced immunosuppressive signaling molecules (e.g., immunosuppressive cytokines). Among the group of immunosuppressive cytokines thought to be important in driving immunosuppression are members of the TGF superfamily of proteins (e.g., TGFβ).

The TGFβ superfamily includes the TGFβ proteins, Bone Morphogenetic Proteins (BMPs), Growth Differentiation Factors (GDFs), Glial-derived Neurotrophic Factors (GDNFs), Activins, Inhibins, Nodal, Lefty, and Müllerian Inhibiting Substance (MIS). Generally, ligands of the TGFβ superfamily form dimers that bind to heterodimeric receptor complexes consisting of type I and type II receptor subunits with serine/threonine kinase domains.

The TGFβ superfamily of proteins are cytokines thought to be involved in essential cellular functions such as proliferation, differentiation, apoptosis, tissue remodeling, angiogenesis, immune response, and cell adhesion (see, for example, Massagué, J. TGFβ signalling in context. Nat Rev Mol Cell Biol 13, 616-630 (2012)). TGFβ superfamily proteins are also important factors in the pathophysiology of disease states such as chronic inflammatory conditions and fibrosis. The members of this family include the three isoforms of TGFβs: TGFβ1, TGFβ2, and TGFβ3; bone morphogenetic proteins (BMPs); and activins.

The utilization of an interleukin polypeptide (e.g., interleukin-2 or interleukin-15) in the fusion proteins disclosed herein may be useful for activating an immune response in addition to the inhibition of TGFβ. The interleukin family of proteins generally promotes the activation, development, and differentiation of immune cells (e.g., T cells, NK cells, and other lymphocytes), and play essential roles in both innate and adaptive immunity. Accordingly, immune cell activation, development, and differentiation can be achieved by the fusion proteins disclosed herein.

Proinflammatory or immune-stimulating interleukins (e.g., interleukin-2 or interleukin-15) constitute useful adjuvants for activating an immune response. For example, interleukin-2 (IL-2) is a factor for lymphocyte activation and clonal expansion, promoting the activation, development, and differentiation of cytotoxic T cells. IL-2 and IL-15 also stimulate NK cell proliferation and cytotoxicity. However, IL-2 can operate as both an immunostimulatory (e.g., immune-activating) and immunosuppressive agent. As an immunosuppressor, IL-2 maintains peripheral tolerance by inducing the generation of regulatory cells. For these reasons, IL-2 is considered a double-edge sword. The versatility of interleukin function is influenced by the environment and the interaction with signaling agents.

Accordingly, the fusion proteins disclosed herein are multi-functional in that the fusion proteins are useful for immune activation, the inhibition of immunosuppression and tissue fibrosis. As disclosed herein, the activation of an immune response and inhibition of an immunosuppressive response may be, at least in part, achieved by the interleukin polypeptide. In turn, the inhibition or reduction of an immunosuppressive signaling and/or inhibition of tissue fibrosis may be achieved, at least in part, through the use of one or more polypeptides that inhibit activity of TGFβ proteins.

As used herein, the term "fusion protein" generally refers to a protein that includes polypeptide components derived from more than one parental protein or polypeptide. Generally, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

A "domain" of a protein, as used herein, generally is any portion of the entire protein, up to and including the complete protein, but typically comprising less than the complete protein. A domain can, but need not, fold independently of the rest of the protein chain and/or be correlated with a particular biological, biochemical, or structural function or location (e.g., a ligand binding domain, or a cytosolic, transmembrane, or extracellular domain).

The term "recombinant" indicates that the material (e.g., a nucleic acid or a polypeptide) has been artificially or synthetically (e.g., non-naturally) altered by human intervention. The alteration can be performed on the material within, or removed from, its natural environment or state. For example, a "recombinant nucleic acid" is one that is made by recombining nucleic acids, e.g., during cloning, DNA shuffling, or other well-known molecular biological procedures. A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid.

A "polynucleotide sequence" or "nucleotide sequence" or "nucleic acid sequence," as used interchangeably herein, is a polymer of nucleotides, including an oligonucleotide, a DNA, an RNA, a nucleic acid, or a character string representing a nucleotide polymer, depending on context. From any specified polynucleotide sequence, either the given nucleic acid or the complementary polynucleotide sequence can be determined. Included are DNA or RNA of genomic or synthetic origin which may be single- or double-stranded, and represent the sense or antisense strand.

As used herein, the terms "nucleic acid molecule encoding," "DNA sequence encoding," "nucleic acid sequence encoding" or "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (or protein) chain. The DNA sequence thus codes for the RNA sequence and for the amino acid sequence.

"Expression of a gene" or "expression of a nucleic acid" means transcription of DNA into RNA (optionally including modification of the RNA, e.g., splicing), translation of RNA into a polypeptide (optionally including subsequent post-translational modification of the polypeptide), or both transcription and translation, as indicated by the context.

The term "gene" is used broadly to refer to any nucleic acid associated with a biological function. Genes typically include coding sequences and/or the regulatory sequences required for expression of such coding sequences. The term "gene" applies to a specific genomic or recombinant sequence, as well as to a cDNA or mRNA encoded by that sequence. A "fusion gene" contains a coding region that encodes a transgene. Genes also include non-expressed nucleic acid segments that, for example, form recognition sequences for other proteins. Non-expressed regulatory sequences include transcriptional control elements to which regulatory proteins, such as transcription factors, bind, resulting in transcription of adjacent or nearby sequences.

As used herein the term "coding region" or "coding sequence" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (e.g., TAA, TAG, TGA). Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect, and mammalian cells, and viruses (analogous control elements, e.g., promoters, are also found in prokaryotes). The selection of a particular promoter and enhancer depends on what cell type is to be used to express the protein of interest. Some eukaryotic promoters and enhancers have a broad host range while others are functional in a limited subset of cell types.

The term "expression vector" refers to a recombinant DNA molecule containing a desired coding sequence and appropriate nucleic acid sequences necessary for the expression of the operably linked coding sequence in a particular host cell. Nucleic acid sequences necessary for expression in prokaryotes include a promoter, optionally an operator sequence, a ribosome binding site, and optionally other sequences. Eukaryotic cells are known to utilize promoters, enhancers, and termination and polyadenylation signals. A secretory signal peptide sequence can also, optionally, be encoded by the expression vector, operably linked to the coding sequence for a peptide analog, so that the expressed peptide can be secreted by the recombinant host cell, e.g., for more facile isolation of the peptide from the cell, if desired.

Interleukins

The fusion proteins provided herein generally comprise an interleukin polypeptide fused (e.g., linked) to two or more polypeptides that inhibit TGFβ activity (e.g., two or more polypeptides that bind a TGFβ protein). Interleukins (ILs) are a class of cytokines first thought to be expressed by leukocytes alone but have later been found to be produced by many other body cells. Interleukins are thought to play important roles in, e.g., the activation and differentiation of immune cells, as well as cell proliferation, maturation, migration, and adhesion. The function of interleukins is, therefore, thought to be to modulate growth, differentiation, and activation during inflammatory and immune responses. Accordingly, the interleukin polypeptide of the fusion protein may be useful for the regulation (e.g., activation) of an immune response.

Interleukin-2 (IL-2) is a pleiotropic cytokine that is induced by antigen stimulation and thus plays a significant role in regulating the immune response (see, for example, Spolski, R., Li, P. & Leonard, W. J. Biology and regulation of IL-2: from molecular mechanisms to human therapy. Nat Rev Immunol 18, 648-659 (2018)). For example, IL-2 can promote a pathogen clearing response due to its effectiveness at inducing an immune response, acting as an autocrine factor for T cells and supporting the development of cytotoxic T cells, stimulating NK cells proliferation and cytolytic activity. Accordingly, in some instances, Interleukin-2 (IL-2) can be useful for activating the immune response in the context of a fusion protein comprising an interleukin polypeptide fused (e.g., linked) to two or more polypeptides that inhibit TGFβ activity.

IL-2 is a small, 15.5-kDa four α-helical bundle cytokine. It is produced predominately by antigen stimulated CD4+ T cells, while it can also be produced by CD8+ cells, natural killer (NK) cells, and activated dendritic cells (DC). IL-2 is an important factor for the maintenance of CD4+ regulatory T cells and plays a critical role in the differentiation of CD4+ T cells into a variety of T cell subsets. It can promote CD8+ T-cell and NK cell cytotoxicity activity, and modulate T-cell differentiation programs in response to antigen, promoting naive CD4+ T-cell differentiation into T helper-1 (Th1) and T helper-2 (Th2) cells while inhibiting T helper-17 (Th17) differentiation. Notably, IL-2 was one of the first FDA-approved immunotherapy drugs for metastatic melanoma and renal cell cancer. However, IL-2 immunotherapy has not been widely applied due to its short half-life in vivo and severe toxicity at the therapeutic dosage.

In an aspect, interleukin-2 or IL-2 generally includes any native IL-2 from any vertebrate source, including mammals such as primates (e.g., humans) and rodents (e.g., mice and rats), unless otherwise indicated. IL-2 includes unprocessed IL-2 as well as any form of IL-2 that results from processing in the cell. The term also encompasses naturally occurring variants of IL-2, e.g., splice variants or allelic variants. The amino acid sequence of an exemplary human IL-2 is shown in SEQ ID NO: 1. Unprocessed human IL-2 additionally comprises an N-terminal 20 amino acid signal peptide, which is absent in the mature IL-2 molecule. IL-2 also includes "wild-type IL-2" or a naturally occurring IL-2. The sequence of a native human IL-2 molecule is shown in SEQ ID NO: 1. For the purpose of the present disclosure, the term wild-type also encompasses forms of IL-2 comprising one or more amino acid mutations. For example, the fusion proteins described herein can comprise an IL-2 polypeptide having greater than 80%, greater than 85%, greater than 90%, greater than 95%, greater than 96%, greater than 97%, greater than 98%, or greater than 99% sequence identity to the amino acid sequence of SEQ ID NO: 1.

In some embodiments, the fusion protein comprises an IL-2 sequence comprising an amino acid sequence having about 85% to about 100% sequence identity to SEQ ID NO: 1. In some embodiments, the fusion protein comprises an IL-2 sequence comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 1. In some embodiments, the fusion protein comprises an IL-2 sequence comprising an amino acid sequence having about 85%, about 90%, about 95%, about 96%, about 97%, about 98%, about 99%, or about 100% sequence identity to SEQ ID NO: 1. In some embodiments, the fusion protein comprises an IL-2 sequence comprising an amino acid sequence having at least about 85%, at least about 90%, at least about 95%, at least about 96%, at least about 97%, at least about 98%, or at least about 99% sequence identity to SEQ ID NO: 1.

The IL-2 polypeptide can comprise a full-length native sequence or truncations thereof. In some embodiments, the IL-2 polypeptide is a truncated IL-2 polypeptide. The truncated IL-2 polypeptide can comprise N-terminus truncations, C-terminus truncations, or a combination thereof. In some embodiments, the fusion protein comprises an IL-2 polypeptide that is truncated by about 2 amino acids to about 20 amino acids (e.g., relative to a full-length IL-2 polypeptide). In some embodiments, the fusion protein comprises an IL-2 polypeptide that is truncated by about 2 amino acids to about 5 amino acids, about 2 amino acids to about 7 amino acids, about 2 amino acids to about 8 amino acids, about 2 amino acids to about 10 amino acids, about 2 amino acids to about 15 amino acids, about 2 amino acids to about 20 amino acids, about 5 amino acids to about 7 amino acids, about 5 amino acids to about 8 amino acids, about 5 amino acids to about 10 amino acids, about 5 amino acids to about 15 amino acids, about 5 amino acids to about 20 amino acids, about 7 amino acids to about 8 amino acids, about 7 amino acids to about 10 amino acids, about 7 amino acids to about 15 amino acids, about 7 amino acids to about 20 amino acids, about 8 amino acids to about 10 amino acids, about 8 amino acids to about 15 amino acids, about 8 amino acids to about 20 amino acids, about 10 amino acids to about 15 amino acids, about 10 amino acids to about 20 amino acids, or about 15 amino acids to about 20 amino acids (e.g., relative to a full-length IL-2 polypeptide). In some embodiments, the fusion protein comprises an IL-2 polypeptide that is truncated by about 2 amino acids, about 5 amino acids, about 7 amino acids, about 8 amino acids, about 10 amino acids, about 15 amino acids, or about 20 amino acids (e.g., relative to a full-length IL-2 polypeptide). In some embodiments, the fusion protein comprises an IL-2 polypeptide that is truncated by at least about 2 amino acids, at least about 5 amino acids, at least about 7 amino acids, at least about 8 amino acids, at least about 10 amino acids, or at least about 15 amino acids (e.g., relative to a full-length IL-2 polypeptide). In some embodiments, the fusion protein comprises an IL-2 polypeptide that is truncated by at most about 5 amino acids, at most about 7 amino acids, at most about 8 amino acids, at most about 10 amino acids, at most about 15 amino acids, or at most about 20 amino acids (e.g., relative to a full-length IL-2 polypeptide). In some embodiments, the fusion protein comprises an IL-2 polypeptide having an amino acid sequence of SEQ ID NO: 2.

In some embodiments, the fusion protein comprises an IL-2 polypeptide comprising an amino acid sequence having about 85% to about 100% sequence identity to SEQ ID NO: 2. In some embodiments, the fusion protein comprises an IL-2 polypeptide comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 2. In some embodiments, the fusion protein comprises an IL-2 polypeptide comprising an amino acid sequence having about 85%, about 90%, about 95%, about 96%, about 97%, about 98%, about 99%, or about 100% sequence identity to SEQ ID NO: 2. In some embodiments, the fusion protein comprises an IL-2 polypeptide comprising an amino acid sequence having at least about 85%, at least about 90%, at least about 95%, at least about 96%, at least about 97%, at least about 98%, or at least about 99% sequence identity to SEQ ID NO: 2.

Interleukin-15 (IL-15) is also an interleukin useful for activating the immune response in the context of a fusion protein provided herein. Interleukin 15 (IL-15) is a cytokine of about 12-14 kilodaltons comprising a four-α-helix structure. IL-15 belongs to the family of cytokines consisting of interleukins IL-2, IL-4, IL-7, IL-9, and IL-21. IL-15 signals through a receptor complex composed of the IL-2/IL-15 receptor β (IL-15Rβ) (CD122) subunit, which is shared with IL-2 and the common gamma chain (γC) (CD132) receptor subunit, which is also utilized by all of the additional family members. Notably, IL-15 is a growth factor for T cells and NK cells, and plays an important role in the development, proliferation, and activation of these immune cells. Although IL-15 has a potential for therapeutic use, natural IL-15 has therapeutic development issues, namely a low biological potency and a short half-life.

The term "interleukin-15" or "IL-15" refers to any native IL-15 from any vertebrate source, including mammals such as primates (e.g., humans) and rodents (e.g., mice and rats), unless otherwise indicated. IL-15 includes unprocessed IL-15 as well as any form of IL-15 that results from processing in the cell. The term also encompasses naturally occurring variants of IL-15, e.g., splice variants or allelic variants. The amino acid sequence of an exemplary human IL-15 is shown in SEQ ID NO: 4 IL-15 also includes "wild-type IL-15" or a naturally occurring IL-15. The sequence of a native human IL-15 molecule is shown in SEQ ID NO: 4. For the purpose of the present disclosure, the term wild-type IL-15 also encompasses forms of IL-15 comprising one or more amino acid mutations. For example, the fusion proteins described herein can comprise an IL-15 polypeptide comprising an amino acid sequence having greater than 80%, greater than 85%, greater than 90% greater than 95%, greater than 96%, greater than 97%, greater than 98%, or greater than 99% sequence identity to the amino acid sequence of SEQ ID NO: 4.

In some embodiments, the fusion protein comprises an IL-15 polypeptide comprising an amino acid sequence having about 85% to about 100% sequence identity to SEQ ID NO: 4. In some embodiments, the fusion protein comprises an IL-15 polypeptide comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 4. In some embodiments, the fusion protein comprises an IL-15 polypeptide comprising an amino acid sequence having about 85%, about 90%, about 95%, about 96%, about 97%, about 98%, about 99%, or about 100% sequence identity to SEQ ID NO: 4. In some embodiments, the fusion protein comprises an IL-15 polypeptide comprising an amino acid sequence having at least about 85%, at least about 90%, at least about 95%, at least about 96%, at least about 97%, at least about 98%, or at least about 99% sequence identity to SEQ ID NO: 4.

The IL-15 polypeptide can comprise a full-length native sequence or truncations thereof. In some embodiments, the IL-15 polypeptide is a truncated IL-15 polypeptide. The truncated IL-15 polypeptide can comprise N-terminus truncations, C-terminus truncations, or a combination thereof. In some embodiments, the fusion protein comprises an IL-15 polypeptide that is truncated by about 2 amino acids to about 20 amino acids (e.g., relative to a full-length IL-15 polypeptide). In some embodiments, the fusion protein comprises an IL-15 polypeptide that is truncated by about 2 amino acids to about 5 amino acids, about 2 amino acids to about 7 amino acids, about 2 amino acids to about 8 amino acids, about 2 amino acids to about 10 amino acids, about 2 amino acids to about 15 amino acids, about 2 amino acids to about 20 amino acids, about 5 amino acids to about 7 amino acids, about 5 amino acids to about 8 amino acids, about 5 amino acids to about 10 amino acids, about 5 amino acids to about 15 amino acids, about 5 amino acids to about 20 amino acids, about 7 amino acids to about 8 amino acids, about 7 amino acids to about 10 amino acids, about 7 amino acids to about 15 amino acids, about 7 amino acids to about 20 amino acids, about 8 amino acids to about 10 amino acids, about 8 amino acids to about 15 amino acids, about 8 amino acids to about 20 amino acids, about 10 amino acids to about 15 amino acids, about 10 amino acids to about 20 amino acids, or about 15 amino acids to about 20 amino acids (e.g., relative to a full-length IL-15 polypeptide). In some embodiments, the fusion protein comprises an IL-15 polypeptide that is truncated by about 2 amino acids, about 5 amino acids, about 7 amino acids, about 8 amino acids, about 10 amino acids, about 15 amino acids, or about 20 amino acids (e.g., relative to a full-length IL-15 polypeptide). In some embodiments, the fusion protein comprises an IL-15 polypeptide that is truncated by at least about 2 amino acids, at least about 5 amino acids, at least about 7 amino acids, at least about 8 amino acids, at least about 10 amino acids, or at least about 15 amino acids (e.g., relative to a full-length IL-15 polypeptide). In some embodiments, the fusion protein comprises an IL-15 polypeptide that is truncated by at most about 5 amino acids, at most about 7 amino acids, at most about 8 amino acids, at most about 10 amino acids, at most about 15 amino acids, or at most about 20 amino acids (e.g., relative to a full-length IL-15 polypeptide). In some embodiments, the fusion protein comprises an IL-15 polypeptide having an amino acid sequence of SEQ ID NO: 5.

In some embodiments, the fusion protein comprises an IL-15 polypeptide comprising an amino acid sequence having about 85% to about 100% sequence identity to SEQ ID NO: 5. In some embodiments, the fusion protein comprises an IL-15 polypeptide comprising an amino acid sequence about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 9900, about 96% to about 100%, about 97% to about 98%, about 97% to about 99%, about 97% to about 100%, about 98% to about 99%, about 98% to about 100%, or about 99% to about 100% having sequence identity to SEQ ID NO: 5. In some embodiments, the fusion protein comprises an IL-15 polypeptide comprising an amino acid sequence having about 85%, about 90%, about 95%, about 96%, about 97%, about 98%, about 99%, or about 100% sequence identity to SEQ ID NO: 5. In some embodiments, the fusion protein comprises an IL-15 polypeptide comprising an amino acid sequence having at least about 85%, at least about 90%, at least about 95%, at least about 96%, at least about 97%, at least about 98%, or at least about 99% sequence identity to SEQ ID NO: 5.

TGFβ Inhibiting Polypeptides

As described herein, the fusion proteins provided herein generally comprise an interleukin polypeptide (e.g., IL-2 or IL-15) fused (e.g., linked) to two or more polypeptides that inhibit TGFβ activity (e.g., two or more polypeptides that bind a TGFβ protein). The transforming growth factor β (TGFβ) superfamily is a large group of soluble factors (e.g., proteins) that initiate and control activation, proliferation, and differentiation of many cell types, thus playing important roles in embryonal development and homeostasis. The TGFβ superfamily includes several subfamilies: the activin/inhibin family, bone morphogenetic proteins (BMPs), growth differentiation factors (GDFs), the TGFβ subfamily, and glial cell line-derived neurotrophic factor (GDNF) family. TGFβ superfamily has three types: TGFβ1, TGFβ2, and TGFβ3. TGFβ superfamily proteins have been discovered in a variety of species, including invertebrates as well as vertebrates. TGFβ malfunction can lead to developmental disorders, severe defects in organ function, and is associated with several diseases.

The inhibition and suppression of TGFβ superfamily activity can be achieved through the use of fusion proteins comprising, in addition to an interleukin polypeptide, two or more TGFβ superfamily receptor polypeptides. In the context of the fusion proteins described herein, the two or more TGFβ superfamily receptor polypeptides yield a multivalent single chain polypeptide capable of binding two or more TGFβ proteins. Generally, ligands of the TGFβ superfamily bind to receptor complexes consisting of type I and type II receptor subunits. As disclosed herein, polypeptides derived from TGFβ superfamily receptors are useful for inhibiting or suppressing TGFβ superfamily ligands. For example, in some embodiments, the TGFβ superfamily receptor is selected from the group consisting of: an activin receptor polypeptide or fragment thereof, a bone morphogenetic protein (BMP) receptor polypeptide or fragment thereof, a glial cell-derived neurotrophic factor (GDNF) receptor polypeptide or fragment thereof, and a TGFβ receptor polypeptide or fragment thereof.

Within the TGFβ superfamily of proteins, the TGFβ sub-family of proteins comprises TGFβ1, TGFβ2, and TGFβ3. Among TGFβs, TGFβ1 is the most potent immunosuppressive cytokine described to date, and exerts deleterious effects (e.g., immunosuppression) on several components of the immune system response against pathogens. Notably, TGFβ proteins (e.g., TGFβ1) diminish or reduce the effector functions of macrophages, B cells, cytotoxic T cells, dendritic cells, and NK cells, where TGFβ acts as a negative regulator of IFNγ production via its mediators SMAD2, SMAD3, and SMAD4.

Most cell types express three sizes of receptors for TGFβ, designated Type 1 (53 kDa), Type II (70-85 kDa), and Type III (250-350 kDa). The Type I receptor is a membrane-bound serine/threonine kinase that apparently requires the presence of the Type II receptor to bind TGFβ. The Type II receptor is also a membrane-bound serine/threonine kinase that binds TGFβ1 and TGFβ3 with high affinity and TGFβ2 with much lower affinity. The Type I and Type II receptors together form a heterodimeric signaling complex that is essential for the transduction of the anti-proliferative signals of TGFβ. The Type III receptor is a transmembrane proteoglycan with a large extracellular domain and a 43 amino acid residue cytoplasmic domain. The cytoplasmic domain of the Type III receptor lacks an obvious signaling motif and the receptor may not be involved directly in signal transduction. Notably, the soluble extracellular domain of the TβRII, consisting of the extracellular domain of the receptor binds TGF-β1 and TGF-β3 with high affinity.

Accordingly, the TGFβ receptor TβRII polypeptides are useful in TGFβ binding polypeptides of the multi-functional fusion proteins described herein. Particularly, TGFβ receptor TβRII polypeptides are useful for inhibiting or reducing TGFβ1 activity or signaling associated therewith. The term "soluble transforming growth factor (TGF) β receptor type II B" or "sTβRII" as used herein refers to a soluble, or non-membrane form of the alternatively spliced transforming growth factor β type II receptor, preferably the ectodomain of the TGFβ type II receptor from any species or source and includes the full-length ectodomain as well as fragments or portions of the ectodomain. In some embodiments, the sTβRIIB is human or mouse. The human TGFβ receptor II has the amino acid sequence of SEQ ID NOs: 6 or 7 (short and long isoforms, respectively). The term "sTβRII fragment" as used herein means at least about 10%, at least about 20%, at least about 30%, at least about 40%, at least about 50%, at least about 60%, at least about 70%, at least about 80%, at least about 90%, at least about 95%, or more of the entire length of the reference polypeptide. In one embodiment, the polypeptide is truncated at the N-terminal or C-terminal end to permit cloning.

In some embodiments, the fusion protein comprises an sTβRII polypeptide comprising an amino acid sequence having about 85% to about 100% sequence identity to SEQ ID NO: 6. In some embodiments, the fusion protein comprises an sTβRII polypeptide comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 6. In some embodiments, the fusion protein comprises an sTβRII polypeptide comprising an amino acid sequence having about 85%, about 90%, about 95%, about 96%, about 97%, about 98%, about 99%, or about 100% sequence identity to SEQ ID NO: 6. In some embodiments, the fusion protein comprises an sTβRII polypeptide comprising an amino acid sequence having at least about 85%, about 90%, about 95%, about 96%, about 97%, about 98%, or about 99% sequence identity to SEQ ID NO: 6.

In some embodiments, the fusion protein comprises an sTβRII polypeptide comprising an amino acid sequence having about 85% to about 100% sequence identity to SEQ ID NO: 7. In some embodiments, the fusion protein comprises an sTβRII polypeptide comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 6. In some embodiments, the fusion protein comprises an sTβRII polypeptide comprising an amino acid sequence having about 85%, about 90%, about 95%, about 96%, about 97%, about 98%, about 99%, or about 100% sequence identity to SEQ ID NO: 7. In some embodiments, the fusion protein comprises an sTβRII polypeptide comprising an amino acid sequence having at least about 85%, at least about 90%, at least about 95%, at least about 96%, at least about 97%, at least about 98%, or at least about 99% sequence identity to SEQ ID NO: 7.

As described herein, the two or more sTβRII receptor polypeptides utilize the ectodomain of a native sTβRII receptor. Accordingly, the sTβRII receptor polypeptide used herein comprises SEQ ID NO: 8 (e.g., the short isoform of sTβRII), SEQ ID NO: 9 (e.g., the long isoform of sTβRII), or a combination thereof.

In some embodiments, the fusion protein comprises an sTβRII polypeptide comprising an amino acid sequence having about 85% to about 100% sequence identity to SEQ ID NO: 8. In some embodiments, the fusion protein comprises an sTβRII polypeptide comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 8. In some embodiments, the fusion protein comprises an sTβRII polypeptide comprising an amino acid sequence having about 85%, about 90%, about 95%, about 96%, about 97%, about 98%, about 99%, or about 100% sequence identity to SEQ ID NO: 8. In some embodiments, the fusion protein comprises an TβRII polypeptide comprising an amino acid sequence having at least about 85%, at least about 90%, at least about 95%, at least about 96%, at least about 97%, at least about 98%, or at least about 99% sequence identity to SEQ ID NO: 8.

In some embodiments, the fusion protein comprises an sTβRII polypeptide comprising an amino acid sequence having about 85% to about 100% sequence identity to SEQ ID NO: 9. In some embodiments, the fusion protein comprises an sTβRII polypeptide comprising an amino acid sequence having about 85% to about 90%, about 85% to about 95%, about 85% to about 96%, about 85% to about 97%, about 85% to about 98%, about 85% to about 99%, about 85% to about 100%, about 90% to about 95%, about 90% to about 96%, about 90% to about 97%, about 90% to about 98%, about 90% to about 99%, about 90% to about 100%, about 95% to about 96%, about 95% to about 97%, about 95% to about 98%, about 95% to about 99%, about 95% to about 100%, about 96% to about 97%, about 96% to about 98%, about 96% to about 99%, about 96% to about 100%, about 97% to about 98%, about 97% to about 99%, about 97% to about 100%, about 98% to about 99%, about 98% to about 100%, or about 99% to about 100% sequence identity to SEQ ID NO: 9. In some embodiments, the fusion protein comprises an sTβRII polypeptide comprising an amino acid sequence having about 85%, about 90%, about 95%, about 96%, about 97%, about 98%, about 99%, or about 100% sequence identity to SEQ ID NO: 9. In some embodiments, the fusion protein comprises an TβRII polypeptide comprising an amino acid sequence having at least about 85%, at least about 90%, at least about 95%, at least about 96%, at least about 97%, at least about 98%, or at least about 99% sequence identity to SEQ ID NO: 9.

The sTβRII polypeptide of SEQ ID NO: 8 or SEQ ID NO: 9 can comprise additional truncations thereof. In some embodiments, the sTβRII polypeptide is a truncated sTβRII polypeptide. The truncated sTβRII polypeptide can comprise N-terminus truncations, C-terminus truncations, or a combination thereof. In some embodiments, the fusion protein comprises an sTβRII that is truncated by about 2 amino acids to about 20 amino acids (e.g., relative to a full-length sTβRII polypeptide). In some embodiments, the fusion protein comprises an sTβRII that is truncated by about 2 amino acids to about 5 amino acids, about 2 amino acids to about 7 amino acids, about 2 amino acids to about 8 amino acids, about 2 amino acids to about 10 amino acids, about 2 amino acids to about 15 amino acids, about 2 amino acids to about 20 amino acids, about 5 amino acids to about 7 amino acids, about 5 amino acids to about 8 amino acids, about 5 amino acids to about 10 amino acids, about 5 amino acids to about 15 amino acids, about 5 amino acids to about 20 amino acids, about 7 amino acids to about 8 amino acids, about 7 amino acids to about 10 amino acids, about 7 amino acids to about 15 amino acids, about 7 amino acids to about 20 amino acids, about 8 amino acids to about 10 amino acids, about 8 amino acids to about 15 amino acids, about 8 amino acids to about 20 amino acids, about 10 amino acids to about 15 amino acids, about 10 amino acids to about 20 amino acids, or about 15 amino acids to about 20 amino acids (e.g., relative to a full-length sTβRII polypeptide). In some embodiments, the fusion protein comprises an sTβRII that is truncated by about 2 amino acids, about 5 amino acids, about 7 amino acids, about 8 amino acids, about 10 amino acids, about 15 amino acids, or about 20 amino acids. In some embodiments, the fusion protein comprises an sTβRII that is truncated by at least about 2 amino acids, at least about 5 amino acids, at least about 7 amino acids, at least about 8 amino acids, at least about 10 amino acids, or at least about 15 amino acids. In some embodiments, the fusion protein comprises an sTβRII that is truncated by at most about 5 amino acids, at most about 7 amino acids, at most about 8 amino acids, at most about 10 amino acids, at most about 15 amino acids, or at most about 20 amino acids (e.g., relative to a full-length sTβRII polypeptide).

Multi-Functional and Multi-Valent Fusion Protein Compositions

Provided herein are fusion polypeptides comprising: (a) an interleukin (IL) polypeptide; (b) a first TGFβ superfamily receptor polypeptide; and (c) a second TGFβ superfamily receptor polypeptide. Also provided herein are fusion polypeptides comprising: a first IL polypeptide that binds to and agonizes the IL receptor; a second polypeptide that binds to and sequesters soluble TGFβ; and a third polypeptide that binds to and sequesters soluble TGFβ.

In some embodiments, the IL polypeptide is IL-2. In some embodiments, the IL polypeptide is IL-15. In certain embodiments the IL-2 polypeptide comprises SEQ ID NO: 2 or 3. In certain embodiments the IL-2 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 2 or 3. In certain embodiments, the IL-15 polypeptide comprises SEQ ID NO: 4 or 5. In certain embodiments, the IL-15 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 4 or 5. In certain embodiments, the IL polypeptide is a truncated polypeptide.

In some embodiments, the first TGFβ superfamily receptor polypeptide and/or the second TGFβ superfamily receptor polypeptide comprises a soluble TGFβ receptor II polypeptide. In some embodiments, the first TGFβ superfamily receptor polypeptide and the second TGFβ superfamily receptor polypeptide comprises a soluble TGFβ receptor II polypeptide comprising SEQ ID NO: 8, SEQ ID NO: 9, or a combination thereof. In some embodiments, the first TGFβ superfamily receptor polypeptide comprises an amino acid sequence of SEQ ID NO: 8 and the second TGFβ superfamily receptor polypeptide comprises a truncation of an amino acid sequence of SEQ ID NO: 9. In certain embodiments, the soluble TGFβ receptor II polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 8 or SEQ ID NO: 9.

In another embodiment, the second polypeptide that binds to and sequesters soluble TGFβ and/or the third polypeptide that binds to and sequesters soluble TGFβ comprises a soluble TGFβ receptor II polypeptide. In some embodiments, the second polypeptide that binds to and sequesters soluble TGFβ and/or the third polypeptide that binds to and sequesters soluble TGFβ comprises a soluble TGFβ receptor II polypeptide comprising SEQ ID NO: 8, SEQ ID NO: 9, or a combination thereof. In certain embodiments, the soluble TGFβ receptor II polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 8 or SEQ ID NO: 9.

In some embodiments, the first TGFβ superfamily receptor polypeptide and/or the second TGFβ superfamily receptor polypeptide target a TGF-β1 polypeptide, a TGF-β2 polypeptide, a TGF-β3 polypeptide, a activin βA polypeptide, a activin βB polypeptide, a activin βC polypeptide, a activin βE polypeptide, a bone morphogenic protein (BMP) 2 polypeptide, a BMP 3 polypeptide, a BMP4 polypeptide, a BMP 5 polypeptide, a BMP 6 polypeptide, a BMP 7 polypeptide, a BMP 8 polypeptide, a BMP 9 polypeptide, a BMP 10 polypeptide, a BMP 11 polypeptide, a BMP 12 polypeptide, a BMP 13 polypeptide, a BMP 14 polypeptide, a BMP 15 polypeptide, a growth differentiation factor (GDF) 1 polypeptide, a GDF 3 polypeptide, a GDF 8 polypeptide, a GDF 9 polypeptide, a GDF 15 polypeptide, a Nodal polypeptide, a Inhibin a polypeptide, an anti-Mullerian Hormone polypeptide, a Lefty 1 polypeptide, a Lefty 2 polypeptide, an arteman polypeptide, a Persephin polypeptide, or a Neurturin polypeptide. In some embodiments, the first TGFβ superfamily receptor polypeptide and/or the second TGFβ superfamily receptor polypeptide binds a TGFβ1 polypeptide, a TGFβ2 polypeptide, a TGFβ3 polypeptide, or any combination thereof. In some embodiments, the first TGFβ superfamily receptor polypeptide and/or the second TGFβ superfamily receptor polypeptide binds a TGFβ1 polypeptide.

In another embodiment, the second polypeptide and/or the third polypeptide binds to and sequesters a TGFβ1 polypeptide, a TGFβ2 polypeptide, a TGFβ3 polypeptide, or any combination thereof. In certain embodiments, the second polypeptide and/or the third polypeptide binds to and sequesters a TGFβ1 polypeptide.

A polypeptide of the fusion polypeptide can be "fused" or "linked" via a linker. The linker may be a polypeptide linker or other linker of suitable flexibility so as not to inhibit binding of either targeting polypeptide (e.g., the IL2 polypeptide or TβRII receptor polypeptide). The linker polypeptide can be unstructured (e.g., lacking secondary structure), structured, or a combination thereof. In some embodiments, the linker sequence is a natural amino acid sequence of the IL polypeptide or soluble TβRII polypeptide. In some embodiments, the linker is not native to the IL polypeptide or TGF receptor polypeptide. For example, a non-native linker can comprise poly-glycine, poly-alanine, poly-serine amino acid or a combination thereof (e.g., GSSG, GGSS, GSAGG, etc.).

In some embodiments, the linker is a non-natural or synthetic linker. The term "synthetic linker" as used herein includes a chemical moiety comprising or derived from a group of atoms that is covalently attached to a targeting agent, and that is also covalently attached to a cytotoxic moiety. Linkers include compounds comprising or derived from divalent radicals such as an alkylene, an arylene, a heteroarylene, moieties such as: —(CR2)nO(CR2)n— wherein R2 is independently repeating units of alkyloxy (e.g. polyethylenoxy, PEG, polymethyleneoxy) and alkylamino (e.g. polyethyleneamino, polyetheramines such as Jeffamine™) and n is independently >1, in particular n may be 1 to 15; compounds including the linkers described in Example 1, N-succinimidyl 4-(maleimidomethyl)cyclohexanecarboxylate (SMCC) and N-succinimidyl 4-(2-pyridyldithio)butanoate (SPDB); and diacid ester and amides including succinate, succinamide, diglycolate, malonate, and caproamide as well as peptides, such as but not limited to repeating units of G, A and C (for example up to 10) with one or more lys residues or other suitable chemical groups for linking to a targeting agent and a cytotoxic moiety. The linker is optionally Cl-30 alkylene, unsubstituted or substituted with one or more substituents, and/or optionally interrupted with one or more heteromoieties independently selected from O, S, NR1, and/or optionally interrupted with one or more of C(O) and C(S), wherein R1 is independently selected from H, and Cl-6 alkyl. The linker can comprise a non-cleavable (stable linker) or cleavable unit (labile linker) such as a peptide bond or a disulfide bond. The linker can be conjugated to the targeting agent and/or the cytotoxic moiety via reactive functional groups.

Both cleavable and non-cleavable linkers can be used in the synthesis of fusion proteins (ADCs). Cleavable linkers include motifs that are either sensitive to lysosomal proteases or sensitive to an acidic pH (such as hydrazone, which is hydrolysed to cleave the linker in gemtuzumab ozogamicin and inotuzumab ozogamicin), or they can contain disulfide bridges that can be reduced by glutathione. The steric hindrance of disulfide bridges can be optimized to limit premature cleavage inside the cell. Generally, the disulfide linker is initially cleaved to release the thiol compound. Acid-cleavable linkers, such as hydrazone, are designed to remain stable at the neutral pH in the blood circulation, but in acidic cellular compartments they undergo hydrolysis and release the cytotoxic drug.

In some embodiments, the linker (e.g., peptide linker) comprises about 10 amino acids to about 100 amino acids. In some embodiments, the linker comprises about 10 amino acids to about 15 amino acids, about 10 amino acids to about 20 amino acids, about 10 amino acids to about 25 amino acids, about 10 amino acids to about 30 amino acids, about 10 amino acids to about 40 amino acids, about 10 amino acids to about 50 amino acids, about 10 amino acids to about 75 amino acids, about 10 amino acids to about 100 amino acids, about 15 amino acids to about 20 amino acids, about 15 amino acids to about 25 amino acids, about 15 amino acids to about 30 amino acids, about 15 amino acids to about 40 amino acids, about 15 amino acids to about 50 amino acids, about 15 amino acids to about 75 amino acids, about 15 amino acids to about 100 amino acids, about 20 amino acids to about 25 amino acids, about 20 amino acids to about 30 amino acids, about 20 amino acids to about 40 amino acids, about 20 amino acids to about 50 amino acids, about 20 amino acids to about 75 amino acids, about 20 amino acids to about 100 amino acids, about 25 amino acids to about 30 amino acids, about 25 amino acids to about 40 amino acids, about 25 amino acids to about 50 amino acids, about 25 amino acids to about 75 amino acids, about 25 amino acids to about 100 amino acids, about 30 amino acids to about 40 amino acids, about 30 amino acids to about 50 amino acids, about 30 amino acids to about 75 amino acids, about 30 amino acids to about 100 amino acids, about 40 amino acids to about 50 amino acids, about 40 amino acids to about 75 amino acids, about 40 amino acids to about 100 amino acids, about 50 amino acids to about 75 amino acids, about 50 amino acids to about 100 amino acids, or about 75 amino acids to about 100 amino acids. In some embodiments, the linker comprises about 10 amino acids, about 15 amino acids, about 20 amino acids, about 25 amino acids, about 30 amino acids, about 40 amino acids, about 50 amino acids, about 75 amino acids, or about 100 amino acids. In some embodiments, the linker comprises at least about 10 amino acids, about 15 amino acids, about 20 amino acids, about 25 amino acids, about 30 amino acids, about 40 amino acids, about 50 amino acids, or about 75 amino acids. In some embodiments, the linker comprises at most about 15 amino acids, at most about 20 amino acids, at most about 25 amino acids, at most about 30 amino acids, at most about 40 amino acids, at most about 50 amino acids, at most about 75 amino acids, or at most about 100 amino acids.

Figure 3:
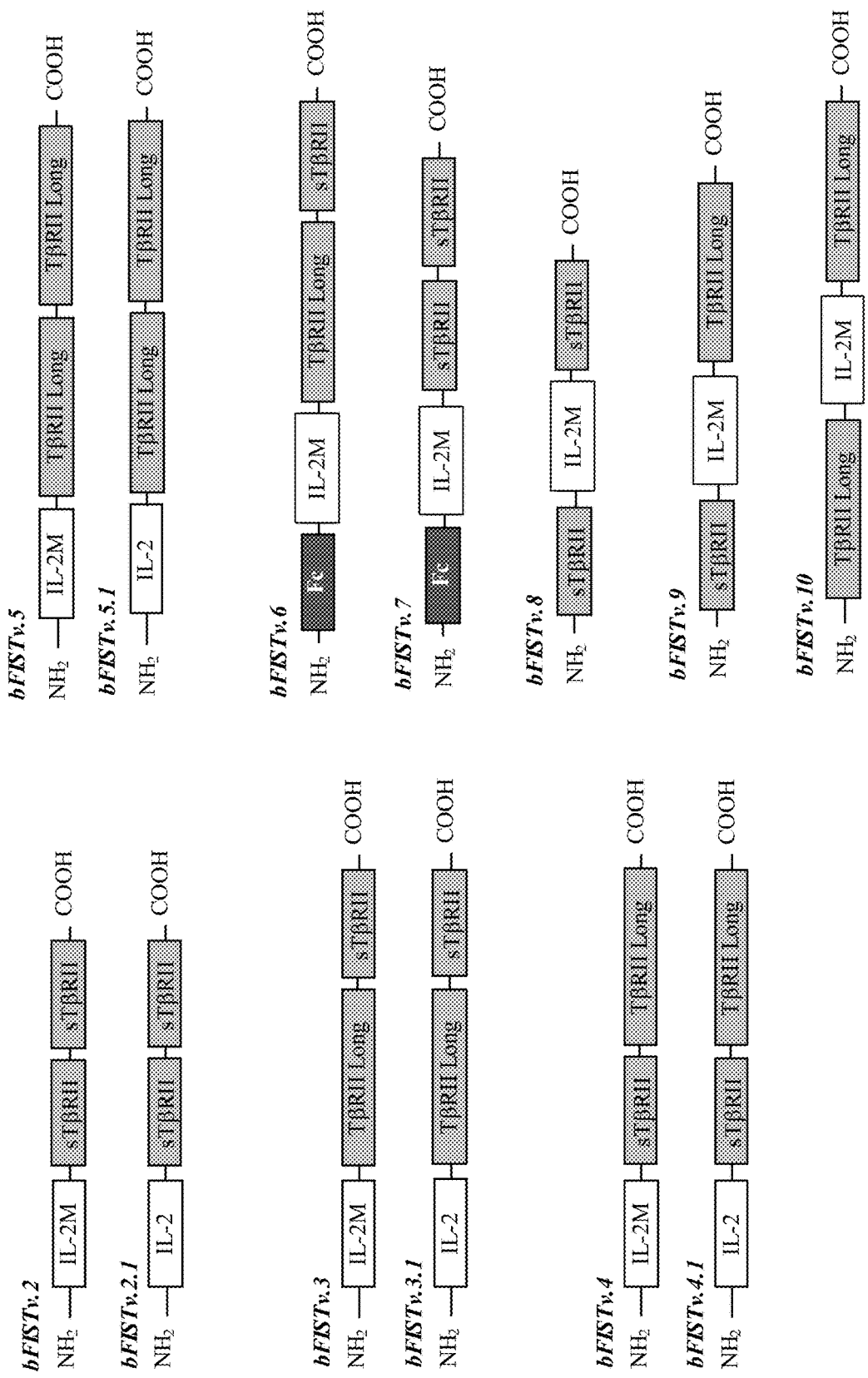
FIG. 3 shows a schematic representation of exemplary bivalent FIST (bFIST) fusion polypeptides.

Generally, different polypeptide elements of the fusion polypeptides can be arranged or ordered, from N-terminus to C-terminus, in any number of different combinations. For example, described herein are fusion polypeptides that comprise, from N-terminus to C-terminus, an IL polypeptide, a first TGFβ superfamily receptor polypeptide, and a second TGFβ superfamily receptor polypeptide. By way of further example, the fusion polypeptides as described herein, can also comprise, from N-terminus to C-terminus, a first TGFβ superfamily receptor polypeptide, an IL polypeptide, and a second TGFβ superfamily receptor polypeptide. In some embodiments, the fusion polypeptide further comprises a pharmacokinetic extender polypeptide (e.g., an Fc polypeptide or HSA polypeptide), wherein the fusion polypeptides further comprising the pharmacokinetic extender can be arranged or ordered, from N-terminus to C-terminus, in any number of different combinations. FIG. 3 shows a non-limiting schematic representation of exemplary embodiments of fusion polypeptides that comprise an IL polypeptide, a first TGFβ superfamily receptor polypeptide, and a second TGFβ superfamily receptor polypeptide (e.g., SEQ ID NOs: 10-25)

In some embodiments, the fusion polypeptide comprises an amino acid sequence of SEQ ID NO: 10. In some embodiments, the fusion polypeptide comprises an amino acid sequence of SEQ ID NO: 11. In some embodiments, the fusion polypeptide comprises an amino acid sequence of SEQ ID NO: 12. In some embodiments, the fusion polypeptide comprises an amino acid sequence of SEQ ID NO: 13. In some embodiments, the fusion polypeptide comprises an amino acid sequence of SEQ ID NO: 14. In some embodiments, the fusion polypeptide comprises an amino acid sequence of SEQ ID NO: 15. In some embodiments, the fusion polypeptide comprises an amino acid sequence of SEQ ID NO: 16. In some embodiments, the fusion polypeptide comprises an amino acid sequence of SEQ ID NO: 17. In some embodiments, the fusion polypeptide comprises an amino acid sequence of SEQ ID NO: 18. In some embodiments, the fusion polypeptide comprises an amino acid sequence of SEQ ID NO: 19. In some embodiments, the fusion polypeptide comprises an amino acid sequence of SEQ ID NO: 20. In some embodiments, the fusion polypeptide comprises an amino acid sequence of SEQ ID NO: 21. In some embodiments, the fusion polypeptide comprises an amino acid sequence of SEQ ID NO: 22. In some embodiments, the fusion polypeptide comprises an amino acid sequence of SEQ ID NO: 23. In some embodiments, the fusion polypeptide comprises an amino acid sequence of SEQ ID NO: 24. In some embodiments, the fusion polypeptide comprises an amino acid sequence of SEQ ID NO: 25.

In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to any one of SEQ ID NOs: 10 to 20. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to SEQ ID NO: 10. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to SEQ ID NO: 11. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 12. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 13. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 14. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 15.

In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 16. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 17. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 18. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 19. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 20. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 21. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 22. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 23. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 24. In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to of SEQ ID NO: 25.

In some embodiments, the fusion polypeptide consists of an amino acid sequence of SEQ ID NO: 10. In some embodiments, the fusion polypeptide consists of an amino acid sequence of SEQ ID NO: 11. In some embodiments, the fusion polypeptide consists of an amino acid sequence of SEQ ID NO: 12. In some embodiments, the fusion polypeptide consists of an amino acid sequence of SEQ ID NO: 13. In some embodiments, the fusion polypeptide consists of an amino acid sequence of SEQ ID NO: 14.

In some embodiments, the fusion polypeptide consists of an amino acid sequence of SEQ ID NO: 15. In some embodiments, the fusion polypeptide consists of an amino acid sequence of SEQ ID NO: 16. In some embodiments, the fusion polypeptide consists of an amino acid sequence of SEQ ID NO: 17. In some embodiments, the fusion polypeptide consists of an amino acid sequence of SEQ ID NO: 18. In some embodiments, the fusion polypeptide consists of an amino acid sequence of SEQ ID NO: 19. In some embodiments, the fusion polypeptide consists of an amino acid sequence of SEQ ID NO: 20. In some embodiments, the fusion polypeptide consists of an amino acid sequence of SEQ ID NO: 21. In some embodiments, the fusion polypeptide consists of an amino acid sequence of SEQ ID NO: 22. In some embodiments, the fusion polypeptide consists of an amino acid sequence of SEQ ID NO: 23. In some embodiments, the fusion polypeptide consists of an amino acid sequence of SEQ ID NO: 24. In some embodiments, the fusion polypeptide consists of an amino acid sequence of SEQ ID NO: 25.

The fusion polypeptides disclosed herein can further comprise a pharmacokinetic modulating polypeptide (e.g., a polypeptide that improves the pharmacokinetic profile of a therapeutic agent). For example, the fusion protein can further comprise an immunoglobulin Fc polypeptide or human serum albumin (HSA) polypeptide fused to the N-terminus of the IL polypeptide. In some embodiments, the immunoglobulin Fc region polypeptide is a human immunoglobulin Fc region polypeptide. In some embodiments, the immunoglobulin Fc region is an IgG Fc region. In some embodiments, the IgG Fc region is an IgG1, IgG2, IgG3, or IgG4 Fc region. In some embodiments, the PK modulator comprises an albumin polypeptide. In some embodiments, the albumin polypeptide is a human albumin polypeptide.

In certain embodiments the fusion polypeptides of the current disclosure are included in a pharmaceutical composition comprising one or more pharmaceutically acceptable excipients, carriers, and/or diluents. In certain embodiments, the fusion proteins of the current disclosure are administered suspended in a sterile solution. In certain embodiments, the solution comprises about 0.9% NaCl. In certain embodiments, the solution comprises about 5.0% dextrose. In certain embodiments, the solution further comprises one or more of: buffers, for example, acetate, citrate, histidine, succinate, phosphate, bicarbonate and hydroxymethylaminomethane (Tris); surfactants, for example, polysorbate 80, polysorbate 20, and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, Ethylenediaminetetraacetic acid or ethylene glycol-bis(O-aminoethyl ether)-N,N,N',N'-tetraacetic acid.

In certain embodiments, the fusion proteins of the current disclosure are shipped/stored lyophilized and reconstituted before administration. In certain embodiments, lyophilized fusion polypeptide formulations comprise a bulking agent such as, mannitol, sorbitol, sucrose, trehalose, dextran 40, or combinations thereof. The lyophilized formulation can be contained in a vial comprised of glass or other suitable non-reactive material. The fusion proteins when formulated, whether reconstituted or not, can be buffered at a certain pH, generally less than 7.0. In certain embodiments, the pH can be between 4.5 and 6.5, 4.5 and 6.0, 4.5 and 5.5, 4.5 and 5.0, or 5.0 and 6.0.

In certain embodiments, described herein is a method of preparing a treatment comprising admixing one or more pharmaceutically acceptable excipients, carriers, or diluents and a fusion polypeptide of the current disclosure. In certain embodiments, described herein is a method of preparing a treatment for storage or shipping comprising lyophilizing one or more fusion polypeptides of the current disclosure.

The fusion polypeptides described herein (e.g., SEQ ID NOs: 10 to 25) can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, e.g., a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors, regulatory elements such as promoters, enhancers, and polyadenylation signals for use in controlling transcription can be derived from mammalian, microbial, viral, or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (e.g., AttP-AttB recombination). Additionally, vectors can comprise sequences derived from transposable elements.

Methods of Use

The fusion polypeptides disclosed herein are useful as an effective agent for activating an immune response and/or inhibiting immunosuppression and fibrosis. For example, the disclosed fusion polypeptides are an effective anti-pathogen (e.g., antiviral) therapy that induces a unique gene expression profile downstream of an IL-2 receptor or IL-15 receptor that is not achieved by its single components or the combination, which leads to new, advantageous pharmacological properties. These novel multi-functional proteins can simultaneously activate several immune system mechanisms and signaling pathways that act in synergy to effectively eliminate intracellular pathogens (e.g., a virus, mycobacterium, etc.). At the cellular level, the immunotherapy platform activates a panoply of lymphoid cells (e.g., T cells, B cells, NK cells, NK-T cells, etc.) and indirectly prime antigen-presenting cells (e.g., dendritic cells and macrophages) due to, in part, GM-CSF induction triggering the cascade of specific immunological reactions against intracellular pathogens. At the molecular level, the fusion proteins disclosed herein activate key transcription factors and signaling molecules crucial to potentiate innate and adaptive immune responses. The fusion polypeptides described herein target and synchronize various arms of the immune system against an intracellular pathogen.

Accordingly, disclosed herein are methods of treating or ameliorating a pathogenic infection (e.g., an intracellular pathogen infection) in a subject, comprising administering a fusion polypeptide comprising: an interleukin (IL) polypeptide; a first TGFβ superfamily receptor polypeptide; and a second TGFβ superfamily receptor polypeptide. Also provided, in an aspect, are methods of treating a pathogenic infection (e.g., an intracellular pathogen infection) in a subject, comprising administering a fusion polypeptide comprising: an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ. Treating or ameliorating a pathogenic infection in a subject can also treat and/or reduce fibrosis associated with the infection of the pathogen. Additionally provided are methods of treating or ameliorating fibrosis associated with or resulting from a pathogenic infection (e.g., an intracellular pathogen infection) in a subject, comprising administering a fusion polypeptide comprising: an interleukin (IL) polypeptide; a first TGFβ superfamily receptor polypeptide; and a second TGFβ superfamily receptor polypeptide.

In some embodiments, TGFβ signaling associated with or resulting from a intracellular pathogen infection leads to pro-fibrotic signaling and/or fibrosis. Accordingly, also provided are methods of reducing or inhibiting fibrosis in an individual, the method comprising administering to the individual a therapeutically effective amount of a fusion polypeptide comprising: (a) an interleukin (IL) polypeptide; (b) a first TGFβ superfamily receptor polypeptide; and (c) a second TGFβ superfamily receptor polypeptide. Further provided are methods of reducing or inhibiting fibrosis resulting from an intracellular pathogen infection in an individual, the method comprising administering to the individual a therapeutically effective amount of a fusion polypeptide comprising: (a) an interleukin (IL) polypeptide; (b) a first TGFβ superfamily receptor polypeptide; and (c) a second TGFβ superfamily receptor polypeptide.

Further provided, are methods of neutralizing or inhibiting an intracellular pathogen in an individual having a pathogenic infection (e.g., an intracellular pathogen infection), comprising administering to the individual a fusion polypeptide comprising: an interleukin (IL) polypeptide; a first TGFβ superfamily receptor polypeptide; and a second TGFβ superfamily receptor polypeptide; thereby neutralizing or inhibiting the pathogen in the individual. Additionally provided are, methods of neutralizing or inhibiting an intracellular pathogen in an individual having a pathogenic infection (e.g., an intracellular pathogen infection), comprising administering to the individual a fusion polypeptide comprising: an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, thereby neutralizing or inhibiting the pathogen in the individual. Neutralizing or inhibiting a pathogenic infection (e.g., an intracellular pathogen infection) in a subject can also treat and/or reduce fibrosis associated with the infection of the pathogen. Additionally provided are methods of reducing or inhibiting fibrosis associated with or resulting from a pathogenic infection (e.g., an intracellular pathogen infection) in a subject, comprising administering a fusion polypeptide comprising: an interleukin (IL) polypeptide; a first TGFβ superfamily receptor polypeptide; and a second TGFβ superfamily receptor polypeptide.

In another aspect, also provided are methods of activating an anti-pathogen immune response cell comprising, contacting an immune cell with a fusion polypeptide comprising: an interleukin (IL) polypeptide; a first TGFβ superfamily receptor polypeptide; and a second TGFβ superfamily receptor polypeptide. Also provided are methods of activating an anti-intracellular pathogen immune response cell comprising, contacting an immune cell with a fusion polypeptide comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ.

In some embodiments, the IL polypeptide comprises an IL-2 polypeptide or IL-15. In some embodiments, the IL polypeptide comprises an IL-2 polypeptide. In some embodiments, the IL-2 polypeptide comprises SEQ ID NO: 2. In some embodiments, the IL-2 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 2. In some embodiments, the IL-2 polypeptide consists of SEQ ID NO: 2. In some embodiments, the IL-2 polypeptide comprises SEQ ID NO: 3. In some embodiments, the IL-2 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 3. In some embodiments, the IL-2 polypeptide consists of SEQ ID NO: 3. In some embodiments, the IL-2 polypeptide comprises SEQ ID NO: 3 In some embodiments, the IL-2 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 3. In some embodiments, the IL-2 polypeptide consists of SEQ ID NO: 3

IL-15 and IL-2 are known to share the same receptor subunits IL-2R beta and IL-2R gamma, leading to similar signaling properties (e.g., cellular responses) in lymphocytes. In some embodiments, the IL polypeptide comprises an IL-15 polypeptide. In some embodiments, the IL-15 polypeptide comprises SEQ ID NO: 5. In some embodiments, the IL-15 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 5. In some embodiments, the IL-15 polypeptide consists of SEQ ID NO: 5. In some embodiments, the IL polypeptide comprises an IL-15 polypeptide. In some embodiments, the IL-15 polypeptide comprises SEQ ID NO: 4. In some embodiments, the IL-15 polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 4. In some embodiments, the IL-15 polypeptide consists of SEQ ID NO: 4

In some embodiments, the first TGFβ superfamily receptor polypeptide and/or the second TGFβ superfamily receptor polypeptide comprises an activin receptor polypeptide or fragment thereof, a bone morphogenetic protein (BMP) receptor polypeptide or fragment thereof, a glial cell-derived neurotrophic factor (GDNF) receptor polypeptide or fragment thereof, or a TGFβ receptor II polypeptide or fragment thereof. In some embodiments, the first TGFβ superfamily receptor polypeptide and/or the second TGFβ superfamily receptor polypeptide comprises a TGFβ receptor II (TβRII) polypeptide or fragment thereof.

In some embodiments, the first TGFβ superfamily receptor polypeptide and/or the second TGFβ superfamily receptor polypeptide comprises a soluble TGFβ receptor II (TβRII) polypeptide or fragment thereof. In some embodiments, the first TGFβ superfamily receptor polypeptide and/or the second TGFβ superfamily receptor polypeptide comprises a soluble TGFβ receptor II (TβRII) polypeptide comprising SEQ ID NO: 8, SEQ ID NO: 9, or a combination thereof. In some embodiments, the first TGFβ superfamily receptor polypeptide comprises an amino acid sequence of SEQ ID NO: 8 and the second TGFβ superfamily receptor polypeptide comprises a truncation of an amino acid sequence of SEQ ID NO: 9. In some embodiments, the soluble TGFβ receptor II polypeptide comprises an amino acid sequence having greater than about 80%, greater than about 85%, greater than about 90%, greater than about 95%, greater than about 96%, greater than about 97%, greater than about 98%, or greater than about 99% sequence identity to SEQ ID NO: 8 or SEQ ID NO: 9

In some embodiments, the first TGFβ superfamily receptor polypeptide and/or the second TGFβ superfamily receptor polypeptide binds a TGF-β1 polypeptide, a TGF-β2 polypeptide, a TGF-β3 polypeptide, a activin βA polypeptide, a activin βB polypeptide, a activin βC polypeptide, a activin βE polypeptide, a bone morphogenic protein (BMP) 2 polypeptide, a BMP 3 polypeptide, a BMP4 polypeptide, a BMP 5 polypeptide, a BMP 6 polypeptide, a BMP 7 polypeptide, a BMP 8 polypeptide, a BMP 9 polypeptide, a BMP 10 polypeptide, a BMP 11 polypeptide, a BMP 12 polypeptide, a BMP 13 polypeptide, a BMP 14 polypeptide, a BMP 15 polypeptide, a growth differentiation factor (GDF) 1 polypeptide, a GDF 3 polypeptide, a GDF 8 polypeptide, a GDF 9 polypeptide, a GDF 15 polypeptide, a Nodal polypeptide, a Inhibin a polypeptide, an anti-Mullerian Hormone polypeptide, a Lefty 1 polypeptide, a Lefty 2 polypeptide, an arteman polypeptide, a Persephin polypeptide, or a Neurturin polypeptide. In some embodiments, the first TGFβ superfamily receptor polypeptide and/or the second TGFβ superfamily receptor polypeptide binds a TGFβ1 polypeptide, a TGFβ2 polypeptide, a TGFβ3 polypeptide, or any combination thereof. In some embodiments, the first TGFβ superfamily receptor polypeptide and the second TGFβ superfamily receptor polypeptide binds a TGFβ1 polypeptide. In some embodiments, the truncated TGFβ superfamily receptor polypeptide comprises an N terminus truncation, a C terminus truncation, or combination thereof. In some embodiments, the truncated TGFβ superfamily receptor polypeptide is a truncated soluble TGFβ receptor II (sTβRII) polypeptide.

In some embodiments, the truncation comprises greater than 2, greater than 5, greater than 7, greater than 10, greater than 15, greater than 20, greater than 25, or greater than 30 amino acids. In some embodiments, the IL polypeptide comprises a truncated IL polypeptide. In some embodiments, the truncated IL polypeptide comprises an N terminus truncation, a C terminus truncation, or a combination thereof. In some embodiments, the truncated IL polypeptide comprises a truncated IL-2 polypeptide or IL-15 polypeptide. In some embodiments, the fusion polypeptide further comprises a linker polypeptide or a linker molecule attaching the first TGFβ superfamily receptor polypeptide and the second TGFβ superfamily receptor polypeptide.

In some embodiments, the fusion polypeptide further comprises a linker polypeptide fusing the IL polypeptide and the first TGFβ superfamily receptor polypeptide. In some embodiments, the fusion polypeptide further comprises a pharmacokinetic (PK) modulator. In some embodiments, the pharmacokinetic modulator comprises an immunoglobulin constant (Fc) region polypeptide. In some embodiments, the immunoglobulin Fc region polypeptide is a human immunoglobulin Fc region polypeptide. In some embodiments, the immunoglobulin Fc region is an IgG Fc region. In some embodiments, the IgG Fc region is an IgG1, IgG2, IgG3, or IgG4 Fc region. In some embodiments, the PK modulator comprises an albumin polypeptide. In some embodiments, the albumin polypeptide is a human albumin polypeptide.

In some embodiments, the fusion polypeptide comprises an amino acid sequence having at least about 80%, at least about 85%, at least about 90%, at least about 95%, at least about 96%, at least about 97%, at least about 98%, or at least about 99% sequence identity to any one of SEQ ID NOs: 10-25. In some embodiments, the fusion polypeptide comprises an amino acid sequence of SEQ ID NO: 10. In some embodiments, the fusion polypeptide comprises an amino acid sequence of SEQ ID NO: 11. In some embodiments, the fusion polypeptide comprises an amino acid sequence of SEQ ID NO: 12. In some embodiments, the fusion polypeptide comprises an amino acid sequence of SEQ ID NO: 13. In some embodiments, the fusion polypeptide comprises an amino acid sequence of SEQ ID NO: 14. In some embodiments, the fusion polypeptide comprises an amino acid sequence of SEQ ID NO: 15. In some embodiments, the fusion polypeptide comprises an amino acid sequence of SEQ ID NO: 16. In some embodiments, the fusion polypeptide comprises an amino acid sequence of SEQ ID NO:

17. In some embodiments, the fusion polypeptide comprises an amino acid sequence of SEQ ID NO: 18. In some embodiments, the fusion polypeptide comprises an amino acid sequence of SEQ ID NO: 19. In some embodiments, the fusion polypeptide comprises an amino acid sequence of SEQ ID NO: 20. In some embodiments, the fusion polypeptide comprises an amino acid sequence of SEQ ID NO: 21. In some embodiments, the fusion polypeptide comprises an amino acid sequence of SEQ ID NO: 22. In some embodiments, the fusion polypeptide comprises an amino acid sequence of SEQ ID NO: 23. In some embodiments, the fusion polypeptide comprises an amino acid sequence of SEQ ID NO: 24. In some embodiments, the fusion polypeptide comprises an amino acid sequence of SEQ ID NO: 25. In some embodiments, the fusion polypeptide consists of any one of SEQ ID NOs: 10-25.

In some embodiments, the fusion polypeptide activates target cells expressing an IL-2 or IL-15 receptor. In some embodiments, the target cell is an immune cell. In some embodiments, the immune cell is a T cells, natural killer cells NKT cells, B cells, or gamma delta T cells.

In some instances, target cells comprise a type of cell, cell population, or composition of cells which are the desired cells to be collected, isolated, or separated by the present disclosure. Target cells represent cells that various procedures described herein require or are designed to purify, collect, engineer, etc. What the specific cells are depends on the context in which the term is used. For example, if the objective of a procedure is to isolate a particular kind of stem cell, that cell would be the target cell of the procedure. In certain instances, target cells and desired cells are interchangeable and have the same meaning regarding the present disclosure. Target cells can exist in a genus-species relationship. For example, if target cells comprise leukocytes, the target cells would include T cells.

The methods disclosed herein are particularly useful for or comprise the activation of immune cells. In some stances, immune cells generally comprise cells of the immune system. Immune cells are derived from myeloid or lymphoid cell linages. Generally, the methods disclosed herein are directed towards, but not limited to, the activation of immune effector cells. In some instances, immune effector cell comprises a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes. In certain embodiments, T cells, NK cells, B cells, NKT cells and gamma/delta T cells or a combination thereof are activated by the fusion polypeptide.

An immune effector function or an immune effector response encompasses and/or comprises, in some instances, a function or response of an immune effector cell that enhances or promotes an immune attack to a target cell. E.g., an immune effector function or response refers to a property of T cells or NK cells that promotes killing or the inhibition of growth or proliferation, of a target cell. Immune effector function includes direct cytotoxicity, cytokine release, chemokine release, phagocytosis, or other immune function that primes or perpetuates an immune response. In some instances, effector function comprises a specialized function of a cell. Effector function of a T cell, for example, may be cytolytic activity or helper activity including the secretion of cytokines.

The methods disclosed herein are particularly useful for or comprise the activation of myeloid-derived immune cells. Myeloid cells encompass terminally differentiated cells of the myeloid lineage. These cells include neutrophils, eosinophils and monocytes/macrophages, myeloid dendritic cells. In one embodiment of any aspect of the present disclosure, the myeloid cell is a neutrophil, eosinophil, or monocyte/macrophage/dendritic cells. In certain instances, macrophage and/or macrophage-like cells generally comprise macrophages, monocytes, and cells of macrophage/monocyte lineage, and any other similar cells which perform the functions generally associated with macrophages, such as phagocytosis or antigen presentation to other classes of immune cells such as T-cells and B-cells in order to sensitize these cells to a particular target, including but not limited to pathogenic organisms or particles (e.g. viruses, bacterial cells, etc.).

The methods disclosed herein are particularly useful for or comprise the activation of lymphocyte immune cells. In some instances, lymphocytes include natural killer (NK) cells, T cells, or B cells. NK cells are a type of cytotoxic (cell toxic) lymphocyte that represent a major component of the inherent immune system. NK cells kill cells infected by intracellular pathogens. In some embodiments, the natural killer (NK) cells comprise cells of the immune system that kill target cells in the absence of a specific antigenic stimulus, and without restriction according to MHC class. Target cells may be pathogens or cells harboring pathogens. NK cells are characterized by the presence of CD56 and the absence of CD3 surface markers. In some embodiments, T cells comprise a subset of lymphocytic cells that express a surface marker of "CD3" (T-cell receptor). Unless otherwise indicated, T cells include $CD4^+$ (e.g., T-helper cells) and $CD8^+$ (e.g., cytotoxic killer cells).

The fusion polypeptides provided herein are useful for inhibiting, preventing, or reducing immunosuppression. Accordingly, treating or a treatment, in some embodiments, comprises activating immune effector cells that target a pathogen or pathogen infected cell and/or reducing the activation of immunosuppressive cells (e.g., Treg cells and M2 macrophages that are immunosuppressive macrophages and can be associated with immunosuppressive or immunodeficient disease state) and/or myeloid-derived suppressor cells (MDSCs). The methods provided herein are also useful for the suppression or reduction of immunosuppressive immune cells such as T regulatory cells. In some instances, immunosuppressive cells comprise Tregs or regulatory T cells. Tregs comprise CD4+CD25+FOxP3+ T cells that suppress CD4+CD25− and CD8+ T cell proliferation and/or effector function, or that otherwise down-modulate an immune response. Notably, Tregs may down-regulate immune responses mediated by CD8 T cells, Natural Killer cells, Natural Killer T cells as well as other immune cells. Further encompassed, in some embodiments, is the blockade or prevention of immunosuppressive cell differentiation or activation.

In some embodiments, the pathogenic infection is an intracellular bacterial infection. In certain instances, an intracellular bacterial infection comprises the invasion of the host organism by pathogenic bacteria. In certain instances, this includes the excessive growth of bacteria which are normally present in or on the body of the organism, but more generally, a bacterial infection is any situation in which the presence of a bacterial population(s) is damaging to a host organism. Thus, for example, an organism suffers from an intracellular bacterial infection when excessive numbers of a bacterial population are present in or on the organism's body, or when the effects of the presence of a bacterial population(s) is damaging to the cells, tissue, or organs of the organism. In some instances, bacteria refers to a domain of prokaryotic organisms. Bacteria include at least 11 distinct groups as follows: (1) Gram-positive (gram+) bacteria, of which there are two major subdivisions: (i) high G+C group (Actinomycetes, Mycobacteria, *Micrococcus*, others) (ii) low G+C group (*Bacillus, Clostridia, Lactobacillus*, Staphylococci, Streptococci, Mycoplasmas); (2) Proteobacteria, e.g., Purple photosynthetic and non-photosynthetic Gram-negative bacteria (includes most common Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and Thermosipho thermophiles. Gram-negative bacteria include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*. Gram-positive bacteria include cocci, nonsporulating rods, and sporulating rods. The genera of Gram-positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*. In some instances, pathogenic bacteria are bacterial species that cause disease(s) in another host organism (e.g., animals and plants) by directly infecting the other organism, or by producing agents that causes disease(s) in another organism (e.g., bacteria that produce pathogenic toxins and the like).

In some embodiments, the intracellular bacterial infection is an infection by the genera *Shigella, Campylobacter, Salmonella, Clostridium, Escherichia*, Chlamydiae, Rickettssiaceae, *Coxiella*, Mycobacteriaceae, and combinations thereof. In some embodiments, the intracellular bacteria is drug resistant. In some embodiments, the intracellular bacterium is gram negative. In some embodiments, the intracellular bacterium is gram positive.

In some embodiments, the pathogenic infection is a viral infection. In some instances, a viral infection comprises an infection caused by one or more viruses. In some embodiments, the virus is an RNA virus. In some embodiments, the virus in a DNA virus. In some embodiments, the viral infection comprises a virus from the family denoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. In some embodiments, viruses include, without limitations to Polioviruses, Coronaviridae and Coronaviruses, Rhinovirus (all subtypes), Adenoviruses (all subtypes), Hepatitis A, Hepatitis B, Hepatitis C, Hepatitis D, Human papillomavirus (including all subtypes), Rabies viruses, Human T-cell lympotropic virus (all subtypes), Rubella virus, Mumps virus, Coxsackie virus A (all subtypes), Coxsackie virus B (all subtypes), human enteroviruses, herpesviruses including cytomegalovirus, Epstein-Barr virus, human herpesviruses (all subtypes), herpes simplex virus, varicella zoster virus, human immunodeficiency virus (HIV) (all subtypes), Epstein-Barr virus, Reoviruses (all subtypes), Filoviruses including Marburg virus and Ebola virus (all stains), Arenaviruses including Lymphocytic choriomeningitis virus, Lassa virus, Junin virus, and Machupo virus, Arboviruses including West Nile virus, Dengue viruses (all serotypes), Zika virus, Colorado tick fever virus, Sindbis virus, Togaviraidae, Flaviviridae, Bunyaviridae, Reoviridae, Rhabdoviridae, Orthomyxoviridae, Poxviruses including orthopoxvirus (variola virus, monkeypox virus, vaccinia virus, cowpox virus), yatapoxviruses (tanapox virus, Yaba monkey tumor virus), parapoxvirus, molluscipoxvirus, Yellow fever, Hantaviruses including Hantaan, Seoul, Dobrava, Sin Nombre, Puumala, and Dobrava-like Saaremaa, human para influenza viruses and influenza viruses (all types), HlNl influenza and swine influenza viruses, respiratory syncytial virus (all subgroups), rotaviruses including human rotaviruses A-E, bovine rotavirus, rhesus monkey rotavirus, Polyomaviruses including simian virus 40, JC virus, BK virus, Coltiviruses, eyach virus, calciviruses, and Parvoviridae including dependovirus, parvovirus and erythrovirus. In some embodiments, the viral infection comprises coronavirus. In some embodiments, the viral infection comprises SARS-COV-2. In some embodiments, the viral infection comprises influenza.

Accordingly, the compositions provided herein are useful in methods for treating a pathogenic infection (e.g., an intracellular pathogen infection). Thus, provided herein are uses of a fusion polypeptide of the disclosure comprising an interleukin (IL) polypeptide, a first TGFβ superfamily receptor polypeptide, and a second TGFβ superfamily receptor polypeptide, in a method of neutralizing or inhibiting a virus and/or progression in an individual having a viral infection. Also provided herein are uses of a fusion polypeptide of the disclosure comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, in a method of neutralizing or inhibiting a virus and/or progression in an individual having a viral infection.

Further provided herein are uses of a fusion polypeptide of the disclosure comprising an interleukin (IL) polypeptide, a first TGFβ superfamily receptor polypeptide, and a second TGFβ superfamily receptor polypeptide, in a method of neutralizing or inhibiting an intracellular bacterium and/or progression in an individual having a bacterial infection. Also provided herein are uses of a fusion polypeptide of the disclosure comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, in a method of neutralizing or inhibiting an intracellular bacterium and/or progression in an individual having a bacterial infection.

Provided herein are fusion polypeptides comprising an interleukin (IL) polypeptide, a first TGFβ superfamily receptor polypeptide, and a second TGFβ superfamily receptor polypeptide, for use in a method of neutralizing or inhibiting a virus and/or progression in an individual having a viral infection. Also provided herein are fusion polypeptides comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, for use in a method of neutralizing or inhibiting a virus and/or progression in an individual having a viral infection.

Further provided herein are fusion polypeptides comprising an interleukin (IL) polypeptide, a first TGFβ superfamily receptor polypeptide, and a second TGFβ superfamily receptor polypeptide, for use in a method of neutralizing or inhibiting an intracellular bacterium and/or progression in an individual having a bacterial infection. Also provided herein are fusion polypeptides comprising an IL polypeptide that binds to and agonizes an IL receptor; a first TGFβ superfamily receptor polypeptide that binds to and sequesters soluble TGFβ; and a second TGFβ superfamily receptor polypeptide that binds to and sequesters soluble TGFβ, for use in a method of neutralizing or inhibiting an intracellular bacterium and/or progression in an individual having a bacterial infection.

In certain embodiments, the fusion proteins can be administered to a subject in need thereof by any route suitable for the administration of fusion protein-containing pharmaceutical compositions, such as, for example, subcutaneous, intraperitoneal, intravenous, intramuscular, or intracerebral, etc. In certain embodiments, the fusion proteins are administered intravenously. In certain embodiments, the fusion proteins are administered subcutaneously. In certain embodiments, the fusion proteins are administered intravenously. In certain embodiments, the fusion proteins are administered on a suitable dosage schedule, for example, weekly, twice weekly, monthly, twice monthly, once every two weeks, once every three weeks, or once a month etc. In certain embodiments, the fusion proteins are administered once every three weeks. The fusion proteins can be administered in any therapeutically effective amount. In certain embodiments, the therapeutically acceptable amount is from about 0.1 mg/kg to about 50 mg/kg. In certain embodiments, the therapeutically acceptable amount is from about 1 mg/kg to about 40 mg/kg. In certain embodiments, the therapeutically acceptable amount is from about 5 mg/kg to about 30 mg/kg. Therapeutically effective amounts include amounts that are sufficient to ameliorate one or more symptoms associated with the disease or affliction to be treated.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying, or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The term "a therapeutically effective amount" of a compound of the present application refers to an amount of the compound of the present application that elicits the biological or medical response of a subject, for example, reduction or inhibition of a pathogen infection, or ameliorate symptoms, alleviate conditions, slow or delay disease progression, or prevent a disease, etc. In one non-limiting embodiment, the term "a therapeutically effective amount" refers to the amount of a compound of the present application that, when administered to a subject, is effective to at least partially alleviate, inhibit, prevent, and/or ameliorate a condition, or a disorder or a disease, or at least partially inhibit activity of a targeted enzyme or receptor.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining", "measuring", "evaluating", "assessing", "assaying", and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject", "individual", or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. In some embodiments, the subject may be diagnosed with a pathogen or pathogenic infection or suspected of being at high risk for a pathogen infection.

The term "in vivo" is used to describe an event that takes place in a subject's body. The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay. The term "in vitro" is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed.

As used herein, the term "about" a number refers to that number plus or minus 10% of that number. The term "about" a range refers to that range minus 10% of its lowest value and plus 10% of its greatest value.

The section headings used herein are for organizational purposes only and are not to be construed as limiting the subject matter described.

EXAMPLES

The following examples are included for illustrative purposes only and are not intended to limit the scope of the disclosure.

Example 1—Improved IL-2 Activation of Immune Cells

Exemplifying the fusion polypeptide compositions and methods disclosed herein, the following example demonstrates that the fusion polypeptides comprising an interleukin-2 (IL-2) polypeptide, a first sTBRII receptor polypeptide, and a second sTBRII receptor polypeptide (bFIST) induces higher levels of IFN-gamma and CXCL10 in human NK cells as compared to fusion proteins comprising an IL-2 polypeptide and single sTBRII receptor polypeptide (monovalent FIST).

Figure 1B:
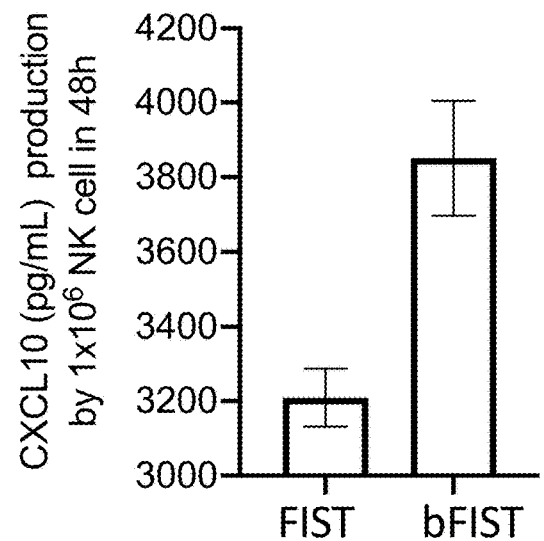

Human T cells and NK cells were isolated from PBMC by negative selection and were stimulated with FIST (IL2-sTBRII, monovalent) or a FIST variant with bivalent sTBRII traps (IL2-sTBRII-sTBRII) for 48 hours. After 48 hours of incubation, the conditioned media were collected to quantify the levels of IFNγ from T cells and CXCL10 from NK cells by ELISA. As shown in the data of FIGS. 1A-1B, bFIST demonstrates significantly higher IL-2 receptor activation than FIST (monovalent FIST).

Example 2—Improved TGFβ1 Binding

Exemplifying the fusion polypeptide compositions and methods disclosed herein, the following example demonstrates that the fusion polypeptides comprising an interleukin-2 (IL-2) polypeptide, a first sTBRII receptor polypeptide, and a second sTBRII receptor polypeptide (bFIST) more effectively bind active TGFβ1 as compared to fusion proteins comprising an IL-2 polypeptide and single sTBRII receptor polypeptide (monovalent FIST).

Figure 2:
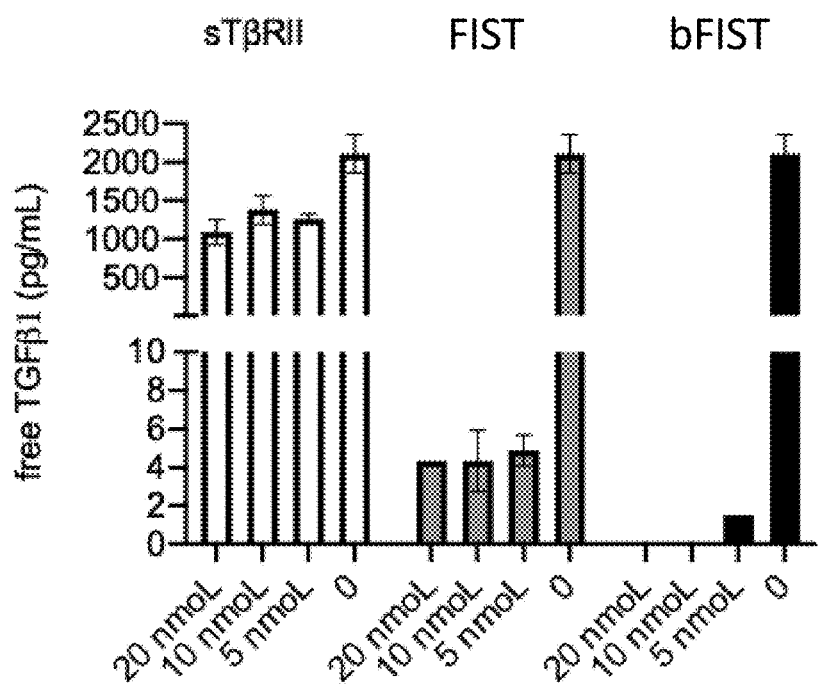
FIG. 2 shows data depicting the quantification of active TGFβ1 detected in solution after 30 minutes incubation period with 5-20 nanomoles of human monovalent FIST (monovalent FIST), bivalent FIST (bFIST), or sTBRII.

Human active TGFβ1 (2 ng/mL) previously activated with 4 mM HCl containing 0.1% of bovine serum albumin (BSA) was incubated with sTBRII control, FIST (monovalent FIST) or bFIST (5-20 nmoL) for 30 minutes at RT and free active TGFβ in solution was quantified by ELISA (ELISA for human TGFβ1 immunoassay).

bFIST effectively blocks active TGFβ1 in solution at significant lower concentrations than sTBRII as illustrated in that FIG. 2. These results indicate that IL-2 as part of the fusion protein also modifies the sTBRII portion and its binding properties to active TGFβ. Furthermore, the bivalent sTBRII trap variant has more effective TGFβ blocking activity.

Example 3—Blockage of TGFβ Isoforms in Solution

Exemplifying the fusion polypeptide compositions and methods disclosed herein, the following example demonstrates that the fusion polypeptides comprising an interleukin-2 (IL-2) polypeptide, a first sTBRII receptor polypeptide, and a second sTBRII receptor polypeptide more effectively binds TGFβ isoforms.

The blocking activity of TGFβ isoforms in solution by bFISTv3, FIST, or control (TβRII isoform 2) was determined by incubating bFISTv3, FIST, or control with 1 ng/mL of active TGF 3 isoforms. Equimolar concentrations (range of 5-5×10$^{-6}$ nmoL) of bFISTv3, FIST or control (TβRII isoform 2) were compared in their ability to block active TGFβ isoforms in solution. bFISTv3, FIST or control were incubated with 1 ng/mL of active TGFβ isoforms diluted in phosphate buffered saline (PBS) for 30 minutes and the free TGFβ (unblocked) was quantified by ELISAs specific for each TGFβ isoforms.

Figure 4A:
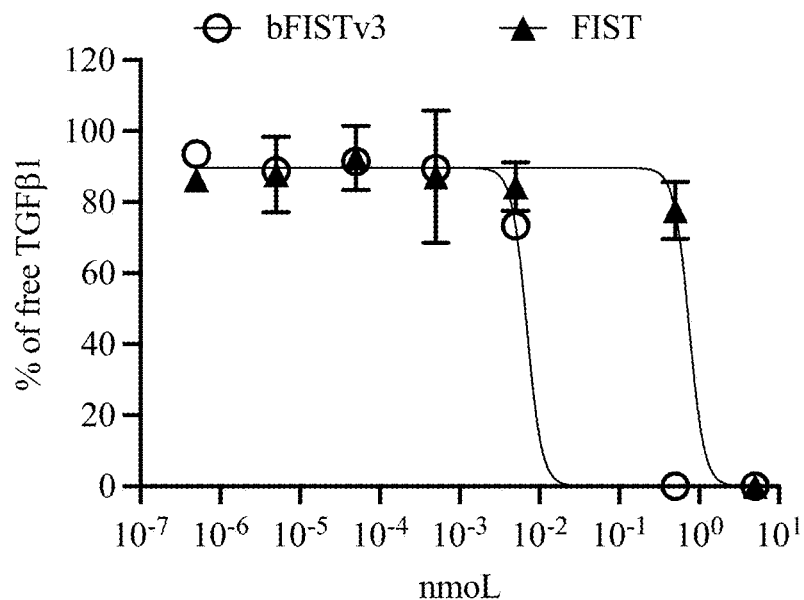
FIGS. 4A, 4B, and 4C show comparison between bivalent FIST protein and monovalent FIST in the blockage of TGFβ isoforms.
Figure 4B:
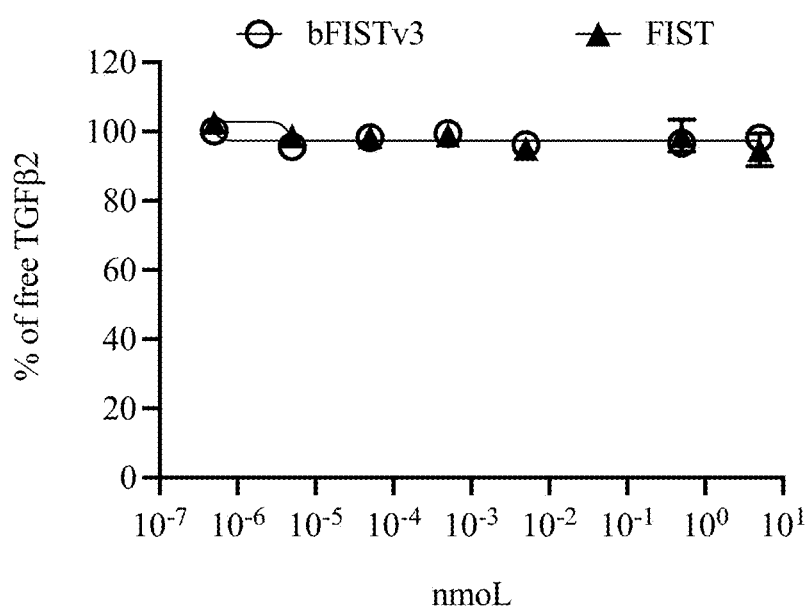
Figure 4C:
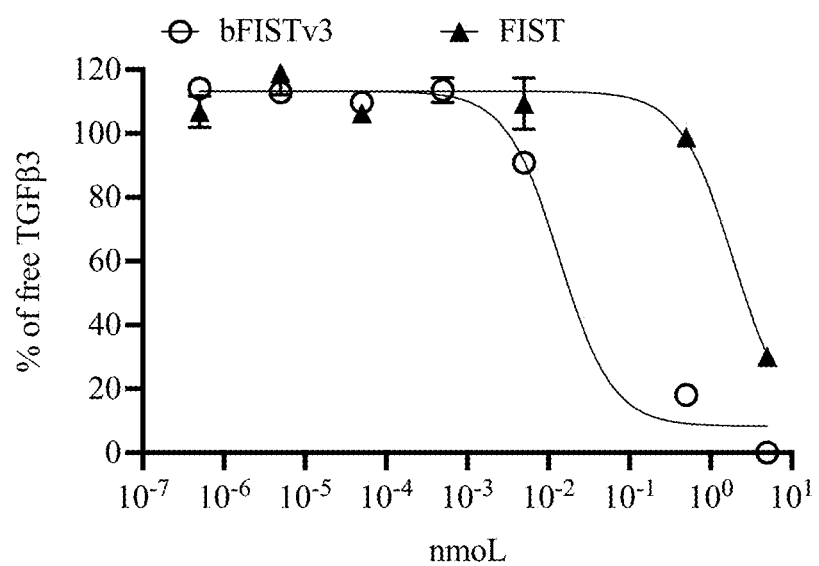

TGFβ causes a wide range of immune suppression in several immune cell types including inhibition of crucial early innate IFN responses. Defective IFN immune responses enhance the severity of viral infections often followed by secondary bacterial infections, scarring, fibrosis, and loss of lung functions. bFISTv3 demonstrated a significantly increased affinity with picomolar potency for TGFβ1 (9 picomoles) and TGFβ3 (70 picomoles) compared to FIST and the control TβRII isoform 2 (FIG. 4A-C). FIG. 4A shows blocking of the TGFβ1 binding. FIG. 4B shows blocking of the TGFβ2 binding. FIG. 4C shows blocking of the TGFβ3 binding. Table 1 shows binding values for TGFβ blocking activity in solution.

TGFβ1 and TGFβ3 isoforms are known as inducers of fibrotic diseases. In contrast, TGFβ2 was not blocked by the fusion protein or control. TGFβ2 is an important regulator of hematopoiesis, cardiovascular function and glucose and fatty acid metabolism.

TABLE 1

| IC50 values for active TGFβ blocking activity in solution | | | |
|---|---|---|---|
| Molecule | TGFβ1 | TGFβ2 | TGFβ3 |
| TβRII (isoform II) | 0.02 nM | NA | 0.26 nM |
| FIST | 1.29 nM | NA | 3.6 nM |
| bFISTv3 | 0.009 nM | NA | 0.07 nM |

Example 4—Inhibition of TGFβ1-Mediated Suppression of CTLL-2 Proliferation

Exemplifying the fusion polypeptide compositions and methods disclosed herein, the following example demonstrates that the fusion polypeptides comprising an interleukin-2 (IL-2) polypeptide, a sTβRII receptor polypeptide, and a second sTβRII receptor polypeptide more effectively induces CTLL-2 (cytotoxic T cell line) proliferation and prevents the TGFβ1-mediated suppression.

Figure 5A:
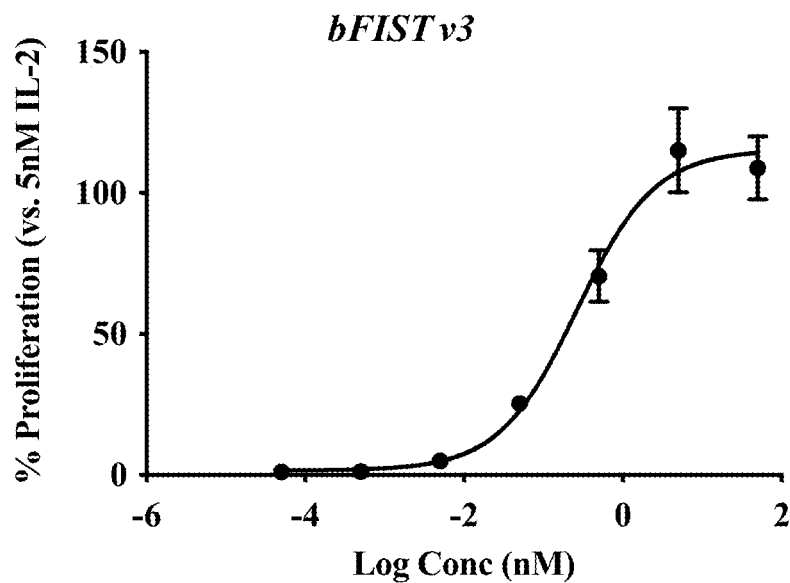
FIGS. 5A, 5B, 5C, 5D, 5E, and 5F show inhibition of TGFβ1-mediated suppression of cytotoxic T cell proliferation.
Figure 5B:
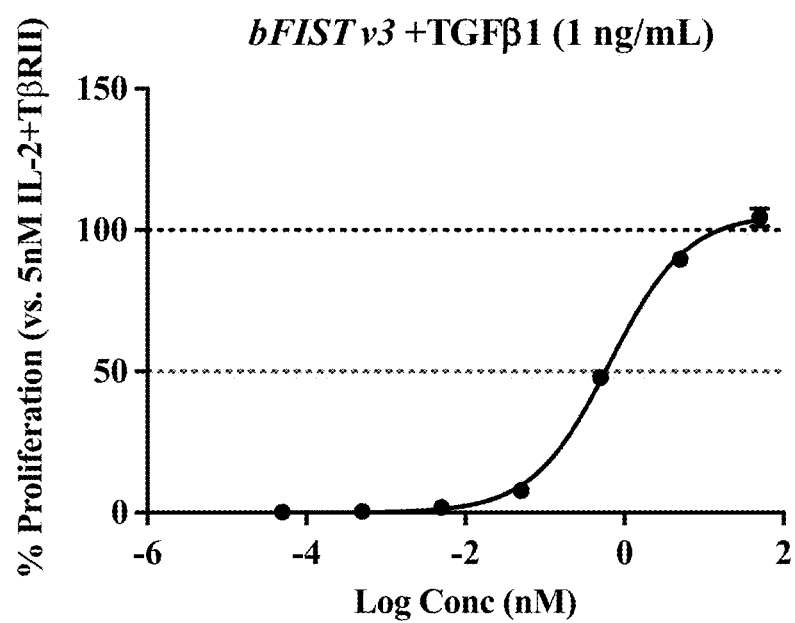
Figure 5C:
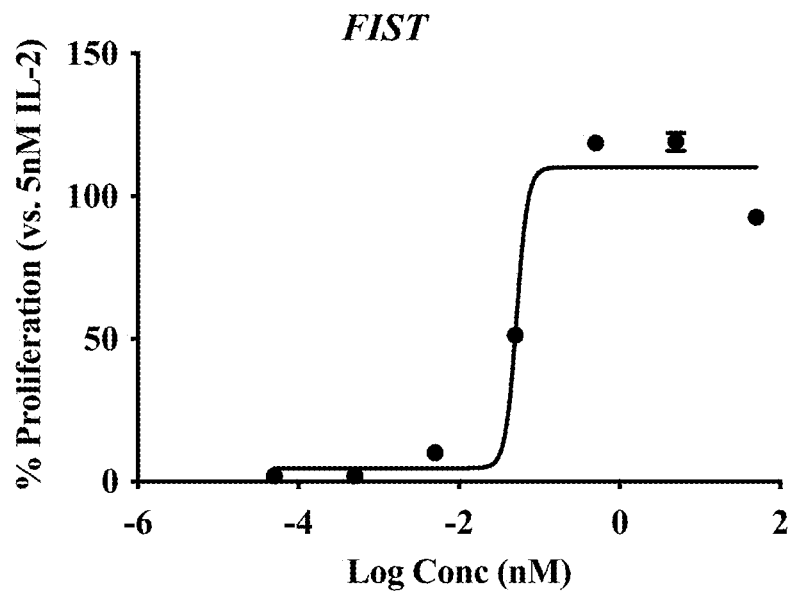
Figure 5D:
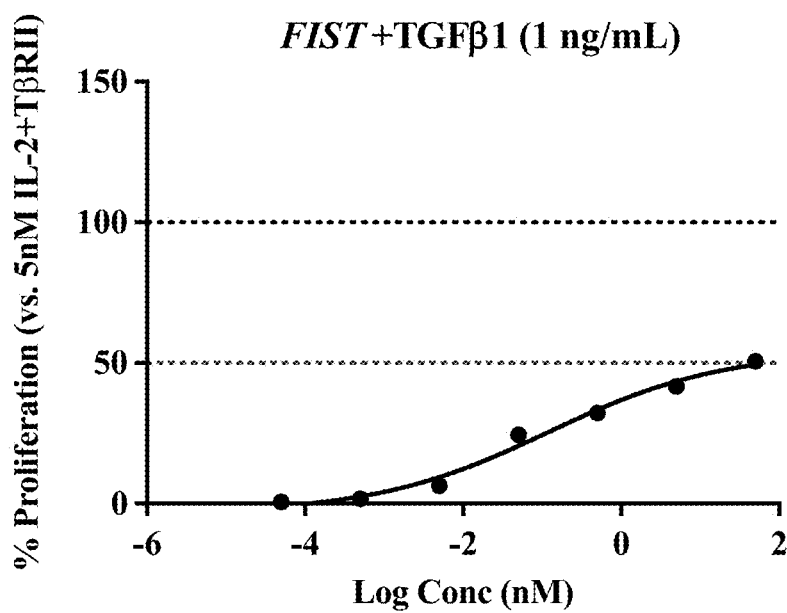
Figure 5E:
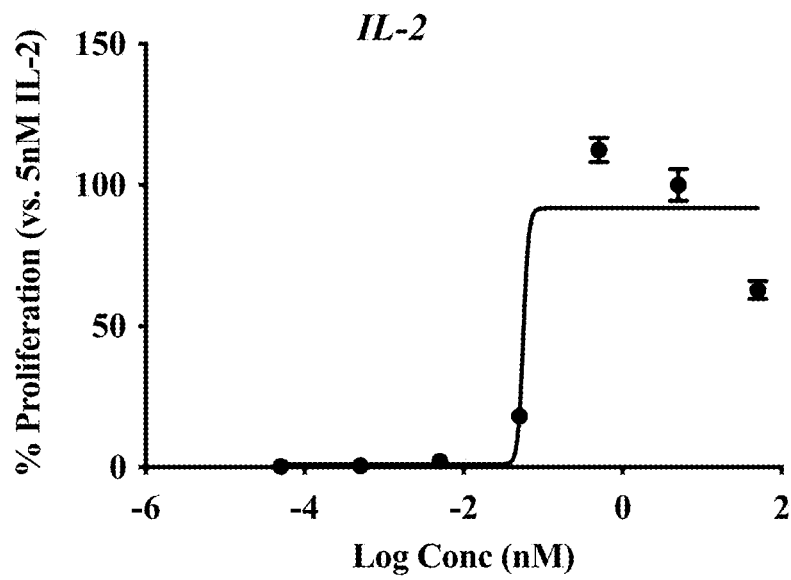
Figure 5F:
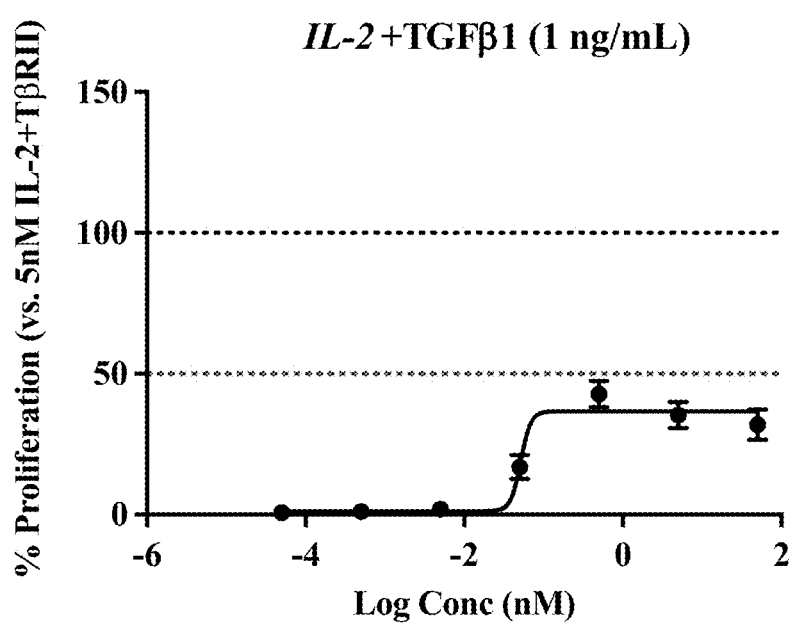

Equimolar concentrations (range of 50-5×10$^5$ nmoL) of bFISTv3, FIST or controls (IL-2 and TβRII isoform 2) were compared in their ability to inhibit active TGFβ1-mediated suppression of CTLL-2 proliferation. CTLL-2 cells (5×10$^3$ cells/well) were stimulated with equimolar concentration of bFISTv3, FIST or controls for 72 hours at 37° C. with/without active TGFβ1 (1 ng/mL). After the incubation period, cell proliferation was determined by a luminescent cell viability assay. The absolute IC50 was determined with a dose-response curve using nonlinear regression model with a sigmoidal dose response. The surviving rate (%)= $(\text{Lum}_{Test\ article}-\text{Lum}_{Medium\ control})/(\text{Lum}_{Vehicle\ control}-\text{Lum}_{Medium\ control})\times 100\%$. The cell number was quantified by a luminescence signal versus cell dose curve.

bFISTv3 induces CTLL-2 cell proliferation and prevents the TGFβ1-mediated suppression of CTLL-2 proliferation more effectively than FIST (monovalent FIST). TGFβ suppresses T-cell responses by inhibiting T-cell proliferation and inducing T-cell death, thus limiting T-cell expansion after activation. TGFβ1 is known to inhibit IL-2 signaling and the proliferation of T cells through multiple pathways. TGFβ1 inhibits the phosphorylation and activation of components of the JAK/STAT cascade downstream of IL-2R, as well as exerts inhibitory activity at the nuclear level on a subset of IL-2 target genes including c-Myc, cyclin D2, and cyclin. FIG. 5A: Proliferation of CTLL-2 stimulated with bFISTv3. FIG. 5B: Proliferation of CTLL-2 stimulated with bFISTv3 in the presence of active TGFβ1 (1 ng/mL). FIG. 5C: Proliferation of CTLL-2 stimulated with FIST (monovalent FIST). FIG. 5D: Proliferation of CTLL-2 stimulated with FIST in the presence of active TGFβ1 (1 ng/mL). FIG. 5E: Proliferation of CTLL-2 stimulated with IL-2. FIG. 5F: Proliferation of CTLL-2 stimulated IL-2 in the presence of active TGFβ1 (1 ng/mL). Data are shown as mean±SD, **p<0.005.

TABLE 2

IC50 values for CTLL-2 cell proliferation in response to the stimuli of fusion proteins or controls

| Molecule | IC50 | top | bottom | slope |
| --- | --- | --- | --- | --- |
| IL-2 | 0.057 | 106 | 1.04 | ~12 |
| IL2 + TβRII | 0.131 | 116 | 1.26 | 1.6 |
| FIST | 0.063 | 121 | 3.8 | 1.56 |
| bFISTv3 | 0.459 | 137 | 0.07 | 0.69 |

TABLE 3

IC50 values for the inhibition of TGFb1-dependent suppression of CTLL-2 cell proliferation

| Molecule | IC50 | top | bottom | slope |
| --- | --- | --- | --- | --- |

Example 5—bFIST Proliferation of Effector Memory T Cells and Terminal Differentiated Effector Memory Cells Exemplifying the fusion polypeptide compositions and methods disclosed herein, the following example demonstrates that the fusion polypeptides comprising an interleukin-2 (IL-2) polypeptide, a sTβRII receptor polypeptide, and a second sTβRII receptor polypeptide more effectively induces cytokine production and proliferation of both effector memory ($T_{EM}$) and terminal differentiated effector memory ($T_{EMRA}$) CD8 T cells.

Purified human T cells derived from PBMC-stimulated with CEF peptide pool (lyophilized mixture of 32 peptides from cytomegalovirus, Epstein-Barr virus, and influenza virus) were labeled with CellTrace™ Violet to track T cell proliferation (CellTrace™ mean fluorescence intensity (MFI) decreases as the cell proliferation increases). Proliferation of CD8$^+$ T cells, effector memory T cells (CCR7$^-$ CD45RA$^-$ CD62L$^-$ CD8$^+$ T cells), and terminal differentiated effector memory CD8 T cells (CCR7$^-$ CD45RA$^+$ CD62L$^-$ CD8$^+$ T cells) stimulated with equimolar concentration of bFISTv3, FIST (monovalent FIST), or IL-2.

Human PBMC from healthy donors were stimulated with CEF peptide pool overnight to induce the generation of viral antigen-specific T cells. T cells (CD3$^+$) were purified from PBMC derived from healthy donors by immunomagnetic negative selection using a Human T cell isolation kit. Purified T cells were labeled with CellTrace™ Violet before being stimulated with 5 nmoL of bFISTv3, FIST (monovalent FIST) and IL-2 for 48 hours. Stimulated T cells were labeled with fluorescence-conjugated antibodies specific for the memory T cell populations. After the incubation period, cell supernatants were collected to quantify the concentration of IFNγ by ELISA and the cells were collected to determine the cell proliferation of each T cell subpopulation by flow cytometry. bFISTv3 induces IFNγ production from T cells and significantly higher proliferation of both effector memory ($T_{EM}$) and terminal differentiated effector memory ($T_{EMRA}$) CD8 T cells (e.g., when compared to FIST).

Figure 6A:
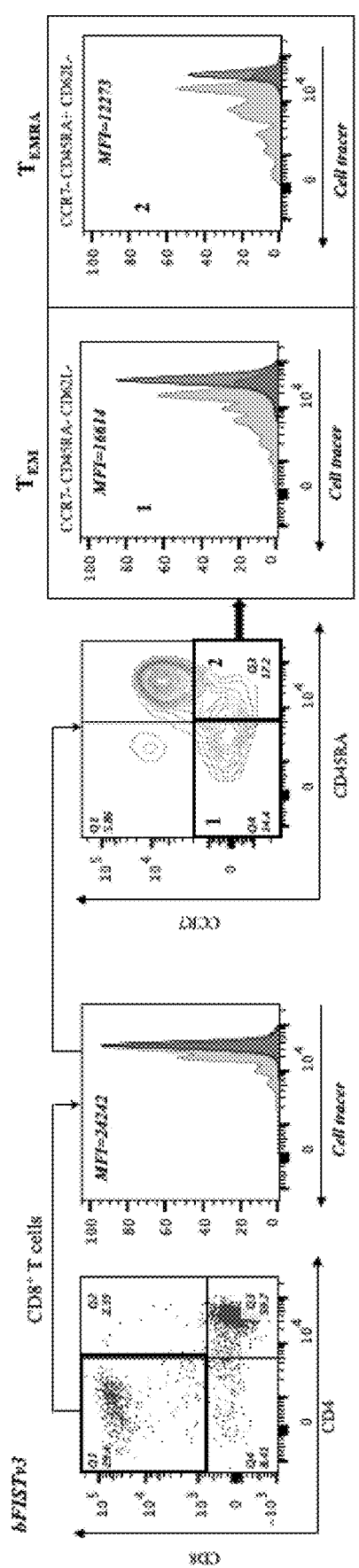
Figure 6B:
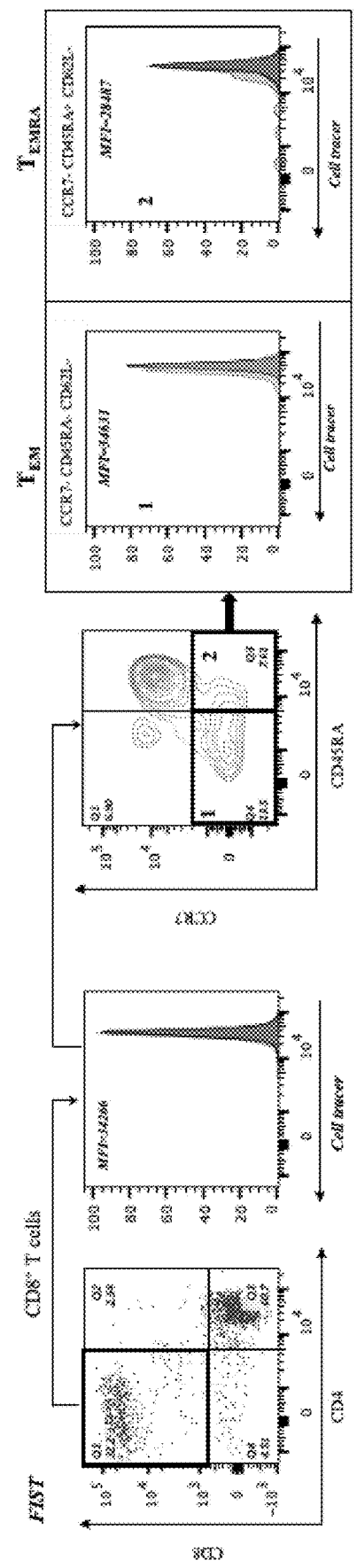
Figure 6F:
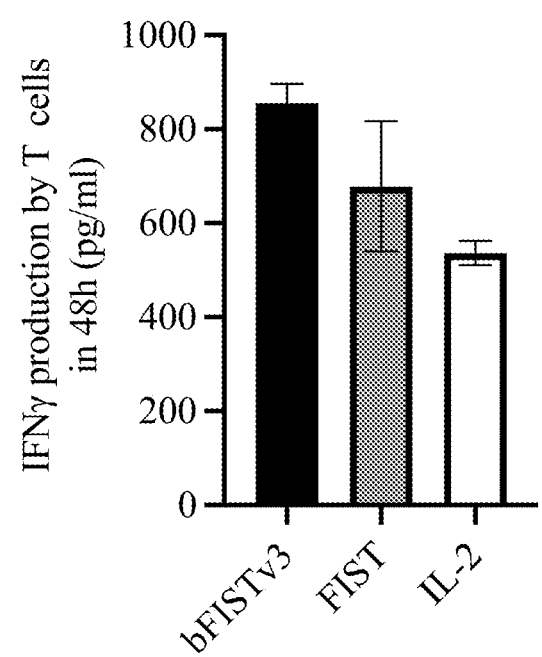

The effector memory T lymphocyte are antigen-primed lymphocytes that can confer rapid immune protection upon a second viral infection. The memory T cell subpopulations CCR7$^-$ can migrate to inflame tissues and exert immediate effector functions like cytotoxic activity against virus-infected cells. CCR7$^-$ memory CD8$^+$ T cells are characterized by the production of IFNγ and perforin-containing granules essential for their cytolytic activity against virus-infected cells. In particular, the perform expression is prominent in the terminal differentiated effector memory T cells (CD45RA$^+$CCR7$^-$ CD62L$^-$). FIG. 6A shows bFISTv3 induced proliferation of effector memory T cells ($T_{EM}$) and terminal differentiated effector memory cells ($T_{EMRA}$). FIG. 6B shows FIST induced proliferation of effector memory T cells ($T_{EM}$) and terminal differentiated effector memory cells ($T_{EMRA}$). FIG. 6C shows IL-2 induced proliferation of effector memory T cells ($T_{EM}$) and terminal differentiated effector memory cells ($T_{EMRA}$). FIG. 6D shows the average of CellTrace™ MFI values of stimulated $T_{EM}$ derived from two donors (a decrease in MFI denotes increased proliferation). FIG. 6E shows average CellTrace™ MFI values of stimulated $T_{EMRA}$ derived from two donors. FIG. 6F shows quantification of IFNγ production by T cells stimulated with bFISTv3, FIST (monovalent FIST), or IL-2 for 48 hours. Data are shown as mean±SD, * p<0.05.

Example 6—bFIST Reinforces the Th1 Phenotype of TCR-Stimulated T Cells and Enhances the Expression of Anti-Pathogen Cytokines and Proteases Exemplifying the fusion polypeptide compositions and methods disclosed herein, the following example demonstrates that the fusion polypeptides comprising an interleukin-2 (IL-2) polypeptide, a sTβRII receptor polypeptide, and a second sTβRII receptor polypeptide more effectively induces higher production of anti-pathogen cytokines crucial for the adaptive immune response against pathogens.

Figure 7A:
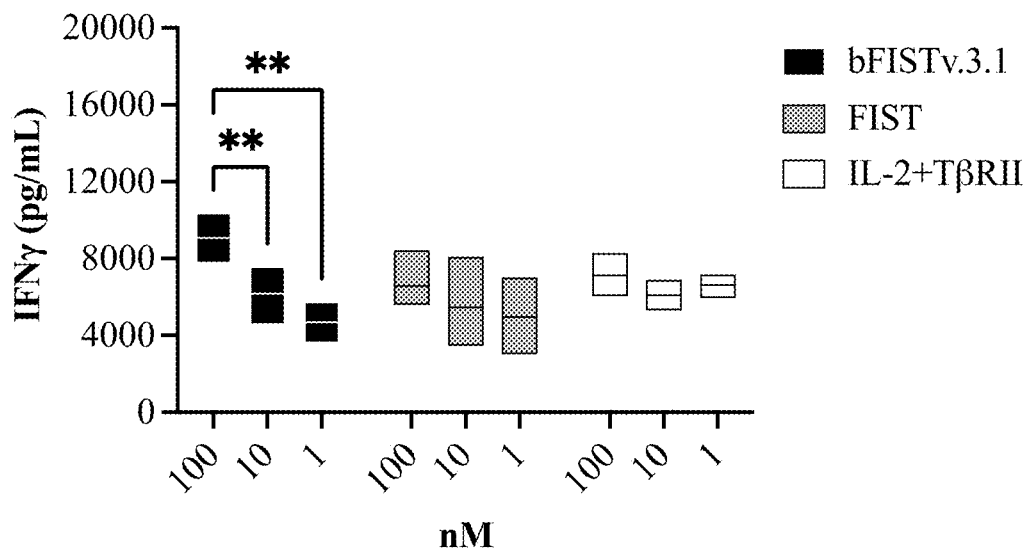
FIGS. 7A, 7B, 7C, 7D, and 7E show that bivalent FIST (bFIST) enhances the expression of anti-pathogen cytokines and proteases.
Figure 7B:
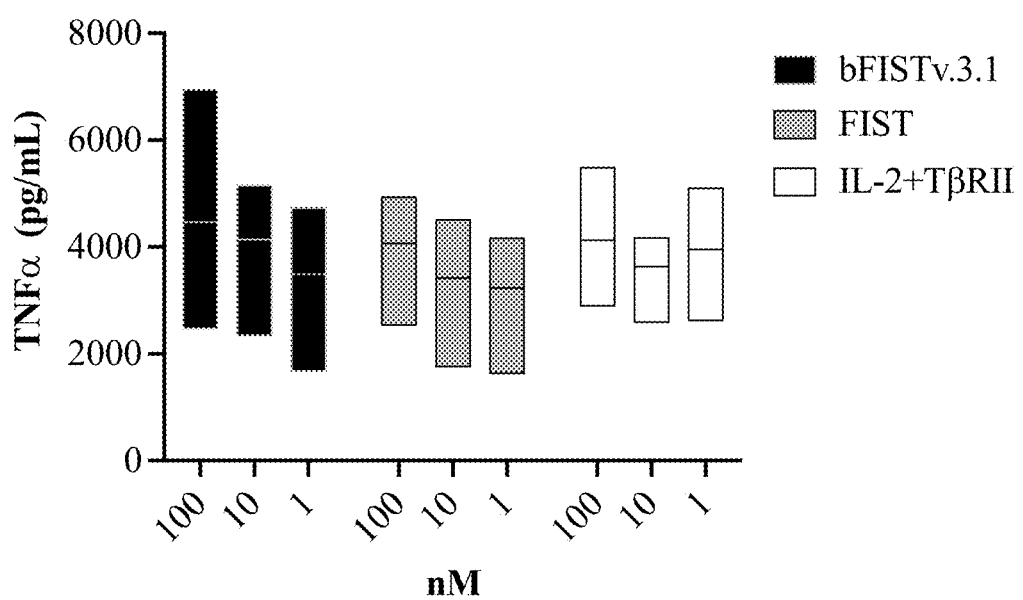
Figure 7C:
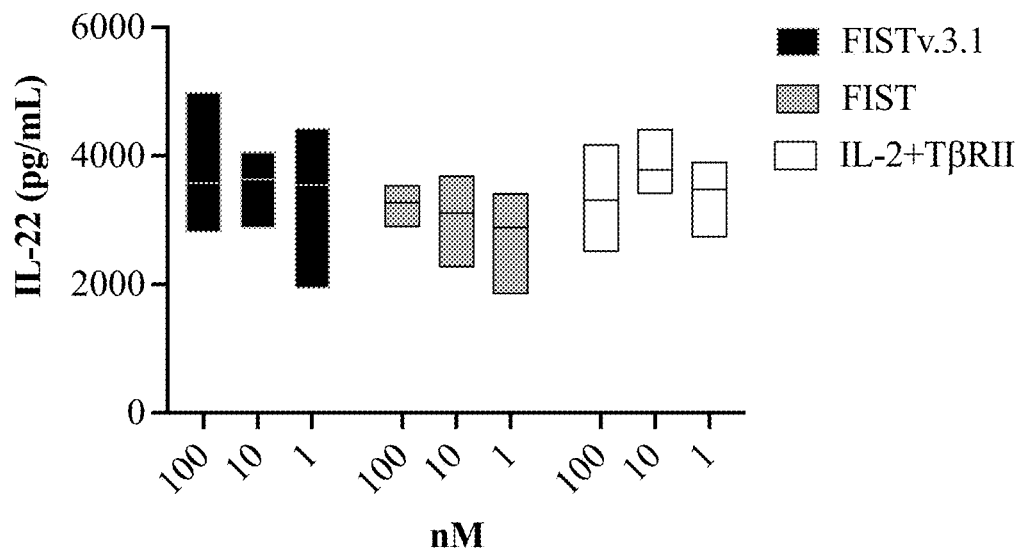
Figure 7D:
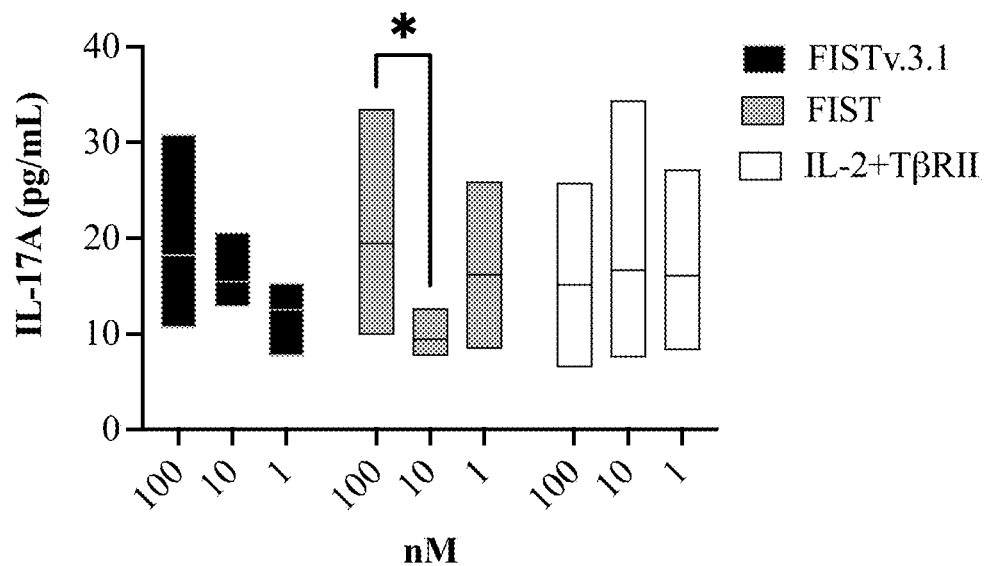
Figure 7E:
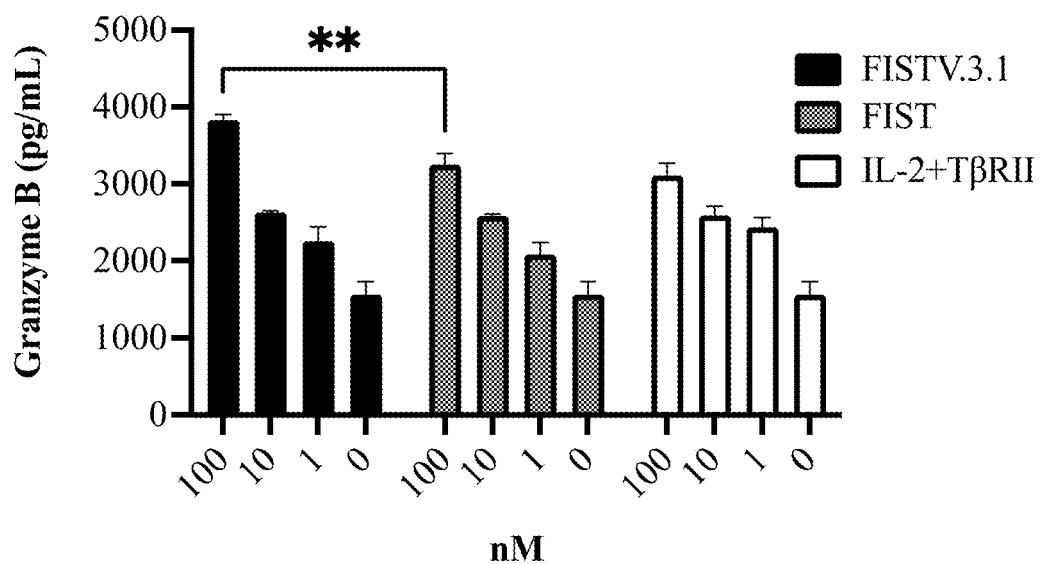

T cells (CD3$^+$) were purified from PBMC derived from healthy donors by immunomagnetic negative selection using a Human T cell isolation kit. Purified human T cells were stimulated with anti-CD3/CD28 antibodies and equimolar concentrations of the bivalent FIST (bFISTv.3.1), FIST (monovalent) and IL-2 for 48 hours. After the incubation period, cell supernatants were collected to quantify the concentration of Th polarizing cytokines by a multi-analyte flow assay. The concentration of 8 cytokines (IL-5, IL-13, IL-6, IFNγ, TNFα, IL-17A, IL-4 and IL-22) per sample were determined by flow cytometry. The concentration of granzyme B was quantified by ELISA. FIG. 7A, shows the quantification of IFNγ produced by T cells stimulated with CD3/CD28 and equimolar concentrations of bFISTv3.1, FIST and IL-2+ TβRII. FIG. 7B, shows the quantification of TNFα produced by T cells stimulated with CD3/CD28 and equimolar concentrations of bFISTv3.1, FIST and IL-2+ TβRII. FIG. 7C, shows the quantification of IL-22 produced by T cells stimulated with CD3/CD28 and equimolar concentrations of bFISTv3.1, FIST and IL-2+ TβRII. FIG. 7D, shows the quantification of IL-17A produced by T cells stimulated with CD3/CD28 and equimolar concentrations of bFISTv3.1, FIST and IL-2+ TβRII. FIG. 7E, shows the quantification of granzyme B produced by T cells stimulated with CD3/CD28 and equimolar concentrations of bFISTv3.1, FIST and IL-2+ TβRII quantified by ELISA. Data are shown as mean±SD, * p<0.05. The bivalent FIST (bFISTv.3.1) induces higher production of IFNγ, TNFα and IL-22 in a concentration dependent manner. In contrast, the monovalent FIST only induced IL-17A in a concentration dependent manner. Regarding to IL-5, IL-13, IL-6 and IL-4, no differences were detected (data not shown). These results demonstrate the superiority of bivalent FIST to reinforce the Th1 phenotype of TCR-stimulated T cells and enhance the effector functions of these cells such as the secretion of serine proteases (granzyme B) that mediate the cytotoxicity against pathogen-infected cells.

Both IFNγ and TNFα are known to control viral infections. IFNγ is crucial in the defense against intracellular pathogens such as mycobacteria and viruses. Similarly, IL-22 and IL-17 play an important role in protective immune responses against intracellular pathogens. IL-22 inhibits the growth of *mycobacterium* and decrease the number of regulatory T cells, which increase antigen-specific T cell responses. IL-22, IFNγ and IL-17 are adaptive cytokines involved in the development of protective immunity against pathogens.

Example 7—bFIST Prevents TGFβ1-Mediated Suppression of Primary NK Cell Proliferation and Increases IFNγ Production from these Cells Exemplifying the fusion polypeptide compositions and methods disclosed herein, the following example demonstrates that the fusion polypeptides comprising an interleukin-2 (IL-2) polypeptide, a sTβRII receptor polypeptide, and a second sTβRII receptor polypeptide more effectively inhibits and/or reduces TGFβ1-mediated suppression of NK cell proliferation and IFNγ production.

Human NK cells were purified from PBMC derived from healthy donors by immunomagnetic negative selection using a human NK cell isolation kit. Purified NK cells were labeled stimulated with equimolar concentrations (25 nM, 12.5 nM and 6.25 nM) of bFISTv3, FIST (monovalent FIST) and IL-2 for 5 days. After the incubation period, the cell culture supernatant was collected to quantify the concentration of IFNγ by ELISA. The number of viable cells was quantified with the fluorescence-based assay using a cell number/luminescence curve and the percentage of cell proliferation was calculated versus the positive control (IL-2+ TβRII) as the maximum stimulus of NK cell proliferation for these experimental conditions.

Figure 8A:
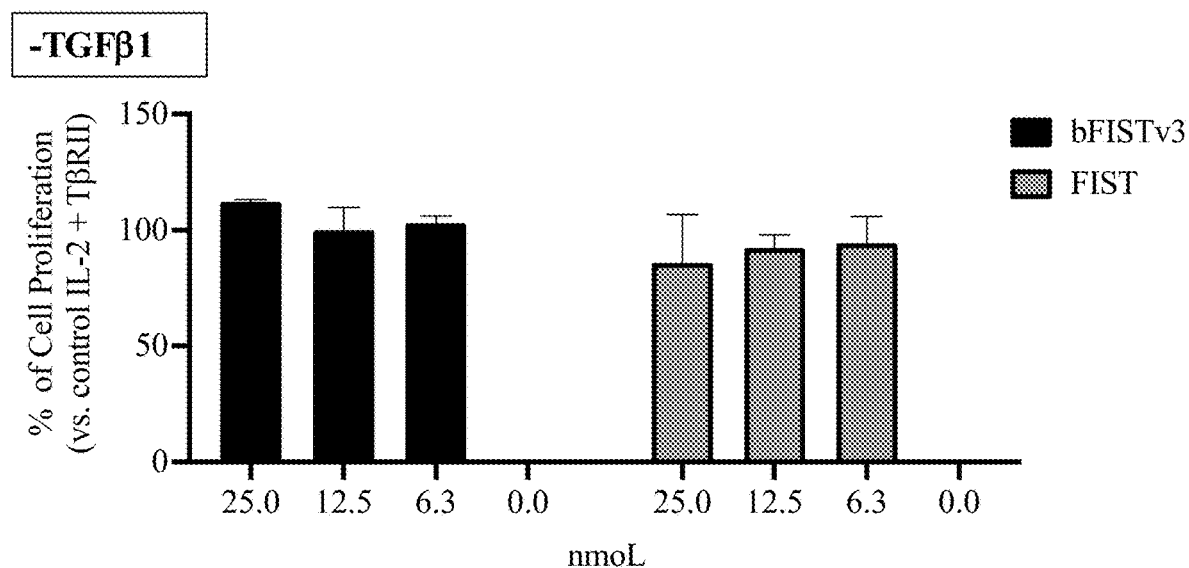
FIGS. 8A, 8B, 8C, 8D, and 8E show bivalent FIST inhibition and/or reduction of TGFβ 1-mediated suppression of primary NK cell proliferation and IFNγ and CXC10 production.
Figure 8B:
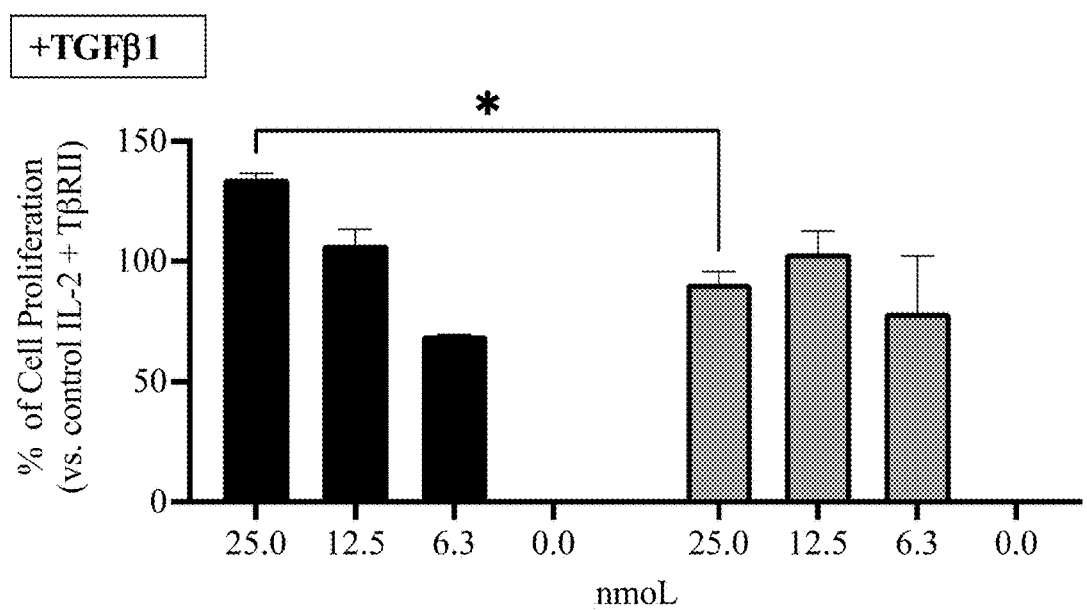
Figure 8C:
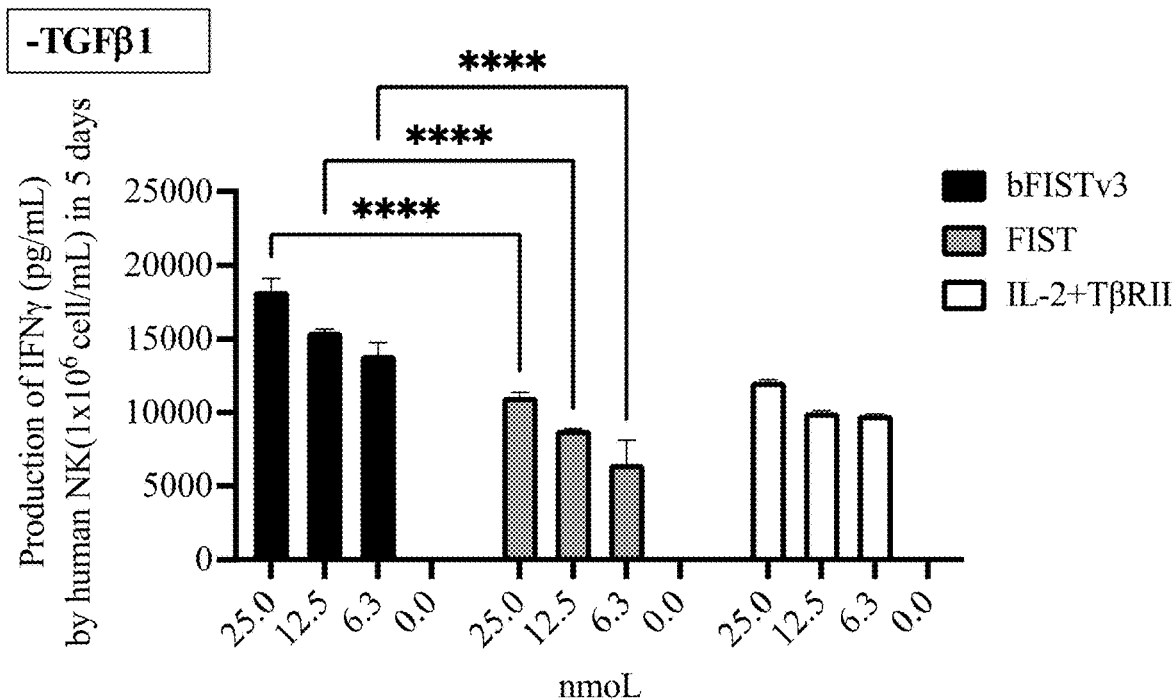
Figure 8D:
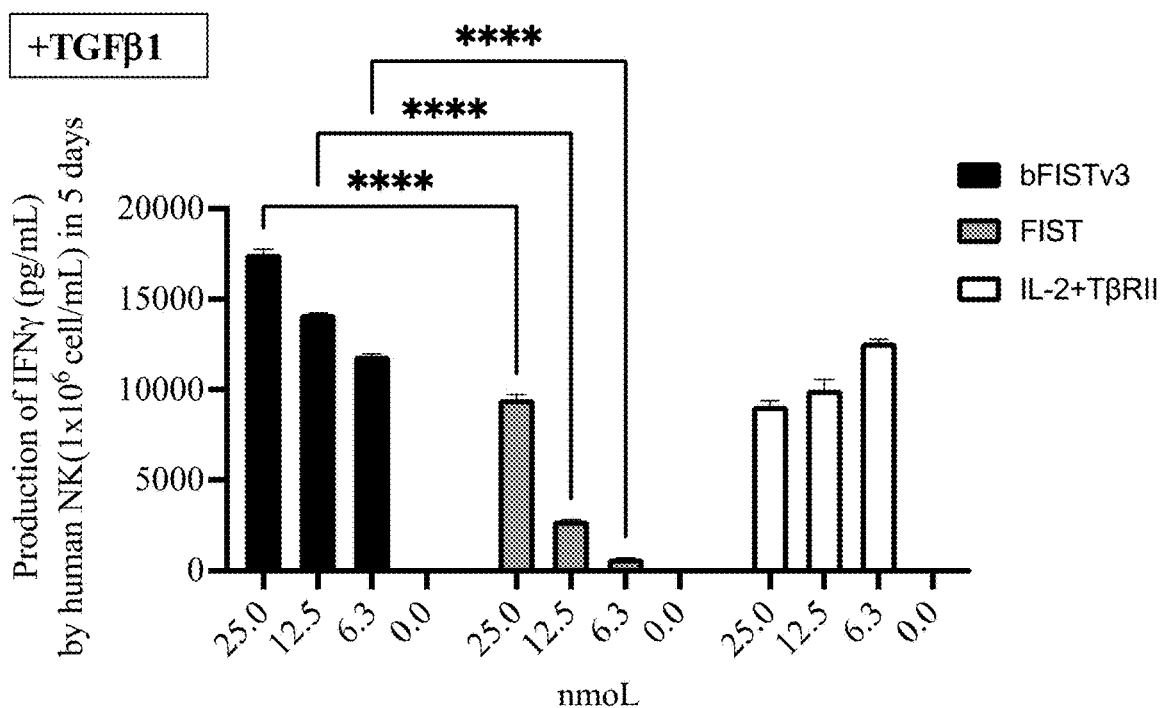
Figure 8E:
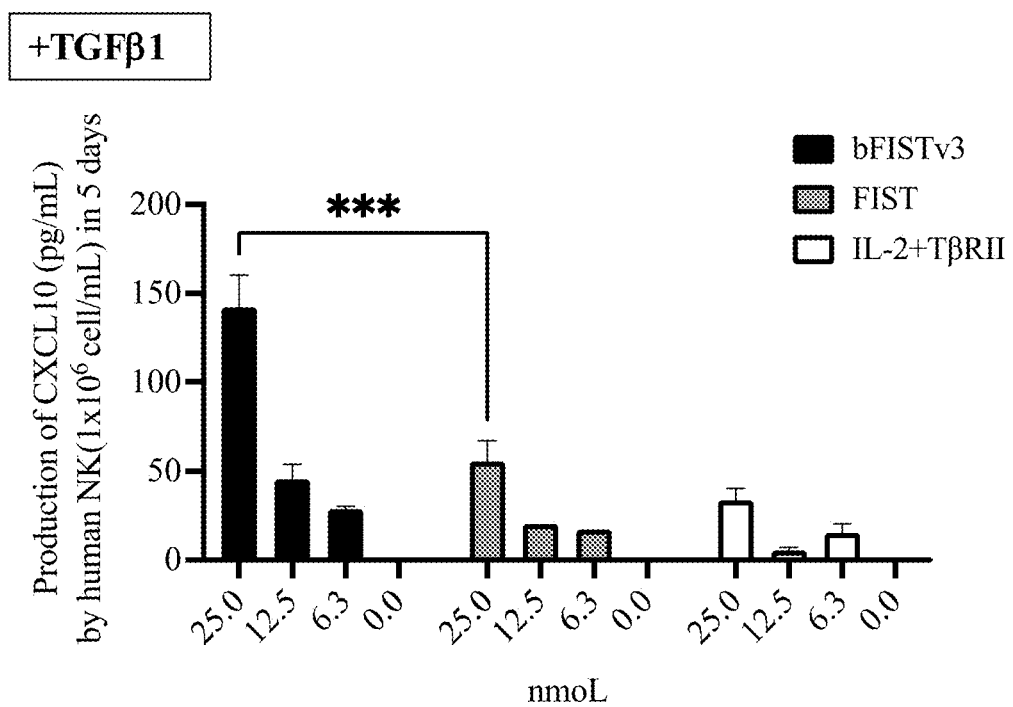

Purified human NK cells derived from peripheral mononuclear cells (PBMC) were stimulated with equimolar concentrations of bFISTv.3, FIST (monovalent FIST) or control (IL-2+ TβRII) for 5 days with or without active TGFβ1 (1 ng/mL). The culture supernatant was collected to quantify the amount of IFNγ by ELISA and the number of viable cells in culture was determined by quantitating the amount of ATP present, which indicates the metabolically active cells. FIG. 8A shows the percentage of proliferating NK cells in the absence of active TGFβ 1. FIG. 8B shows the percentage of proliferating NK cell in the presence of active TGFβ1. FIG. 8C shows the quantification of IFNγ produced by stimulated NK cells cultured in the absence of active TGFβ1. FIG. 8D, quantification of IFNγ produced by stimulated NK cells cultured with active TGFβ1 (1 ng/mL). CXCL10 mediates the mobilization of NK cells and virus-specific T lymphocytes to the infected tissues and enhances the effector functions of these cells against virus-infected cells. Bivalent FIST (bFISTv.3) effectively induces more CXCL10 production. FIG. 8E, quantification of CXCL10 produced by stimulated NK cells cultured with of active TGFβ1 (1 ng/mL). The data are representative of two independent experiments performed in duplicates. Statistic comparisons between bFISTv3 and FIST are indicated (data are shown as mean±SD, *p<0.05, p<0.005, *p<0.0005).

Example 8—bFIST Stimulates and Increases B Cell Maturation, Proliferation and IFNγ Production Exemplifying the fusion polypeptide compositions and methods disclosed herein, the following example demonstrates that the fusion polypeptides comprising an interleukin-2 (IL-2) polypeptide, a sTβRII receptor polypeptide, and a second sTβRII receptor polypeptide effectively (1) stimulates and/or increases higher B cell maturation, proliferation and IFNγ production and (2) reduces and/or inhibits TGFβ 1 suppression of B cell maturation, proliferation and IFNγ production.

Human B cells were purified from PBMC derived from healthy donors by immunomagnetic negative selection using a Human B cell isolation kit. Purified B cells were pre-labeled with CFSE to trace cell proliferation (the marker intensity decreases as the cell proliferation increases) before being stimulated with equimolar concentrations (20 nM, 10 nM and 5 nM) of bFISTv3, FIST and IL-2 for 5 days. After the incubation period, B cells were labeled with CD86 and HLA-DR and the percentages of double positive (CD86+ HLA-DR+) B cells and proliferation were quantified by flow cytometry. The cell culture supernatants were collected to quantify the concentration of IFNγ by ELISA. The statistic comparisons between bFISTv3 and FIST are indicated. Data are shown as mean±SD, *p<0.05, p<0.005, *p<0.0005.

Figure 9A:
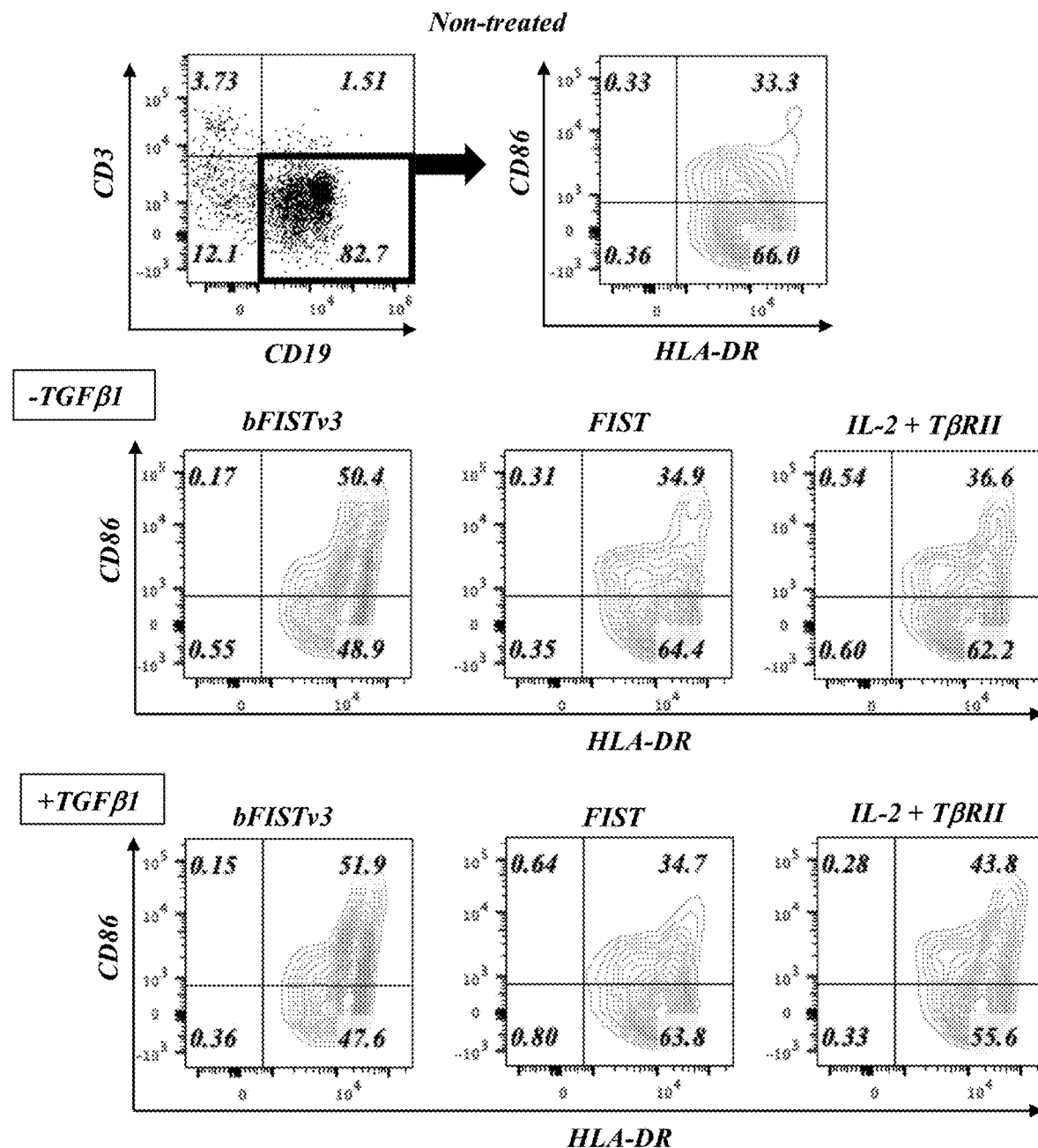
FIGS. 9A, 9B, 9C, and 9D show bivalent FIST (bFIST) more effectively inhibits and/or reduces TGFβ1-mediated suppression of B cell activation, proliferation, and IFNγ production.
Figure 9B:
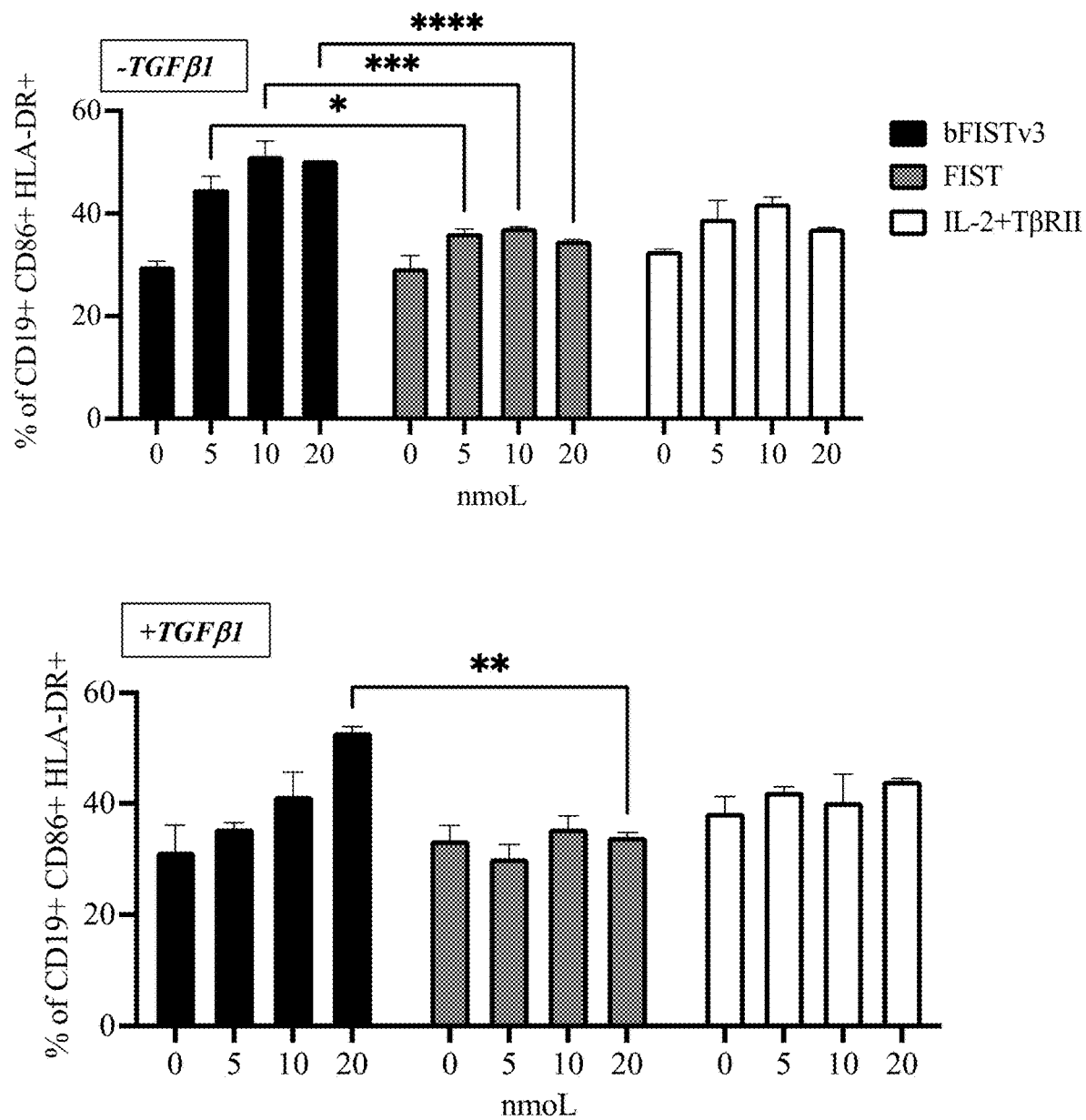

Bivalent FIST (bFISTv.3) more effectively increases and/or stimulates B cell activation, proliferation, and IFNγ production (e.g., compared to FIST or IL-2). Bivalent FIST also induces the upregulation of costimulatory molecule (CD86) and HLA-DR (MHC class II) molecule expression, which indicates a differentiation process of naïve B cells into effector cells with higher capacity for presentation of pathogenic antigens. Both antigen-presenting cells, B cells and dendritic cells contribute to restimulating antigen-specific memory T cells and promote long-term protection against pathogens. FIGS. 9A-D shows data from purified human B cells (CD19+ CD3−) derived from peripheral mononuclear cells (PBMC) were labeled with Carboxyfluorescein succinimidyl ester (CFSE) to trace cell proliferation before being stimulated with equimolar concentrations of bFISTv3, FIST (monovalent FIST) or, control (IL-2+ TβRII) for 5 days with and without active TGFβ1 (1 ng/mL). Stimulated B cells were labeled with conjugated antibodies specific for HLA-DR and CD86 to quantify the percentage of mature B cells by flow cytometry. FIG. 9A shows a comparison between bFISTv3 (20 nmoL) and FIST (20 nmoL) in the induction of double positive CD86+ HLA-DR+ B cells cultured with/without active TGFβ1. FIG. 9B shows the percentage of CD86+ HLA-DR+ B cells stimulated with 20, 10, 5 nmoL of bFISTv3, FIST (monovalent FIST) or, control (IL-2+

Figure 9C:
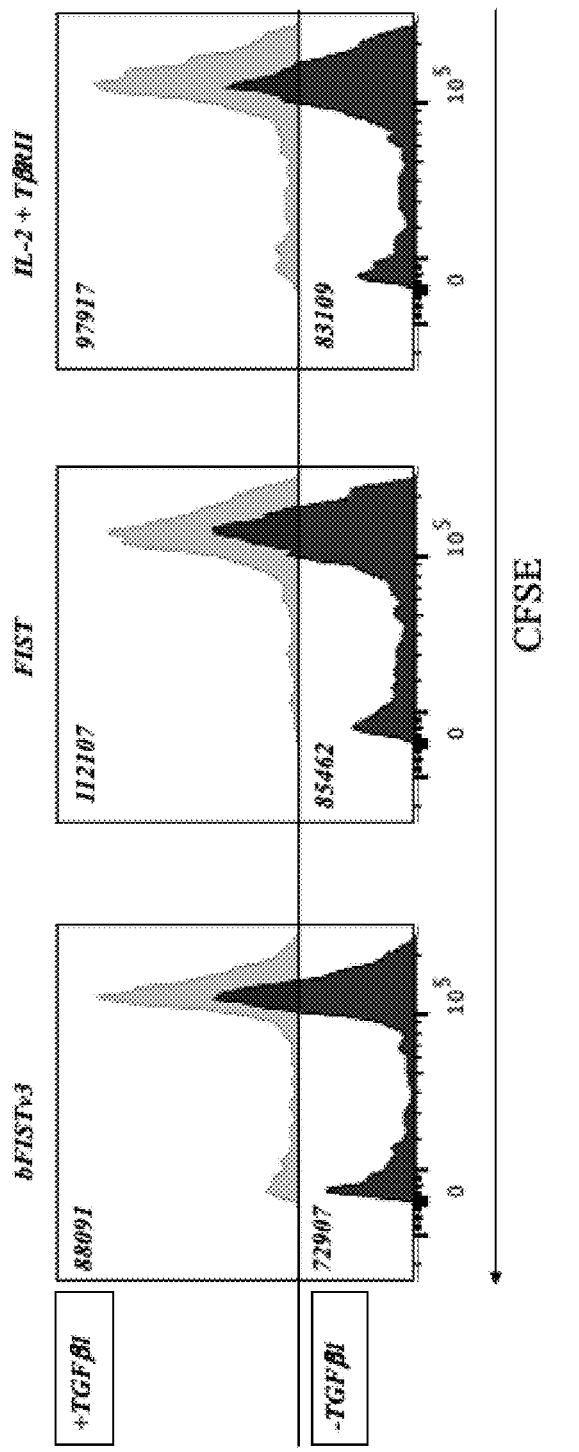
Figure 9D:
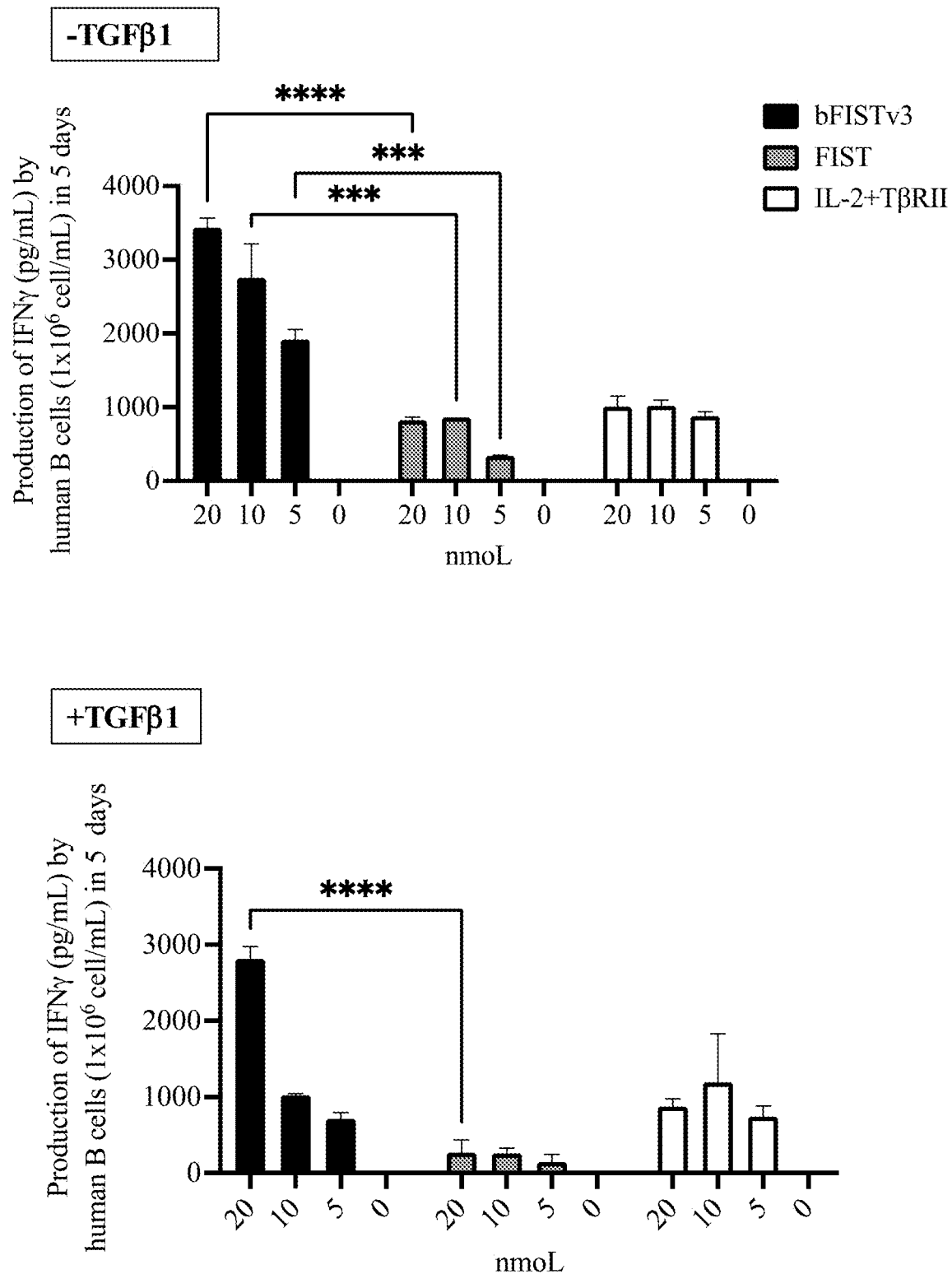

TβRII) cultured with/without active TGFβ1. FIG. 9C shows a comparison between bFISTv3 (20 nmoL) and FIST (20 nmoL) in the induction of CD86+HLA-DR+ B cell proliferation with/without active TGFβ1. The mean fluorescence intensity (MFI) values of CFSE (cell tracer) are indicated. FIG. 9D shows quantification of IFNγ production in the supernatant of stimulated B cells cultured with and without active TGFβ1.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

SEQUENCES

| SEQ ID NO | SEQUENCE | DESCRIPTION |
|---|---|---|
| 1 | MYRMQLLSCIALSLALVTNSAPTSSSTKKTQLQLEHLLLDLQMILNGI NNYKNPKLTRMLTFKFYMPKKATELKHLQCLEEELKPLEEVLNLAQ SKNFHLRPRDLISNINVIVLELKGSETTFMCEYADETATIVEFLNRWIT FCQSIISTLT | Human_IL2 |
| 2 | MYRMQLLSCIALSLALVTNSAPTSSSTKKTQLQLEHLLLDLQMILNGI NNYKNPKLTRMLTFKFYMPKKATELKHLQCLEEELKPLEEVLNLAQ SKNFHLRPRDLISNINVIVLELKGSETTFMCEYADETATIVEFLNRWIT FCQSIISTL | FIST_IL2 |
| 3 | MYRMQLLSCIALSLALVTNSAPTSSSTKKTQLQLEHLLLDLQMILNGI NNYKNPKLTRMLTAKFYMPKKATELKHLQCLEEELKPLEEVLNLAQ SKNFHLRPRDLISNINVIVLELKGSETTFMCEYADETATIVEFLNRWIT FCQSIISTL | FIST_IL2M IL-2 mutated F62A |
| 4 | MVLGTIDLCSCFSAGLPKTEANWVNVISDLKKIEDLIQSMHIDATLYT ESDVHPSCKVTAMKCFLLELQVISLESGDASIHDTVENLIILANNSLSS NGNVTESGCKECEELEEKNIKEFLQSFVHIVQMFINTS | Human_IL15 |
| 5 | CFSAGLPKTEANWVNVISDLKKIEDLIQSMHIDATLYTESDVHPSCK VTAMKCFLLELQVISLESGDASIHDTVENLIILANNSLSSNGNVTESG CKECEELEEKNIKEFLQSFVHIVQMFINTS | FIST_IL15 |
| 6 | MGRGLLRGLWPLHIVLWTRIASTIPPHVQKSVNNDMIVTDNNGAVK FPQLCKFCDVRFSTCDNQKSCMSNCSITSICEKPQEVCVAVWRKNDE NITLETVCHDPKLPYHDFILEDAASPKCIMKEKKKPGETFFMCSCSSD ECNDNIIFSEEYNTSNPDLLLVIFQVTGISLLPPLGVAISVIIIFYCYRVN RQQKLSSTWETGKTRKLMEFSEHCAIILEDDRSDISSTCANNINHNTE LLPIELDTLVGKGRFAEVYKAKLKQNTSEQFETVAVKIFPYEEYASW KTEKDIFSDINLKHENILQFLTAEERKTELGKQYWLITAFHAKGNLQE YLTRHVISWEDLRKLGSSLARGIAHLHSDHTPCGRPKMPIVHRDLKS SNILVKNDLTCCLCDFGLSLRLDPTLSVDDLANSGQVGTARYMAPE VLESRMNLENVESFKQTDVYSMALVLWEMTSRCNAVGEVKDYEPP FGSKVREHPCVESMKDNVLRDRGRPEIPSFWLNHQGIQMVCETLTEC WDHDPEARLTAQCVAERFSELEHLDRLSGRSCSEEKIPEDGSLNTTK | Human TGFBR |
| 7 | MGRGLLRGLWPLHIVLWTRIASTIPPHVQKSDVEMEAQKDEIICPSC NRTAHPLRHINNDMIVTDNNGAVKFPQLCKFCDVRFSTCDNQKSCM SNCSITSICEKPQEVCVAVWRKNDENITLETVCHDPKLPYHDFILEDA ASPKCIMKEKKKPGETFFMCSCSSDECNDNIIFSEEYNTSNPDLLLVIF QVTGISLLPPLGVAISVIIIFYCYRVNRQQKLSSTWETGKTRKLMEFSE HCAIILEDDRSDISSTCANNINHNTELLPIELDTLVGKGRFAEVYKAK LKQNTSEQFETVAVKIFPYEEYASWKTEKDIFSDINLKHENILQFLTA EERKTELGKQYWLITAFHAKGNLQEYLTRHVISWEDLRKLGSSLAR GIAHLHSDHTPCGRPKMPIVHRDLKSSNILVKNDLTCCLCDFGLSLRL DPTLSVDDLANSGQVGTARYMAPEVLESRMNLENVESFKQTDVYS MALVLWEMTSRCNAVGEVKDYEPPFGSKVREHPCVESMKDNVLRD RGRPEIPSFWLNHQGIQMVCETLTECWDHDPEARLTAQCVAERFSEL EHLDRLSGRSCSEEKIPEDGSLNTTK | Human TGFBR long |
| 8 | IPPHVQKSVNNDMIVTDNNGAVKLPQLCKFCDVRFSTCDNQKSCMS NCSITSICEKPHEVCVAVWRKNDENITLETVCHDPKLTYHGFTLEDA ASPKCVMKEKKKPGETFFMCSCSADECNDNIIFSEDYNTSNPD | bFIST_TGFBR_ short |
| 9 | IPPHVQKSDVEMEAQKGEMICVTCNRTAHPLKHVNNDMIVTDNNG AVKLPQLCKFCDVRFSTCDNQKSCMSNCSITSICEKPQEVCVAVWRK NDENITLETVCHDPKLTYHGFTLEDAASPKCVMKEKKKPGETFFMC SCSSDECNDNIIFSEDYNTSNPD | bFIST_TGFBR_ long |
| 10 | MYRMQLLSCIALSLALVTNSAPTSSSTKKTQLQLEHLLLDLQMILNGI NNYKNPKLTRMLTAKFYMPKKATELKHLQCLEEELKPLEEVLNLAQ SKNFHLRPRDLISNINVIVLELKGSETTFMCEYADETATIVEFLNRWIT FCQSIISTLQKSVNNDMIVTDNNGAVKLPQLCKFCDVRFSTCDNQKS | bFISTv.2 |

| SEQ ID NO | SEQUENCE | DESCRIPTION |
|---|---|---|
| | CMSNCSITSICEKPHEVCVAVWRKNDENITLETVCHDPKLTYHGFTL EDAASPKCVMKEKKKPGETFFMCSCSADECNDNIIFIPPHVQKSVNN DMIVTDNNGAVKLPQLCKFCDVRFSTCDNQKSCMSNCSITSICEKPH EVCVAVWRKNDENITLETVCHDPKLTYHGFTLEDAASPKCVMKEK KKPGETFFMCSCSADECNDNIIFSEDYNTSNPD | |
| 11 | MYRMQLLSCIALSLALVTNSAPTSSSTKKTQLQLEHLLLDLQMILNGI NNYKNPKLTRMLTFKFYMPKKATELKHLQCLEEELKPLEEVLNLAQ SKNFHLRPRDLISNINIVIVLELKGSETTFMCEYADETATIVEFLNRWIT FCQSIISTLIPPHVQKSVNNDMIVTDNNGAVKLPQLCKFCDVRFSTCD NQKSCMSNCSITSICEKPHEVCVAVWRKNDENITLETVCHDPKLTYH GFTLEDAASPKCVMKEKKKPGETFFMCSCSADECNDNIIFSEDYNTS NPDIPPHVQKSVNNDMIVTDNNGAVKLPQLCKFCDVRFSTCDNQKS CMSNCSITSICEKPHEVCVAVWRKNDENITLETVCHDPKLTYHGFTL EDAASPKCVMKEKKKPGETFFMCSCSADECNDNIIFSEDYNTSNPD | bFISTv.2.1 |
| 12 | MYRMQLLSCIALSLALVTNSAPTSSSTKKTQLQLEHLLLDLQMILNGI NNYKNPKLTRMLTAKFYMPKKATELKHLQCLEEELKPLEEVLNLAQ SKNFHLRPRDLISNINIVIVLELKGSETTFMCEYADETATIVEFLNRWIT FCQSIISTLQKSDVEMEAQKGEMICVTCNRTAHPLKHVNNDMIVTDN NGAVKLPQLCKFCDVRFSTCDNQKSCMSNCSITSICEKPQEVCVAV WRKNDENITLETVCHDPKLTYHGFTLEDAASPKCVMKEKKKPGETF FMCSCSSDECNDNIIFIPPHVQKSVNNDMIVTDNNGAVKLPQLCKFC DVRFSTCDNQKSCMSNCSITSICEKPHEVCVAVWRKNDENITLETVC HDPKLTYHGFTLEDAASPKCVMKEKKKPGETFFMCSCSADECNDNII FSEDYNTSNPD | bFISTv.3 |
| 13 | MYRMQLLSCIALSLALVTNSAPTSSSTKKTQLQLEHLLLDLQMILNGI NNYKNPKLTRMLTFKFYMPKKATELKHLQCLEEELKPLEEVLNLAQ SKNFHLRPRDLISNINIVIVLELKGSETTFMCEYADETATIVEFLNRWIT FCQSIISTLQIPPHVKSDVEMEAQKGEMICVTCNRTAHPLKHVNNDM IVTDNNGAVKLPQLCKFCDVRFSTCDNQKSCMSNCSITSICEKPQEV CVAVWRKNDENITLETVCHDPKLTYHGFTLEDAASPKCVMKEKKK PGETFFMCSCSSDECNDNIIFSEDYNTSNPDIPPHVQKSVNNDMIVTD NNGAVKLPQLCKFCDVRFSTCDNQKSCMSNCSITSICEKPHEVCVAV WRKNDENITLETVCHDPKLTYHGFTLEDAASPKCVMKEKKKPGETF FMCSCSADECNDNIIFSEDYNTSNPD | bFISTv.3.1 |
| 14 | MYRMQLLSCIALSLALVTNSAPTSSSTKKTQLQLEHLLLDLQMILNGI NNYKNPKLTRMLTAKFYMPKKATELKHLQCLEEELKPLEEVLNLAQ SKNFHLRPRDLISNINIVIVLELKGSETTFMCEYADETATIVEFLNRWIT FCQSIISTLQKSVNNDMIVTDNNGAVKLPQLCKFCDVRFSTCDNQKS CMSNCSITSICEKPHEVCVAVWRKNDENITLETVCHDPKLTYHGFTL EDAASPKCVMKEKKKPGETFFMCSCSADECNDNIIFIPPHVQKSDVE MEAQKGEMICVTCNRTAHPLKHVNNDMIVTDNNGAVKLPQLCKFC DVRFSTCDNQKSCMSNCSITSICEKPQEVCVAVWRKNDENITLETVC HDPKLTYHGFTLEDAASPKCVMKEKKKPGETFFMCSCSSDECNDNII FSEDYNTSNPD | bFISTv.4 |
| 15 | MYRMQLLSCIALSLALVTNSAPTSSSTKKTQLQLEHLLLDLQMILNGI NNYKNPKLTRMLTFKFYMPKKATELKHLQCLEEELKPLEEVLNLAQ SKNFHLRPRDLISNINIVIVLELKGSETTFMCEYADETATIVEFLNRWIT FCQSIISTLIPPHVQKSVNNDMIVTDNNGAVKLPQLCKFCDVRFSTCD NQKSCMSNCSITSICEKPHEVCVAVWRKNDENITLETVCHDPKLTYH GFTLEDAASPKCVMKEKKKPGETFFMCSCSADECNDNIIFSEDYNTS NPDIPPHVQKSDVEMEAQKGEMICVTCNRTAHPLKHVNNDMIVTDN NGAVKLPQLCKFCDVRFSTCDNQKSCMSNCSITSICEKPQEVCVAV WRKNDENITLETVCHDPKLTYHGFTLEDAASPKCVMKEKKKPGETF FMCSCSSDECNDNIIFSEDYNTSNPD | bFISTv.4.1 |
| 16 | MYRMQLLSCIALSLALVTNSAPTSSSTKKTQLQLEHLLLDLQMILNGI NNYKNPKLTRMLTAKFYMPKKATELKHLQCLEEELKPLEEVLNLAQ SKNFHLRPRDLISNINIVIVLELKGSETTFMCEYADETATIVEFLNRWIT FCQSIISTLQKSDVEMEAQKGEMICVTCNRTAHPLKHVNNDMIVTDN NGAVKLPQLCKFCDVRFSTCDNQKSCMSNCSITSICEKPQEVCVAV WRKNDENITLETVCHDPKLTYHGFTLEDAASPKCVMKEKKKPGETF FMCSCSSDECNDNIIFIPPHVKSDVEMEAQKGEMICVTCNRTAHPLK HVNNDMIVTDNNGAVKLPQLCKFCDVRFSTCDNQKSCMSNCSITSIC EKPQEVCVAVWRKNDENITLETVCHDPKLTYHGFTLEDAASPKCVM KEKKKPGETFFMCSCSSDECNDNIIFSEDYNTSNPD | bFISTv.5 |
| 17 | MYRMQLLSCIALSLALVTNSAPTSSSTKKTQLQLEHLLLDLQMILNGI NNYKNPKLTRMLTFKFYMPKKATELKHLQCLEEELKPLEEVLNLAQ SKNFHLRPRDLISNINIVIVLELKGSETTFMCEYADETATIVEFLNRWIT | bFISTv.5.1 |

-continued

| SEQ ID NO | SEQUENCE | DESCRIPTION |
|---|---|---|
| | FCQSIISTLQIPPHVKSDVEMEAQKGEMICVTCNRTAHPLKHVNNDM IVTDNNGAVKLPQLCKFCDVRFSTCDNQKSCMSNCSITSICEKPQEV CVAVWRKNDENITLETVCHDPKLTYHGFTLEDAASPKCVMKEKKK PGETFFMCSCSSDECNDNIIFSEDYNTSNPDIPPHVKSDVEMEAQKGE MICVTCNRTAHPLKHVNNDMIVTDNNGAVKLPQLCKFCDVRFSTCD NQKSCMSNCSITSICEKPQEVCVAVWRKNDENITLETVCHDPKLTYH GFTLEDAASPKCVMKEKKKPGETFFMCSCSSDECNDNIIFSEDYNTS NPD | |
| 18 | MYRMQLLSCIALSLALVTNSISAMVRSVECPPCPAPPVAGPSVFLFPP KPKDTLMISRTPEVTCVVVDVSHEDPEVKFNWYVDGVEVHNAKTK PREEQYNSTYRVVSVLTVLHQDWLNGKEYKCKVSNKGLPSSIEKTIS KAKGQPREPQVYTLPPSREEMTKNQVSLTCLVKGFYPSDIAVEWESN GQPENNYKTTPPVLDSDGSFFLYSKLTVDKSRWQQGNVFSCSVMHE ALHNHYTQKSLSLSPGKAPTSSSTKKTQLQLEHLLLDLQMILNGINN YKNPKLTRMLTAKFYMPKKATELKHLQCLEEELKPLEEVLNLAQSK NFHLRPRDLISNINVIVLELKGSETTFMCEYADETATIVEFLNRWITFC QSIISTLQKSDVEMEAQKGEMICVTCNRTAHPLKHVNNDMIVTDNN GAVKLPQLCKFCDVRFSTCDNQKSCMSNCSITSICEKPQEVCVAVWR KNDENITLETVCHDPKLTYHGFTLEDAASPKCVMKEKKKPGETFFM CSCSSDECNDNIIFIPPHVQKSVNNDMIVTDNNGAVKLPQLCKFCDV RFSTCDNQKSCMSNCSITSICEKPHEVCVAVWRKNDENITLETVCHD PKLTYHGFTLEDAASPKCVMKEKKKPGETFFMCSCSADECNDNIIFS EDYNTSNPD | bFISTv.6 |
| 19 | MYRMQLLSCIALSLALVTNSISAMVRSVECPPCPAPPVAGPSVFLFPP KPKDTLMISRTPEVTCVVVDVSHEDPEVKFNWYVDGVEVHNAKTK PREEQYNSTYRVVSVLTVLHQDWLNGKEYKCKVSNKGLPSSIEKTIS KAKGQPREPQVYTLPPSREEMTKNQVSLTCLVKGFYPSDIAVEWESN GQPENNYKTTPPVLDSDGSFFLYSKLTVDKSRWQQGNVFSCSVMHE ALHNHYTQKSLSLSPGKAPTSSSTKKTQLQLEHLLLDLQMILNGINN YKNPKLTRMLTAKFYMPKKATELKHLQCLEEELKPLEEVLNLAQSK NFHLRPRDLISNINVIVLELKGSETTFMCEYADETATIVEFLNRWITFC QSIISTLQKSVNNDMIVTDNNGAVKLPQLCKFCDVRFSTCDNQKSCM SNCSITSICEKPHEVCVAVWRKNDENITLETVCHDPKLTYHGFTLED AASPKCVMKEKKKPGETFFMCSCSADECNDNIIFIPPHVQKSVNNDM IVTDNNGAVKLPQLCKFCDVRFSTCDNQKSCMSNCSITSICEKPHEV CVAVWRKNDENITLETVCHDPKLTYHGFTLEDAASPKCVMKEKKK PGETFFMCSCSADECNDNIIFSEDYNTSNPD | bFISTv.7 |
| 20 | MYRMQLLSCIALSLALVTNSIPPHVQKSVNNDMIVTDNNGAVKLPQ LCKFCDVRFSTCDNQKSCMSNCSITSICEKPHEVCVAVWRKNDENIT LETVCHDPKLTYHGFTLEDAASPKCVMKEKKKPGETFFMCSCSADE CNDNIIFSEDYNTSNPDAPTSSSTKKTQLQLEHLLLDLQMILNGINNY KNPKLTRMLTAKFYMPKKATELKHLQCLEEELKPLEEVLNLAQSKN FHLRPRDLISNINVIVLELKGSETTFMCEYADETATIVEFLNRWITFCQ SIISTLQKSVNNDMIVTDNNGAVKLPQLCKFCDVRFSTCDNQKSCMS NCSITSICEKPHEVCVAVWRKNDENITLETVCHDPKLTYHGFTLEDA ASPKCVMKEKKKPGETFFMCSCSADECNDNIIFSEDYNTSNPD | bFISTv.8 |
| 21 | MYRMQLLSCIALSLALVTNSIPPHVQKSVNNDMIVTDNNGAVKLPQ LCKFCDVRFSTCDNQKSCMSNCSITSICEKPHEVCVAVWRKNDENIT LETVCHDPKLTYHGFTLEDAASPKCVMKEKKKPGETFFMCSCSADE CNDNIIFSEDYNTSNPDAPTSSSTKKTQLQLEHLLLDLQMILNGINNY KNPKLTRMLTAKFYMPKKATELKHLQCLEEELKPLEEVLNLAQSKN FHLRPRDLISNINVIVLELKGSETTFMCEYADETATIVEFLNRWITFCQ SIISTLQKSDVEMEAQKGEMICVTCNRTAHPLKHVNNDMIVTDNNG AVKLPQLCKFCDVRFSTCDNQKSCMSNCSITSICEKPQEVCVAVWRK NDENITLETVCHDPKLTYHGFTLEDAASPKCVMKEKKKPGETFFMC SCSSDECNDNIIFSEDYNTSNPD | bFISTv.9 |
| 22 | MYRMQLLSCIALSLALVTNSIPPHVKSDVEMEAQKGEMICVTCNRT AHPLKHVNNDMIVTDNNGAVKLPQLCKFCDVRFSTCDNQKSCMSN CSITSICEKPQEVCVAVWRKNDENITLETVCHDPKLTYHGFTLEDAA SPKCVMKEKKKPGETFFMCSCSSDECNDNIIFSEDYNTSNPDAPTSSS TKKTQLQLEHLLLDLQMILNGINNYKNPKLTRMLTAKFYMPKKATE LKHLQCLEEELKPLEEVLNLAQSKNFHLRPRDLISNINVIVLELKGSE TTFMCEYADETATIVEFLNRWITFCQSIISTLQKSDVEMEAQKGEMIC VTCNRTAHPLKHVNNDMIVTDNNGAVKLPQLCKFCDVRFSTCDNQ KSCMSNCSITSICEKPQEVCVAVWRKNDENITLETVCHDPKLTYHGF TLEDAASPKCVMKEKKKPGETFFMCSCSSDECNDNIIFSEDYNTSNP D | bFISTv.10 |

| SEQ ID NO | SEQUENCE | DESCRIPTION |
|---|---|---|
| 23 | MYRMQLLSCIALSLALVTNSAPTSSSTKKTQLQLEHLLLDLQMILNGI NNYKNPKLTRMLTFKFYMPKKATELKHLQCLEEELKPLEEVLNLAQ SKNFHLRPRDLISNINVIVLELKGSETTFMCEYADETATIVEFLNRWIT FCQSIISTLQKSDVEMEAQKGEMICVTCNRTAHPLKHVNNDMIVTDN NGAVKLPQLCKFCDVRFSTCDNQKSCMSNCSITSICEKPQEVCVAV WRKNDENITLETVCHDPKLTYHGFTLEDAASPKCVMKEKKKPGETF FMCSCSSDECNDNIIFSEDYNTSNPD | FISTv.11 |
| 24 | MYRMQLLSCIALSLALVTNSAPTSSSTKKTQLQLEHLLLDLQMILNGI NNYKNPKLTRMLTAKFYMPKKATELKHLQCLEEELKPLEEVLNLAQ SKNFHLRPRDLISNINVIVLELKGSETTFMCEYADETATIVEFLNRWIT FCQSIISTLQKSDVEMEAQKGEMICVTCNRTAHPLKHVNNDMIVTDN NGAVKLPQLCKFCDVRFSTCDNQKSCMSNCSITSICEKPQEVCVAV WRKNDENITLETVCHDPKLTYHGFTLEDAASPKCVMKEKKKPGETF FMCSCSSDECNDNIIFSEDYNTSNPD | FISTv.12 |
| 25 | MYRMQLLSCIALSLALVTNSAPTSSSTKKTQLQLEHLLLDLQMILNGI NNYKNPKLTRMLTAKFYMPKKATELKHLQCLEEELKPLEEVLNLAQ SKNFHLRPRDLISNINVIVLELKGSETTFMCEYADETATIVEFLNRWIT FCQSIISTLQKSVNNDMIVTDNNGAVKLPQLCKFCDVRFSTCDNQKS CMSNCSITSICEKPHEVCVAVWRKNDENITLETVCHDPKLTYHGFTL EDAASPKCVMKEKKKPGETFFMCSCSADECNDNIIFSEDYNTSNPD | FISTv.13 |

The invention claimed is:

1. A method of treating or ameliorating a pathogenic infection in a subject, the method comprising administering to the subject a therapeutically effective amount of a fusion polypeptide comprising:
   an interleukin-2 (IL 2) polypeptide or a fragment thereof comprising an IL-2 receptor binding domain;
   a first soluble TGFβ receptor II (sTβRII) polypeptide or a fragment thereof comprising a ligand binding domain; and
   a second soluble TGFβ receptor II (sTβRII) polypeptide or a fragment thereof comprising a ligand binding domain,
   thereby treating or ameliorating the pathogenic infection in the subject.

2. The method of claim 1, wherein the pathogenic infection comprises an intracellular pathogen.

3. The method of claim 1, wherein the IL-2 polypeptide comprises SEQ ID NO: 2 or 3, or a fragment thereof comprising an IL-2 receptor binding domain.

4. The method of claim 1, wherein the IL-2 polypeptide comprises an amino acid sequence having greater than about 80% sequence identity to SEQ ID NO: 2.

5. The method of claim 1, wherein the first sTβRII polypeptide, the second sTβRII polypeptide, or both, comprise amino acid sequence having greater than about 80% sequence identity to SEQ ID NO: 8 or SEQ ID NO: 9.

6. The method of claim 1, wherein the first sTβRII polypeptide, the second sTβRII polypeptide, or both, bind a TGFβ1 polypeptide, a TGFβ2 polypeptide, a TGFβ3 polypeptide, or any combination thereof.

7. The method of claim 1, wherein the first sTβRII polypeptide and the second sTβRII polypeptide bind a TGFβ1 polypeptide.

8. The method of claim 1, wherein the fusion polypeptide comprises an amino acid sequence having at least about 80% sequence identity to any one of SEQ ID NOs: 10-25.

9. The method of claim 1, wherein the pathogenic infection is an intracellular bacterial infection.

10. The method of claim 1, wherein the pathogenic infection is a viral infection.

11. The method of claim 1, wherein the administering comprises administering the fusion polypeptide to the subject by systemic administration.

12. The method of claim 1, wherein the administering comprises administering the fusion polypeptide to the subject by intravenous administration.

13. The method of claim 1, wherein the administering comprises administering a pharmaceutical composition comprising the fusion polypeptide to the subject.

14. The method of claim 13, wherein the pharmaceutical composition comprises one or more pharmaceutically acceptable excipients, carriers, diluents, or any combination thereof.

15. The method of claim 1, wherein the subject is a human.

* * * * *

SEQUENCE LISTING

<160> NUMBER OF SEQ ID NOS: 25

<210> SEQ ID NO 1
<211> LENGTH: 153
<212> TYPE: PRT
<213> ORGANISM: Homo sapiens

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 2
<211> LENGTH: 152
<212> TYPE: PRT
<213> ORGANISM: Homo sapiens -continued

<400> SEQUENCE: 2

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu
145                 150
```

<210> SEQ ID NO 3
<211> LENGTH: 152
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Ala Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu
145                 150
```

<210> SEQ ID NO 4
<211> LENGTH: 135
<212> TYPE: PRT
<213> ORGANISM: Homo sapiens

<400> SEQUENCE: 4

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser
    130                 135

<210> SEQ ID NO 5
<211> LENGTH: 125
<212> TYPE: PRT
<213> ORGANISM: Homo sapiens

<400> SEQUENCE: 5

Cys Phe Ser Ala Gly Leu Pro Lys Thr Glu Ala Asn Trp Val Asn Val
1               5                   10                  15

Ile Ser Asp Leu Lys Lys Ile Glu Asp Leu Ile Gln Ser Met His Ile
            20                  25                  30

Asp Ala Thr Leu Tyr Thr Glu Ser Asp Val His Pro Ser Cys Lys Val
        35                  40                  45

Thr Ala Met Lys Cys Phe Leu Leu Glu Leu Gln Val Ile Ser Leu Glu
    50                  55                  60

Ser Gly Asp Ala Ser Ile His Asp Thr Val Glu Asn Leu Ile Ile Leu
65                  70                  75                  80

Ala Asn Asn Ser Leu Ser Ser Asn Gly Asn Val Thr Glu Ser Gly Cys
                85                  90                  95

Lys Glu Cys Glu Glu Leu Glu Glu Lys Asn Ile Lys Glu Phe Leu Gln
            100                 105                 110

Ser Phe Val His Ile Val Gln Met Phe Ile Asn Thr Ser
        115                 120                 125

<210> SEQ ID NO 6
<211> LENGTH: 567
<212> TYPE: PRT
<213> ORGANISM: Homo sapiens

<400> SEQUENCE: 6

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

```
Gln Leu Cys Lys Phe Cys Asp Val Arg Phe Ser Thr Cys Asp Asn Gln
 50                  55                  60
Lys Ser Cys Met Ser Asn Cys Ser Ile Thr Ser Ile Cys Glu Lys Pro
 65                  70                  75                  80
Gln Glu Val Cys Val Ala Val Trp Arg Lys Asn Asp Glu Asn Ile Thr
                 85                  90                  95
Leu Glu Thr Val Cys His Asp Pro Lys Leu Pro Tyr His Asp Phe Ile
            100                 105                 110
Leu Glu Asp Ala Ala Ser Pro Lys Cys Ile Met Lys Glu Lys Lys Lys
            115                 120                 125
Pro Gly Glu Thr Phe Phe Met Cys Ser Cys Ser Ser Asp Glu Cys Asn
130                 135                 140
Asp Asn Ile Ile Phe Ser Glu Glu Tyr Asn Thr Ser Asn Pro Asp Leu
145                 150                 155                 160
Leu Leu Val Ile Phe Gln Val Thr Gly Ile Ser Leu Leu Pro Pro Leu
                165                 170                 175
Gly Val Ala Ile Ser Val Ile Ile Ile Phe Tyr Cys Tyr Arg Val Asn
            180                 185                 190
Arg Gln Gln Lys Leu Ser Ser Thr Trp Glu Thr Gly Lys Thr Arg Lys
            195                 200                 205
Leu Met Glu Phe Ser Glu His Cys Ala Ile Ile Leu Glu Asp Asp Arg
210                 215                 220
Ser Asp Ile Ser Ser Thr Cys Ala Asn Asn Ile Asn His Asn Thr Glu
225                 230                 235                 240
Leu Leu Pro Ile Glu Leu Asp Thr Leu Val Gly Lys Gly Arg Phe Ala
                245                 250                 255
Glu Val Tyr Lys Ala Lys Leu Lys Gln Asn Thr Ser Glu Gln Phe Glu
            260                 265                 270
Thr Val Ala Val Lys Ile Phe Pro Tyr Glu Glu Tyr Ala Ser Trp Lys
            275                 280                 285
Thr Glu Lys Asp Ile Phe Ser Asp Ile Asn Leu Lys His Glu Asn Ile
290                 295                 300
Leu Gln Phe Leu Thr Ala Glu Glu Arg Lys Thr Glu Leu Gly Lys Gln
305                 310                 315                 320
Tyr Trp Leu Ile Thr Ala Phe His Ala Lys Gly Asn Leu Gln Glu Tyr
                325                 330                 335
Leu Thr Arg His Val Ile Ser Trp Glu Asp Leu Arg Lys Leu Gly Ser
            340                 345                 350
Ser Leu Ala Arg Gly Ile Ala His Leu His Ser Asp His Thr Pro Cys
            355                 360                 365
Gly Arg Pro Lys Met Pro Ile Val His Arg Asp Leu Lys Ser Ser Asn
370                 375                 380
Ile Leu Val Lys Asn Asp Leu Thr Cys Cys Leu Cys Asp Phe Gly Leu
385                 390                 395                 400
Ser Leu Arg Leu Asp Pro Thr Leu Ser Val Asp Asp Leu Ala Asn Ser
                405                 410                 415
Gly Gln Val Gly Thr Ala Arg Tyr Met Ala Pro Glu Val Leu Glu Ser
            420                 425                 430
Arg Met Asn Leu Glu Asn Val Glu Ser Phe Lys Gln Thr Asp Val Tyr
            435                 440                 445
Ser Met Ala Leu Val Leu Trp Glu Met Thr Ser Arg Cys Asn Ala Val
450                 455                 460
Gly Glu Val Lys Asp Tyr Glu Pro Pro Phe Gly Ser Lys Val Arg Glu
```

```
                465                 470                 475                 480
His Pro Cys Val Glu Ser Met Lys Asp Asn Val Leu Arg Asp Arg Gly
                    485                 490                 495

Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
                515                 520                 525

Leu Thr Ala Gln Cys Val Ala Glu Arg Phe Ser Glu Leu Glu His Leu
530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 7
<211> LENGTH: 592
<212> TYPE: PRT
<213> ORGANISM: Homo sapiens

<400> SEQUENCE: 7

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
            35                  40                  45

Arg Thr Ala His Pro Leu Arg His Ile Asn Asn Asp Met Ile Val Thr
        50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
                100                 105                 110

Trp Arg Lys Asn Asp Glu Asn Ile Thr Leu Glu Thr Val Cys His Asp
            115                 120                 125

Pro Lys Leu Pro Tyr His Asp Phe Ile Leu Glu Asp Ala Ala Ser Pro
        130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
                180                 185                 190

Thr Gly Ile Ser Leu Leu Pro Pro Leu Gly Val Ala Ile Ser Val Ile
            195                 200                 205

Ile Ile Phe Tyr Cys Tyr Arg Val Asn Arg Gln Gln Lys Leu Ser Ser
        210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
                260                 265                 270
```

Thr Leu Val Gly Lys Gly Arg Phe Ala Glu Val Tyr Lys Ala Lys Leu
            275                 280                 285

Lys Gln Asn Thr Ser Glu Gln Phe Glu Thr Val Ala Val Lys Ile Phe
        290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
    370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
            420                 425                 430

Leu Ser Val Asp Asp Leu Ala Asn Ser Gly Gln Val Gly Thr Ala Arg
        435                 440                 445

Tyr Met Ala Pro Glu Val Leu Glu Ser Arg Met Asn Leu Glu Asn Val
    450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
            500                 505                 510

Lys Asp Asn Val Leu Arg Asp Arg Gly Arg Pro Glu Ile Pro Ser Phe
        515                 520                 525

Trp Leu Asn His Gln Gly Ile Gln Met Val Cys Glu Thr Leu Thr Glu
    530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 8
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ile Pro Pro His Val Gln Lys Ser Val Asn Asn Asp Met Ile Val Thr
1               5                   10                  15

Asp Asn Asn Gly Ala Val Lys Leu Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

```
Ser Ile Thr Ser Ile Cys Glu Lys Pro His Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Thr Tyr His Gly Phe Thr Leu Glu Asp Ala Ala Ser Pro
                85                  90                  95

Lys Cys Val Met Lys Glu Lys Lys Pro Gly Glu Thr Phe Phe Met
            100                 105                 110

Cys Ser Cys Ser Ala Asp Glu Cys Asn Asp Asn Ile Ile Phe Ser Glu
        115                 120                 125

Asp Tyr Asn Thr Ser Asn Pro Asp
    130                 135
```

<210> SEQ ID NO 9
<211> LENGTH: 161
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Ile Pro Pro His Val Gln Lys Ser Asp Val Glu Met Glu Ala Gln Lys
1               5                   10                  15

Gly Glu Met Ile Cys Val Thr Cys Asn Arg Thr Ala His Pro Leu Lys
            20                  25                  30

His Val Asn Asn Asp Met Ile Val Thr Asp Asn Gly Ala Val Lys
        35                  40                  45

Leu Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Thr Tyr His Gly
            100                 105                 110

Phe Thr Leu Glu Asp Ala Ala Ser Pro Lys Cys Val Met Lys Glu Lys
        115                 120                 125

Lys Lys Pro Gly Glu Thr Phe Phe Met Cys Ser Cys Ser Ser Asp Glu
    130                 135                 140

Cys Asn Asp Asn Ile Ile Phe Ser Glu Asp Tyr Asn Thr Ser Asn Pro
145                 150                 155                 160

Asp
```

<210> SEQ ID NO 10
<211> LENGTH: 409
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30
```

Gln Leu Glu His Leu Leu Asp Leu Gln Met Ile Leu Asn Gly Ile
        35                  40                  45

Asn Asn Tyr Lys Asn Pro Lys Leu Thr Arg Met Leu Thr Ala Lys Phe
 50                  55                  60

Tyr Met Pro Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                 85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
130                 135                 140

Cys Gln Ser Ile Ile Ser Thr Leu Gln Lys Ser Val Asn Asn Asp Met
145                 150                 155                 160

Ile Val Thr Asp Asn Asn Gly Ala Val Lys Leu Pro Gln Leu Cys Lys
                165                 170                 175

Phe Cys Asp Val Arg Phe Ser Thr Cys Asp Asn Gln Lys Ser Cys Met
            180                 185                 190

Ser Asn Cys Ser Ile Thr Ser Ile Cys Glu Lys Pro His Glu Val Cys
        195                 200                 205

Val Ala Val Trp Arg Lys Asn Asp Glu Asn Ile Thr Leu Glu Thr Val
    210                 215                 220

Cys His Asp Pro Lys Leu Thr Tyr His Gly Phe Thr Leu Glu Asp Ala
225                 230                 235                 240

Ala Ser Pro Lys Cys Val Met Lys Glu Lys Lys Pro Gly Glu Thr
                245                 250                 255

Phe Phe Met Cys Ser Cys Ser Ala Asp Glu Cys Asn Asp Asn Ile Ile
            260                 265                 270

Phe Ile Pro Pro His Val Gln Lys Ser Val Asn Asn Asp Met Ile Val
        275                 280                 285

Thr Asp Asn Asn Gly Ala Val Lys Leu Pro Gln Leu Cys Lys Phe Cys
290                 295                 300

Asp Val Arg Phe Ser Thr Cys Asp Asn Gln Lys Ser Cys Met Ser Asn
305                 310                 315                 320

Cys Ser Ile Thr Ser Ile Cys Glu Lys Pro His Glu Val Cys Val Ala
                325                 330                 335

Val Trp Arg Lys Asn Asp Glu Asn Ile Thr Leu Glu Thr Val Cys His
            340                 345                 350

Asp Pro Lys Leu Thr Tyr His Gly Phe Thr Leu Glu Asp Ala Ala Ser
        355                 360                 365

Pro Lys Cys Val Met Lys Glu Lys Lys Lys Pro Gly Glu Thr Phe Phe
    370                 375                 380

Met Cys Ser Cys Ser Ala Asp Glu Cys Asn Asp Asn Ile Ile Phe Ser
385                 390                 395                 400

Glu Asp Tyr Asn Thr Ser Asn Pro Asp
                405

<210> SEQ ID NO 11
<211> LENGTH: 424
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Ile Pro Pro His Val Gln Lys Ser
145                 150                 155                 160

Val Asn Asn Asp Met Ile Val Thr Asp Asn Asn Gly Ala Val Lys Leu
                165                 170                 175

Pro Gln Leu Cys Lys Phe Cys Asp Val Arg Phe Ser Thr Cys Asp Asn
            180                 185                 190

Gln Lys Ser Cys Met Ser Asn Cys Ser Ile Thr Ser Ile Cys Glu Lys
        195                 200                 205

Pro His Glu Val Cys Val Ala Val Trp Arg Lys Asn Asp Glu Asn Ile
210                 215                 220

Thr Leu Glu Thr Val Cys His Asp Pro Lys Leu Thr Tyr His Gly Phe
225                 230                 235                 240

Thr Leu Glu Asp Ala Ala Ser Pro Lys Cys Val Met Lys Glu Lys Lys
                245                 250                 255

Lys Pro Gly Glu Thr Phe Phe Met Cys Ser Cys Ser Ala Asp Glu Cys
            260                 265                 270

Asn Asp Asn Ile Ile Phe Ser Glu Asp Tyr Asn Thr Ser Asn Pro Asp
        275                 280                 285

Ile Pro Pro His Val Gln Lys Ser Val Asn Asn Asp Met Ile Val Thr
290                 295                 300

Asp Asn Asn Gly Ala Val Lys Leu Pro Gln Leu Cys Lys Phe Cys Asp
305                 310                 315                 320

Val Arg Phe Ser Thr Cys Asp Asn Gln Lys Ser Cys Met Ser Asn Cys
                325                 330                 335

Ser Ile Thr Ser Ile Cys Glu Lys Pro His Glu Val Cys Val Ala Val
            340                 345                 350

Trp Arg Lys Asn Asp Glu Asn Ile Thr Leu Glu Thr Val Cys His Asp
        355                 360                 365

Pro Lys Leu Thr Tyr His Gly Phe Thr Leu Glu Asp Ala Ala Ser Pro
370                 375                 380

Lys Cys Val Met Lys Glu Lys Lys Pro Gly Glu Thr Phe Phe Met
385                 390                 395                 400

Cys Ser Cys Ser Ala Asp Glu Cys Asn Asp Asn Ile Ile Phe Ser Glu
                405                 410                 415

Asp Tyr Asn Thr Ser Asn Pro Asp
            420

<210> SEQ ID NO 12
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Ala Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Gln Lys Ser Asp Val Glu Met Glu
145                 150                 155                 160

Ala Gln Lys Gly Glu Met Ile Cys Val Thr Cys Asn Arg Thr Ala His
                165                 170                 175

Pro Leu Lys His Val Asn Asn Asp Met Ile Val Thr Asp Asn Asn Gly
            180                 185                 190

Ala Val Lys Leu Pro Gln Leu Cys Lys Phe Cys Asp Val Arg Phe Ser
            195                 200                 205

Thr Cys Asp Asn Gln Lys Ser Cys Met Ser Asn Cys Ser Ile Thr Ser
            210                 215                 220

Ile Cys Glu Lys Pro Gln Glu Val Cys Val Ala Val Trp Arg Lys Asn
225                 230                 235                 240

Asp Glu Asn Ile Thr Leu Glu Thr Val Cys His Asp Pro Lys Leu Thr
                245                 250                 255

Tyr His Gly Phe Thr Leu Glu Asp Ala Ala Ser Pro Lys Cys Val Met
            260                 265                 270

Lys Glu Lys Lys Lys Pro Gly Glu Thr Phe Phe Met Cys Ser Cys Ser
        275                 280                 285

Ser Asp Glu Cys Asn Asp Asn Ile Ile Phe Ile Pro Pro His Val Gln
    290                 295                 300

Lys Ser Val Asn Asn Asp Met Ile Val Thr Asp Asn Asn Gly Ala Val
305                 310                 315                 320

Lys Leu Pro Gln Leu Cys Lys Phe Cys Asp Val Arg Phe Ser Thr Cys
                325                 330                 335

-continued

```
Asp Asn Gln Lys Ser Cys Met Ser Asn Cys Ser Ile Thr Ser Ile Cys
                340                 345                 350

Glu Lys Pro His Glu Val Cys Val Ala Val Trp Arg Lys Asn Asp Glu
            355                 360                 365

Asn Ile Thr Leu Glu Thr Val Cys His Asp Pro Lys Leu Thr Tyr His
        370                 375                 380

Gly Phe Thr Leu Glu Asp Ala Ala Ser Pro Lys Cys Val Met Lys Glu
385                 390                 395                 400

Lys Lys Lys Pro Gly Glu Thr Phe Phe Met Cys Ser Cys Ser Ala Asp
                405                 410                 415

Glu Cys Asn Asp Asn Ile Ile Phe Ser Glu Asp Tyr Asn Thr Ser Asn
            420                 425                 430

Pro Asp

<210> SEQ ID NO 13
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Gln Ile Pro Pro His Val Lys Ser
145                 150                 155                 160

Asp Val Glu Met Glu Ala Gln Lys Gly Glu Met Ile Cys Val Thr Cys
                165                 170                 175

Asn Arg Thr Ala His Pro Leu Lys His Val Asn Asn Asp Met Ile Val
            180                 185                 190

Thr Asp Asn Asn Gly Ala Val Lys Leu Pro Gln Leu Cys Lys Phe Cys
        195                 200                 205

Asp Val Arg Phe Ser Thr Cys Asp Asn Gln Lys Ser Cys Met Ser Asn
    210                 215                 220

Cys Ser Ile Thr Ser Ile Cys Glu Lys Pro Gln Glu Val Cys Val Ala
225                 230                 235                 240

Val Trp Arg Lys Asn Asp Glu Asn Ile Thr Leu Glu Thr Val Cys His
                245                 250                 255
```

-continued

```
Asp Pro Lys Leu Thr Tyr His Gly Phe Thr Leu Glu Asp Ala Ala Ser
            260                 265                 270

Pro Lys Cys Val Met Lys Glu Lys Lys Pro Gly Glu Thr Phe Phe
        275                 280                 285

Met Cys Ser Cys Ser Ser Asp Glu Cys Asn Asp Asn Ile Ile Phe Ser
290                 295                 300

Glu Asp Tyr Asn Thr Ser Asn Pro Asp Ile Pro Pro His Val Gln Lys
305                 310                 315                 320

Ser Val Asn Asn Asp Met Ile Val Thr Asp Asn Asn Gly Ala Val Lys
                325                 330                 335

Leu Pro Gln Leu Cys Lys Phe Cys Asp Val Arg Phe Ser Thr Cys Asp
            340                 345                 350

Asn Gln Lys Ser Cys Met Ser Asn Cys Ser Ile Thr Ser Ile Cys Glu
        355                 360                 365

Lys Pro His Glu Val Cys Val Ala Val Trp Arg Lys Asn Asp Glu Asn
    370                 375                 380

Ile Thr Leu Glu Thr Val Cys His Asp Pro Lys Leu Thr Tyr His Gly
385                 390                 395                 400

Phe Thr Leu Glu Asp Ala Ala Ser Pro Lys Cys Val Met Lys Glu Lys
                405                 410                 415

Lys Lys Pro Gly Glu Thr Phe Phe Met Cys Ser Cys Ser Ala Asp Glu
            420                 425                 430

Cys Asn Asp Asn Ile Ile Phe Ser Glu Asp Tyr Asn Thr Ser Asn Pro
        435                 440                 445

Asp

<210> SEQ ID NO 14
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Ala Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Gln Lys Ser Val Asn Asn Asp Met
145                 150                 155                 160
```

-continued

```
Ile Val Thr Asp Asn Asn Gly Ala Val Lys Leu Pro Gln Leu Cys Lys
                165                 170                 175

Phe Cys Asp Val Arg Phe Ser Thr Cys Asp Asn Gln Lys Ser Cys Met
            180                 185                 190

Ser Asn Cys Ser Ile Thr Ser Ile Cys Glu Lys Pro His Glu Val Cys
        195                 200                 205

Val Ala Val Trp Arg Lys Asn Asp Glu Asn Ile Thr Leu Glu Thr Val
    210                 215                 220

Cys His Asp Pro Lys Leu Thr Tyr His Gly Phe Thr Leu Glu Asp Ala
225                 230                 235                 240

Ala Ser Pro Lys Cys Val Met Lys Glu Lys Lys Pro Gly Glu Thr
                245                 250                 255

Phe Phe Met Cys Ser Cys Ser Ala Asp Glu Cys Asn Asp Asn Ile Ile
            260                 265                 270

Phe Ile Pro Pro His Val Gln Lys Ser Asp Val Glu Met Glu Ala Gln
        275                 280                 285

Lys Gly Glu Met Ile Cys Val Thr Cys Asn Arg Thr Ala His Pro Leu
    290                 295                 300

Lys His Val Asn Asn Asp Met Ile Val Thr Asp Asn Asn Gly Ala Val
305                 310                 315                 320

Lys Leu Pro Gln Leu Cys Lys Phe Cys Asp Val Arg Phe Ser Thr Cys
                325                 330                 335

Asp Asn Gln Lys Ser Cys Met Ser Asn Cys Ser Ile Thr Ser Ile Cys
            340                 345                 350

Glu Lys Pro Gln Glu Val Cys Val Ala Val Trp Arg Lys Asn Asp Glu
        355                 360                 365

Asn Ile Thr Leu Glu Thr Val Cys His Asp Pro Lys Leu Thr Tyr His
    370                 375                 380

Gly Phe Thr Leu Glu Asp Ala Ala Ser Pro Lys Cys Val Met Lys Glu
385                 390                 395                 400

Lys Lys Lys Pro Gly Glu Thr Phe Phe Met Cys Ser Cys Ser Ser Asp
                405                 410                 415

Glu Cys Asn Asp Asn Ile Ile Phe Ser Glu Asp Tyr Asn Thr Ser Asn
            420                 425                 430

Pro Asp

<210> SEQ ID NO 15
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80
```

Glu Glu Leu Lys Pro Leu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Ile Pro Pro His Val Gln Lys Ser
145                 150                 155                 160

Val Asn Asn Asp Met Ile Val Thr Asp Asn Asn Gly Ala Val Lys Leu
                165                 170                 175

Pro Gln Leu Cys Lys Phe Cys Asp Val Arg Phe Ser Thr Cys Asp Asn
            180                 185                 190

Gln Lys Ser Cys Met Ser Asn Cys Ser Ile Thr Ser Ile Cys Glu Lys
        195                 200                 205

Pro His Glu Val Cys Val Ala Val Trp Arg Lys Asn Asp Glu Asn Ile
210                 215                 220

Thr Leu Glu Thr Val Cys His Asp Pro Lys Leu Thr Tyr His Gly Phe
225                 230                 235                 240

Thr Leu Glu Asp Ala Ala Ser Pro Lys Cys Val Met Lys Glu Lys Lys
                245                 250                 255

Lys Pro Gly Glu Thr Phe Phe Met Cys Ser Cys Ser Ala Asp Glu Cys
            260                 265                 270

Asn Asp Asn Ile Ile Phe Ser Glu Asp Tyr Asn Thr Ser Asn Pro Asp
        275                 280                 285

Ile Pro Pro His Val Gln Lys Ser Asp Val Glu Met Glu Ala Gln Lys
290                 295                 300

Gly Glu Met Ile Cys Val Thr Cys Asn Arg Thr Ala His Pro Leu Lys
305                 310                 315                 320

His Val Asn Asn Asp Met Ile Val Thr Asp Asn Asn Gly Ala Val Lys
                325                 330                 335

Leu Pro Gln Leu Cys Lys Phe Cys Asp Val Arg Phe Ser Thr Cys Asp
            340                 345                 350

Asn Gln Lys Ser Cys Met Ser Asn Cys Ser Ile Thr Ser Ile Cys Glu
        355                 360                 365

Lys Pro Gln Glu Val Cys Val Ala Val Trp Arg Lys Asn Asp Glu Asn
370                 375                 380

Ile Thr Leu Glu Thr Val Cys His Asp Pro Lys Leu Thr Tyr His Gly
385                 390                 395                 400

Phe Thr Leu Glu Asp Ala Ala Ser Pro Lys Cys Val Met Lys Glu Lys
                405                 410                 415

Lys Lys Pro Gly Glu Thr Phe Phe Met Cys Ser Cys Ser Ser Asp Glu
            420                 425                 430

Cys Asn Asp Asn Ile Ile Phe Ser Glu Asp Tyr Asn Thr Ser Asn Pro
        435                 440                 445

Asp

<210> SEQ ID NO 16
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Ala Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Gln Lys Ser Asp Val Glu Met Glu
145                 150                 155                 160

Ala Gln Lys Gly Glu Met Ile Cys Val Thr Cys Asn Arg Thr Ala His
                165                 170                 175

Pro Leu Lys His Val Asn Asn Asp Met Ile Val Thr Asp Asn Asn Gly
            180                 185                 190

Ala Val Lys Leu Pro Gln Leu Cys Lys Phe Cys Asp Val Arg Phe Ser
        195                 200                 205

Thr Cys Asp Asn Gln Lys Ser Cys Met Ser Asn Cys Ser Ile Thr Ser
210                 215                 220

Ile Cys Glu Lys Pro Gln Glu Val Cys Val Ala Val Trp Arg Lys Asn
225                 230                 235                 240

Asp Glu Asn Ile Thr Leu Glu Thr Val Cys His Asp Pro Lys Leu Thr
                245                 250                 255

Tyr His Gly Phe Thr Leu Glu Asp Ala Ala Ser Pro Lys Cys Val Met
            260                 265                 270

Lys Glu Lys Lys Lys Pro Gly Glu Thr Phe Phe Met Cys Ser Cys Ser
        275                 280                 285

Ser Asp Glu Cys Asn Asp Asn Ile Ile Phe Ile Pro Pro His Val Lys
290                 295                 300

Ser Asp Val Glu Met Glu Ala Gln Lys Gly Glu Met Ile Cys Val Thr
305                 310                 315                 320

Cys Asn Arg Thr Ala His Pro Leu Lys His Val Asn Asn Asp Met Ile
                325                 330                 335

Val Thr Asp Asn Asn Gly Ala Val Lys Leu Pro Gln Leu Cys Lys Phe
            340                 345                 350

Cys Asp Val Arg Phe Ser Thr Cys Asp Asn Gln Lys Ser Cys Met Ser
        355                 360                 365

Asn Cys Ser Ile Thr Ser Ile Cys Glu Lys Pro Gln Glu Val Cys Val
370                 375                 380

Ala Val Trp Arg Lys Asn Asp Glu Asn Ile Thr Leu Glu Thr Val Cys
385                 390                 395                 400
```

His Asp Pro Lys Leu Thr Tyr His Gly Phe Thr Leu Glu Asp Ala Ala
            405                 410                 415

Ser Pro Lys Cys Val Met Lys Glu Lys Lys Pro Gly Glu Thr Phe
        420                 425                 430

Phe Met Cys Ser Cys Ser Ser Asp Glu Cys Asn Asp Asn Ile Ile Phe
        435                 440                 445

Ser Glu Asp Tyr Asn Thr Ser Asn Pro Asp
    450                 455

<210> SEQ ID NO 17
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Gln Ile Pro Pro His Val Lys Ser
145                 150                 155                 160

Asp Val Glu Met Glu Ala Gln Lys Gly Glu Met Ile Cys Val Thr Cys
                165                 170                 175

Asn Arg Thr Ala His Pro Leu Lys His Val Asn Asn Asp Met Ile Val
            180                 185                 190

Thr Asp Asn Asn Gly Ala Val Lys Leu Pro Gln Leu Cys Lys Phe Cys
        195                 200                 205

Asp Val Arg Phe Ser Thr Cys Asp Asn Gln Lys Ser Cys Met Ser Asn
210                 215                 220

Cys Ser Ile Thr Ser Ile Cys Glu Lys Pro Gln Glu Val Cys Val Ala
225                 230                 235                 240

Val Trp Arg Lys Asn Asp Glu Asn Ile Thr Leu Glu Thr Val Cys His
                245                 250                 255

Asp Pro Lys Leu Thr Tyr His Gly Phe Thr Leu Glu Asp Ala Ala Ser
            260                 265                 270

Pro Lys Cys Val Met Lys Glu Lys Lys Pro Gly Glu Thr Phe Phe
        275                 280                 285

Met Cys Ser Cys Ser Ser Asp Glu Cys Asn Asp Asn Ile Ile Phe Ser
290                 295                 300

```
Glu Asp Tyr Asn Thr Ser Asn Pro Asp Ile Pro Pro His Val Lys Ser
305                 310                 315                 320

Asp Val Glu Met Glu Ala Gln Lys Gly Glu Met Ile Cys Val Thr Cys
                325                 330                 335

Asn Arg Thr Ala His Pro Leu Lys His Val Asn Asn Asp Met Ile Val
            340                 345                 350

Thr Asp Asn Asn Gly Ala Val Lys Leu Pro Gln Leu Cys Lys Phe Cys
        355                 360                 365

Asp Val Arg Phe Ser Thr Cys Asp Asn Gln Lys Ser Cys Met Ser Asn
    370                 375                 380

Cys Ser Ile Thr Ser Ile Cys Glu Lys Pro Gln Glu Val Cys Val Ala
385                 390                 395                 400

Val Trp Arg Lys Asn Asp Glu Asn Ile Thr Leu Glu Thr Val Cys His
                405                 410                 415

Asp Pro Lys Leu Thr Tyr His Gly Phe Thr Leu Glu Asp Ala Ala Ser
            420                 425                 430

Pro Lys Cys Val Met Lys Glu Lys Lys Pro Gly Glu Thr Phe Phe
        435                 440                 445

Met Cys Ser Cys Ser Ser Asp Glu Cys Asn Asp Asn Ile Ile Phe Ser
    450                 455                 460

Glu Asp Tyr Asn Thr Ser Asn Pro Asp
465                 470

<210> SEQ ID NO 18
<211> LENGTH: 664
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Tyr Arg Met Gln Leu Leu Ser Cys Ile Ala Leu Ser Leu Ala Leu
1               5                   10                  15

Val Thr Asn Ser Ile Ser Ala Met Val Arg Ser Val Glu Cys Pro Pro
            20                  25                  30

Cys Pro Ala Pro Pro Val Ala Gly Pro Ser Val Phe Leu Phe Pro Pro
        35                  40                  45

Lys Pro Lys Asp Thr Leu Met Ile Ser Arg Thr Pro Glu Val Thr Cys
    50                  55                  60

Val Val Val Asp Val Ser His Glu Asp Pro Glu Val Lys Phe Asn Trp
65                  70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Gly Leu Pro Ser Ser Ile Glu Lys Thr Ile Ser Lys Ala Lys Gly
    130                 135                 140

Gln Pro Arg Glu Pro Gln Val Tyr Thr Leu Pro Pro Ser Arg Glu Glu
145                 150                 155                 160

Met Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
```

```
                180                 185                 190
Asn Tyr Lys Thr Thr Pro Pro Val Leu Asp Ser Asp Gly Ser Phe Phe
            195                 200                 205

Leu Tyr Ser Lys Leu Thr Val Asp Lys Ser Arg Trp Gln Gln Gly Asn
            210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys Ala Pro Thr Ser Ser Ser
            245                 250                 255

Thr Lys Lys Thr Gln Leu Gln Leu Glu His Leu Leu Leu Asp Leu Gln
            260                 265                 270

Met Ile Leu Asn Gly Ile Asn Asn Tyr Lys Asn Pro Lys Leu Thr Arg
            275                 280                 285

Met Leu Thr Ala Lys Phe Tyr Met Pro Lys Lys Ala Thr Glu Leu Lys
            290                 295                 300

His Leu Gln Cys Leu Glu Glu Glu Leu Lys Pro Leu Glu Glu Val Leu
305                 310                 315                 320

Asn Leu Ala Gln Ser Lys Asn Phe His Leu Arg Pro Arg Asp Leu Ile
            325                 330                 335

Ser Asn Ile Asn Val Ile Val Leu Glu Leu Lys Gly Ser Glu Thr Thr
            340                 345                 350

Phe Met Cys Glu Tyr Ala Asp Glu Thr Ala Thr Ile Val Glu Phe Leu
            355                 360                 365

Asn Arg Trp Ile Thr Phe Cys Gln Ser Ile Ile Ser Thr Leu Gln Lys
            370                 375                 380

Ser Asp Val Glu Met Glu Ala Gln Lys Gly Glu Met Ile Cys Val Thr
385                 390                 395                 400

Cys Asn Arg Thr Ala His Pro Leu Lys His Val Asn Asn Asp Met Ile
            405                 410                 415

Val Thr Asp Asn Asn Gly Ala Val Lys Leu Pro Gln Leu Cys Lys Phe
            420                 425                 430

Cys Asp Val Arg Phe Ser Thr Cys Asp Asn Gln Lys Ser Cys Met Ser
            435                 440                 445

Asn Cys Ser Ile Thr Ser Ile Cys Glu Lys Pro Gln Glu Val Cys Val
            450                 455                 460

Ala Val Trp Arg Lys Asn Asp Glu Asn Ile Thr Leu Glu Thr Val Cys
465                 470                 475                 480

His Asp Pro Lys Leu Thr Tyr His Gly Phe Thr Leu Glu Asp Ala Ala
            485                 490                 495

Ser Pro Lys Cys Val Met Lys Glu Lys Lys Pro Gly Glu Thr Phe
            500                 505                 510

Phe Met Cys Ser Cys Ser Ser Asp Glu Cys Asn Asp Asn Ile Ile Phe
            515                 520                 525

Ile Pro Pro His Val Gln Lys Ser Val Asn Asn Asp Met Ile Val Thr
            530                 535                 540

Asp Asn Asn Gly Ala Val Lys Leu Pro Gln Leu Cys Lys Phe Cys Asp
545                 550                 555                 560

Val Arg Phe Ser Thr Cys Asp Asn Gln Lys Ser Cys Met Ser Asn Cys
            565                 570                 575

Ser Ile Thr Ser Ile Cys Glu Lys Pro His Glu Val Cys Val Ala Val
            580                 585                 590

Trp Arg Lys Asn Asp Glu Asn Ile Thr Leu Glu Thr Val Cys His Asp
            595                 600                 605
```

```
Pro Lys Leu Thr Tyr His Gly Phe Thr Leu Glu Asp Ala Ala Ser Pro
        610                 615                 620

Lys Cys Val Met Lys Glu Lys Lys Pro Gly Glu Thr Phe Phe Met
625                 630                 635                 640

Cys Ser Cys Ser Ala Asp Glu Cys Asn Asp Asn Ile Ile Phe Ser Glu
                645                 650                 655

Asp Tyr Asn Thr Ser Asn Pro Asp
            660

<210> SEQ ID NO 19
<211> LENGTH: 639
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Tyr Arg Met Gln Leu Leu Ser Cys Ile Ala Leu Ser Leu Ala Leu
1               5                   10                  15

Val Thr Asn Ser Ile Ser Ala Met Val Arg Ser Val Glu Cys Pro Pro
            20                  25                  30

Cys Pro Ala Pro Pro Val Ala Gly Pro Ser Val Phe Leu Phe Pro Pro
            35                  40                  45

Lys Pro Lys Asp Thr Leu Met Ile Ser Arg Thr Pro Glu Val Thr Cys
    50                  55                  60

Val Val Val Asp Val Ser His Glu Asp Pro Glu Val Lys Phe Asn Trp
65              70                  75                  80

Tyr Val Asp Gly Val Glu Val His Asn Ala Lys Thr Lys Pro Arg Glu
                85                  90                  95

Glu Gln Tyr Asn Ser Thr Tyr Arg Val Val Ser Val Leu Thr Val Leu
            100                 105                 110

His Gln Asp Trp Leu Asn Gly Lys Glu Tyr Lys Cys Lys Val Ser Asn
        115                 120                 125

Lys Gly Leu Pro Ser Ser Ile Glu Lys Thr Ile Ser Lys Ala Lys Gly
    130                 135                 140

Gln Pro Arg Glu Pro Gln Val Tyr Thr Leu Pro Pro Ser Arg Glu Glu
145                 150                 155                 160

Met Thr Lys Asn Gln Val Ser Leu Thr Cys Leu Val Lys Gly Phe Tyr
                165                 170                 175

Pro Ser Asp Ile Ala Val Glu Trp Glu Ser Asn Gly Gln Pro Glu Asn
            180                 185                 190

Asn Tyr Lys Thr Thr Pro Pro Val Leu Asp Ser Asp Gly Ser Phe Phe
        195                 200                 205

Leu Tyr Ser Lys Leu Thr Val Asp Lys Ser Arg Trp Gln Gln Gly Asn
    210                 215                 220

Val Phe Ser Cys Ser Val Met His Glu Ala Leu His Asn His Tyr Thr
225                 230                 235                 240

Gln Lys Ser Leu Ser Leu Ser Pro Gly Lys Ala Pro Thr Ser Ser Ser
                245                 250                 255

Thr Lys Lys Thr Gln Leu Gln Leu Glu His Leu Leu Leu Asp Leu Gln
            260                 265                 270

Met Ile Leu Asn Gly Ile Asn Asn Tyr Lys Asn Pro Lys Leu Thr Arg
        275                 280                 285

Met Leu Thr Ala Lys Phe Tyr Met Pro Lys Lys Ala Thr Glu Leu Lys
```

```
            290                 295                 300

His Leu Gln Cys Leu Glu Glu Leu Lys Pro Leu Glu Glu Val Leu
305                 310                 315                 320

Asn Leu Ala Gln Ser Lys Asn Phe His Leu Arg Pro Arg Asp Leu Ile
                325                 330                 335

Ser Asn Ile Asn Val Ile Val Leu Glu Leu Lys Gly Ser Glu Thr Thr
            340                 345                 350

Phe Met Cys Glu Tyr Ala Asp Glu Thr Ala Thr Ile Val Glu Phe Leu
        355                 360                 365

Asn Arg Trp Ile Thr Phe Cys Gln Ser Ile Ile Ser Thr Leu Gln Lys
370                 375                 380

Ser Val Asn Asn Asp Met Ile Val Thr Asp Asn Asn Gly Ala Val Lys
385                 390                 395                 400

Leu Pro Gln Leu Cys Lys Phe Cys Asp Val Arg Phe Ser Thr Cys Asp
                405                 410                 415

Asn Gln Lys Ser Cys Met Ser Asn Cys Ser Ile Thr Ser Ile Cys Glu
            420                 425                 430

Lys Pro His Glu Val Cys Val Ala Val Trp Arg Lys Asn Asp Glu Asn
        435                 440                 445

Ile Thr Leu Glu Thr Val Cys His Asp Pro Lys Leu Thr Tyr His Gly
450                 455                 460

Phe Thr Leu Glu Asp Ala Ala Ser Pro Lys Cys Val Met Lys Glu Lys
465                 470                 475                 480

Lys Lys Pro Gly Glu Thr Phe Phe Met Cys Ser Cys Ser Ala Asp Glu
                485                 490                 495

Cys Asn Asp Asn Ile Ile Phe Ile Pro Pro His Val Gln Lys Ser Val
            500                 505                 510

Asn Asn Asp Met Ile Val Thr Asp Asn Asn Gly Ala Val Lys Leu Pro
        515                 520                 525

Gln Leu Cys Lys Phe Cys Asp Val Arg Phe Ser Thr Cys Asp Asn Gln
530                 535                 540

Lys Ser Cys Met Ser Asn Cys Ser Ile Thr Ser Ile Cys Glu Lys Pro
545                 550                 555                 560

His Glu Val Cys Val Ala Val Trp Arg Lys Asn Asp Glu Asn Ile Thr
                565                 570                 575

Leu Glu Thr Val Cys His Asp Pro Lys Leu Thr Tyr His Gly Phe Thr
            580                 585                 590

Leu Glu Asp Ala Ala Ser Pro Lys Cys Val Met Lys Glu Lys Lys Lys
        595                 600                 605

Pro Gly Glu Thr Phe Phe Met Cys Ser Cys Ser Ala Asp Glu Cys Asn
610                 615                 620

Asp Asn Ile Ile Phe Ser Glu Asp Tyr Asn Thr Ser Asn Pro Asp
625                 630                 635

<210> SEQ ID NO 20
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Tyr Arg Met Gln Leu Leu Ser Cys Ile Ala Leu Ser Leu Ala Leu
1               5                   10                  15
```

Val Thr Asn Ser Ile Pro Pro His Val Gln Lys Ser Val Asn Asn Asp
             20                  25                  30

Met Ile Val Thr Asp Asn Asn Gly Ala Val Lys Leu Pro Gln Leu Cys
         35                  40                  45

Lys Phe Cys Asp Val Arg Phe Ser Thr Cys Asp Asn Gln Lys Ser Cys
     50                  55                  60

Met Ser Asn Cys Ser Ile Thr Ser Ile Cys Glu Lys Pro His Glu Val
65                  70                  75                  80

Cys Val Ala Val Trp Arg Lys Asn Asp Glu Asn Ile Thr Leu Glu Thr
                 85                  90                  95

Val Cys His Asp Pro Lys Leu Thr Tyr His Gly Phe Thr Leu Glu Asp
             100                 105                 110

Ala Ala Ser Pro Lys Cys Val Met Lys Glu Lys Lys Pro Gly Glu
         115                 120                 125

Thr Phe Phe Met Cys Ser Cys Ser Ala Asp Glu Cys Asn Asp Asn Ile
     130                 135                 140

Ile Phe Ser Glu Asp Tyr Asn Thr Ser Asn Pro Asp Ala Pro Thr Ser
145                 150                 155                 160

Ser Ser Thr Lys Lys Thr Gln Leu Gln Leu Glu His Leu Leu Leu Asp
                 165                 170                 175

Leu Gln Met Ile Leu Asn Gly Ile Asn Asn Tyr Lys Asn Pro Lys Leu
             180                 185                 190

Thr Arg Met Leu Thr Ala Lys Phe Tyr Met Pro Lys Lys Ala Thr Glu
         195                 200                 205

Leu Lys His Leu Gln Cys Leu Glu Glu Glu Leu Lys Pro Leu Glu Glu
     210                 215                 220

Val Leu Asn Leu Ala Gln Ser Lys Asn Phe His Leu Arg Pro Arg Asp
225                 230                 235                 240

Leu Ile Ser Asn Ile Asn Val Ile Val Leu Glu Leu Lys Gly Ser Glu
                 245                 250                 255

Thr Thr Phe Met Cys Glu Tyr Ala Asp Glu Thr Ala Thr Ile Val Glu
             260                 265                 270

Phe Leu Asn Arg Trp Ile Thr Phe Cys Gln Ser Ile Ile Ser Thr Leu
         275                 280                 285

Gln Lys Ser Val Asn Asn Asp Met Ile Val Thr Asp Asn Asn Gly Ala
     290                 295                 300

Val Lys Leu Pro Gln Leu Cys Lys Phe Cys Asp Val Arg Phe Ser Thr
305                 310                 315                 320

Cys Asp Asn Gln Lys Ser Cys Met Ser Asn Cys Ser Ile Thr Ser Ile
                 325                 330                 335

Cys Glu Lys Pro His Glu Val Cys Val Ala Val Trp Arg Lys Asn Asp
             340                 345                 350

Glu Asn Ile Thr Leu Glu Thr Val Cys His Asp Pro Lys Leu Thr Tyr
         355                 360                 365

His Gly Phe Thr Leu Glu Asp Ala Ala Ser Pro Lys Cys Val Met Lys
     370                 375                 380

Glu Lys Lys Lys Pro Gly Glu Thr Phe Phe Met Cys Ser Cys Ser Ala
385                 390                 395                 400

Asp Glu Cys Asn Asp Asn Ile Ile Phe Ser Glu Asp Tyr Asn Thr Ser
                 405                 410                 415

Asn Pro Asp

<210> SEQ ID NO 21

<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Met Tyr Arg Met Gln Leu Leu Ser Cys Ile Ala Leu Ser Leu Ala Leu
1               5                   10                  15

Val Thr Asn Ser Ile Pro Pro His Val Gln Lys Ser Val Asn Asn Asp
            20                  25                  30

Met Ile Val Thr Asp Asn Asn Gly Ala Val Lys Leu Pro Gln Leu Cys
        35                  40                  45

Lys Phe Cys Asp Val Arg Phe Ser Thr Cys Asp Asn Gln Lys Ser Cys
    50                  55                  60

Met Ser Asn Cys Ser Ile Thr Ser Ile Cys Glu Lys Pro His Glu Val
65                  70                  75                  80

Cys Val Ala Val Trp Arg Lys Asn Asp Glu Asn Ile Thr Leu Glu Thr
                85                  90                  95

Val Cys His Asp Pro Lys Leu Thr Tyr His Gly Phe Thr Leu Glu Asp
            100                 105                 110

Ala Ala Ser Pro Lys Cys Val Met Lys Glu Lys Lys Pro Gly Glu
        115                 120                 125

Thr Phe Phe Met Cys Ser Cys Ser Ala Asp Glu Cys Asn Asp Asn Ile
    130                 135                 140

Ile Phe Ser Glu Asp Tyr Asn Thr Ser Asn Pro Asp Ala Pro Thr Ser
145                 150                 155                 160

Ser Ser Thr Lys Lys Thr Gln Leu Gln Leu Glu His Leu Leu Leu Asp
                165                 170                 175

Leu Gln Met Ile Leu Asn Gly Ile Asn Asn Tyr Lys Asn Pro Lys Leu
            180                 185                 190

Thr Arg Met Leu Thr Ala Lys Phe Tyr Met Pro Lys Lys Ala Thr Glu
        195                 200                 205

Leu Lys His Leu Gln Cys Leu Glu Glu Glu Leu Lys Pro Leu Glu Glu
    210                 215                 220

Val Leu Asn Leu Ala Gln Ser Lys Asn Phe His Leu Arg Pro Arg Asp
225                 230                 235                 240

Leu Ile Ser Asn Ile Asn Val Ile Val Leu Glu Leu Lys Gly Ser Glu
                245                 250                 255

Thr Thr Phe Met Cys Glu Tyr Ala Asp Glu Thr Ala Thr Ile Val Glu
            260                 265                 270

Phe Leu Asn Arg Trp Ile Thr Phe Cys Gln Ser Ile Ile Ser Thr Leu
        275                 280                 285

Gln Lys Ser Asp Val Glu Met Glu Ala Gln Lys Gly Glu Met Ile Cys
    290                 295                 300

Val Thr Cys Asn Arg Thr Ala His Pro Lys His Val Asn Asn Asp
305                 310                 315                 320

Met Ile Val Thr Asp Asn Asn Gly Ala Val Lys Leu Pro Gln Leu Cys
                325                 330                 335

Lys Phe Cys Asp Val Arg Phe Ser Thr Cys Asp Asn Gln Lys Ser Cys
            340                 345                 350

Met Ser Asn Cys Ser Ile Thr Ser Ile Cys Glu Lys Pro Gln Glu Val
        355                 360                 365

Cys Val Ala Val Trp Arg Lys Asn Asp Glu Asn Ile Thr Leu Glu Thr
```

```
                370               375                380
Val Cys His Asp Pro Lys Leu Thr Tyr His Gly Phe Thr Leu Glu Asp
385                 390                 395                 400

Ala Ala Ser Pro Lys Cys Val Met Lys Glu Lys Lys Pro Gly Glu
                405                 410                 415

Thr Phe Phe Met Cys Ser Cys Ser Ser Asp Glu Cys Asn Asp Asn Ile
                420                 425                 430

Ile Phe Ser Glu Asp Tyr Asn Thr Ser Asn Pro Asp
                435                 440
```

<210> SEQ ID NO 22
<211> LENGTH: 468
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Tyr Arg Met Gln Leu Leu Ser Cys Ile Ala Leu Ser Leu Ala Leu
1               5                   10                  15

Val Thr Asn Ser Ile Pro Pro His Val Lys Ser Asp Val Glu Met Glu
                20                  25                  30

Ala Gln Lys Gly Glu Met Ile Cys Val Thr Cys Asn Arg Thr Ala His
                35                  40                  45

Pro Leu Lys His Val Asn Asn Asp Met Ile Val Thr Asp Asn Asn Gly
            50                  55                  60

Ala Val Lys Leu Pro Gln Leu Cys Lys Phe Cys Asp Val Arg Phe Ser
65                  70                  75                  80

Thr Cys Asp Asn Gln Lys Ser Cys Met Ser Asn Cys Ser Ile Thr Ser
                85                  90                  95

Ile Cys Glu Lys Pro Gln Glu Val Cys Val Ala Val Trp Arg Lys Asn
                100                 105                 110

Asp Glu Asn Ile Thr Leu Glu Thr Val Cys His Asp Pro Lys Leu Thr
            115                 120                 125

Tyr His Gly Phe Thr Leu Glu Asp Ala Ala Ser Pro Lys Cys Val Met
        130                 135                 140

Lys Glu Lys Lys Pro Gly Glu Thr Phe Phe Met Cys Ser Cys Ser Ser
145                 150                 155                 160

Ser Asp Glu Cys Asn Asp Asn Ile Ile Phe Ser Glu Asp Tyr Asn Thr
                165                 170                 175

Ser Asn Pro Asp Ala Pro Thr Ser Ser Thr Lys Lys Thr Gln Leu
            180                 185                 190

Gln Leu Glu His Leu Leu Leu Asp Leu Gln Met Ile Leu Asn Gly Ile
        195                 200                 205

Asn Asn Tyr Lys Asn Pro Lys Leu Thr Arg Met Leu Thr Ala Lys Phe
    210                 215                 220

Tyr Met Pro Lys Lys Ala Thr Glu Leu Lys His Leu Gln Cys Leu Glu
225                 230                 235                 240

Glu Glu Leu Lys Pro Leu Glu Glu Val Leu Asn Leu Ala Gln Ser Lys
                245                 250                 255

Asn Phe His Leu Arg Pro Arg Asp Leu Ile Ser Asn Ile Asn Val Ile
                260                 265                 270

Val Leu Glu Leu Lys Gly Ser Glu Thr Thr Phe Met Cys Glu Tyr Ala
            275                 280                 285
```

```
Asp Glu Thr Ala Thr Ile Val Glu Phe Leu Asn Arg Trp Ile Thr Phe
    290                 295                 300

Cys Gln Ser Ile Ile Ser Thr Leu Gln Lys Ser Asp Val Glu Met Glu
305                 310                 315                 320

Ala Gln Lys Gly Glu Met Ile Cys Val Thr Cys Asn Arg Thr Ala His
                325                 330                 335

Pro Leu Lys His Val Asn Asn Asp Met Ile Val Thr Asp Asn Asn Gly
            340                 345                 350

Ala Val Lys Leu Pro Gln Leu Cys Lys Phe Cys Asp Val Arg Phe Ser
        355                 360                 365

Thr Cys Asp Asn Gln Lys Ser Cys Met Ser Asn Cys Ser Ile Thr Ser
370                 375                 380

Ile Cys Glu Lys Pro Gln Glu Val Cys Val Ala Val Trp Arg Lys Asn
385                 390                 395                 400

Asp Glu Asn Ile Thr Leu Glu Thr Val Cys His Asp Pro Lys Leu Thr
                405                 410                 415

Tyr His Gly Phe Thr Leu Glu Asp Ala Ala Ser Pro Lys Cys Val Met
            420                 425                 430

Lys Glu Lys Lys Lys Pro Gly Glu Thr Phe Phe Met Cys Ser Cys Ser
        435                 440                 445

Ser Asp Glu Cys Asn Asp Asn Ile Ile Phe Ser Glu Asp Tyr Asn Thr
450                 455                 460

Ser Asn Pro Asp
465

<210> SEQ ID NO 23
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Gln Lys Ser Asp Val Glu Met Glu
145                 150                 155                 160

Ala Gln Lys Gly Glu Met Ile Cys Val Thr Cys Asn Arg Thr Ala His
                165                 170                 175
```

```
Pro Leu Lys His Val Asn Asn Asp Met Ile Val Thr Asp Asn Asn Gly
            180                 185                 190

Ala Val Lys Leu Pro Gln Leu Cys Lys Phe Cys Asp Val Arg Phe Ser
        195                 200                 205

Thr Cys Asp Asn Gln Lys Ser Cys Met Ser Asn Cys Ser Ile Thr Ser
    210                 215                 220

Ile Cys Glu Lys Pro Gln Glu Val Cys Val Ala Val Trp Arg Lys Asn
225                 230                 235                 240

Asp Glu Asn Ile Thr Leu Glu Thr Val Cys His Asp Pro Lys Leu Thr
                245                 250                 255

Tyr His Gly Phe Thr Leu Glu Asp Ala Ala Ser Pro Lys Cys Val Met
            260                 265                 270

Lys Glu Lys Lys Pro Gly Glu Thr Phe Phe Met Cys Ser Cys Ser
        275                 280                 285

Ser Asp Glu Cys Asn Asp Asn Ile Ile Phe Ser Glu Asp Tyr Asn Thr
    290                 295                 300

Ser Asn Pro Asp
305
```

<210> SEQ ID NO 24
<211> LENGTH: 308
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Ala Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Gln Lys Ser Asp Val Glu Met Glu
145                 150                 155                 160

Ala Gln Lys Gly Glu Met Ile Cys Val Thr Cys Asn Arg Thr Ala His
                165                 170                 175

Pro Leu Lys His Val Asn Asn Asp Met Ile Val Thr Asp Asn Asn Gly
            180                 185                 190

Ala Val Lys Leu Pro Gln Leu Cys Lys Phe Cys Asp Val Arg Phe Ser
        195                 200                 205

Thr Cys Asp Asn Gln Lys Ser Cys Met Ser Asn Cys Ser Ile Thr Ser
```

```
            210                 215                 220
Ile Cys Glu Lys Pro Gln Glu Val Cys Val Ala Val Trp Arg Lys Asn
225                 230                 235                 240

Asp Glu Asn Ile Thr Leu Glu Thr Val Cys His Asp Pro Lys Leu Thr
                245                 250                 255

Tyr His Gly Phe Thr Leu Glu Asp Ala Ala Ser Pro Lys Cys Val Met
                260                 265                 270

Lys Glu Lys Lys Pro Gly Glu Thr Phe Phe Met Cys Ser Cys Ser
                275                 280                 285

Ser Asp Glu Cys Asn Asp Asn Ile Ile Phe Ser Glu Asp Tyr Asn Thr
                290                 295                 300

Ser Asn Pro Asp
305

<210> SEQ ID NO 25
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Ala Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Gln Lys Ser Val Asn Asn Asp Met
145                 150                 155                 160

Ile Val Thr Asp Asn Asn Gly Ala Val Lys Leu Pro Gln Leu Cys Lys
                165                 170                 175

Phe Cys Asp Val Arg Phe Ser Thr Cys Asp Asn Gln Lys Ser Cys Met
            180                 185                 190

Ser Asn Cys Ser Ile Thr Ser Ile Cys Glu Lys Pro His Glu Val Cys
        195                 200                 205

Val Ala Val Trp Arg Lys Asn Asp Glu Asn Ile Thr Leu Glu Thr Val
    210                 215                 220

Cys His Asp Pro Lys Leu Thr Tyr His Gly Phe Thr Leu Glu Asp Ala
225                 230                 235                 240

Ala Ser Pro Lys Cys Val Met Lys Glu Lys Lys Pro Gly Glu Thr
                245                 250                 255
```

```
Phe Phe Met Cys Ser Cys Ser Ala Asp Glu Cys Asn Asp Asn Ile Ile
            260                 265                 270

Phe Ser Glu Asp Tyr Asn Thr Ser Asn Pro Asp
        275                 280
```